United States Patent
Tamraz et al.

(10) Patent No.: US 10,668,011 B2
(45) Date of Patent: *Jun. 2, 2020

(54) DEPOT FORMULATIONS

(71) Applicants: DURECT CORPORATION, Cupertino, CA (US); SANTEN PHARMACEUTICAL CO., LTD., Osaka (JP)

(72) Inventors: Wilma Tamraz, San Jose, CA (US); Huey-Ching Su, San Jose, CA (US); WeiQi Lin, Emerald Hills, CA (US); Kazuhito Yamada, Nara (JP); Naoki Matsumoto, Nara (JP); Sreenivasu Mudumba, Emeryville, CA (US); Komei Okabe, Nara (JP)

(73) Assignees: DURECT CORPORATION, Cupertino, CA (US); SANTEN PHARMACEUTICAL CO., LTD., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/637,401

(22) Filed: Jun. 29, 2017

(65) Prior Publication Data

US 2018/0000729 A1 Jan. 4, 2018

Related U.S. Application Data

(60) Provisional application No. 62/440,658, filed on Dec. 30, 2016, provisional application No. 62/356,613, filed on Jun. 30, 2016.

(51) Int. Cl.
*A61K 9/00* (2006.01)
*A61K 31/436* (2006.01)
(Continued)

(52) U.S. Cl.
CPC .......... *A61K 9/0051* (2013.01); *A61K 31/355* (2013.01); *A61K 31/436* (2013.01);
(Continued)

(58) Field of Classification Search
None
See application file for complete search history.

(56) References Cited

U.S. PATENT DOCUMENTS 4,443,340 A 4/1984 May et al.
5,023,262 A 6/1991 Caulfield et al.
(Continued)

FOREIGN PATENT DOCUMENTS

CN 1973822 A 6/2007
EP 0467606 1/1992
(Continued)

OTHER PUBLICATIONS

Erlandsson, B., "Stability-indicating changes in polozamers: the degradations of ethylene oxide-propylene oxide block copolymers at 25 and 40 C", *Polymer Degradation and Stability*, 78, pp. 571-575, 2002.
(Continued)

*Primary Examiner* — Isis A Ghali
(74) *Attorney, Agent, or Firm* — Greenblum & Bernstein, P.L.C.

(57) ABSTRACT

Pharmaceutical compositions comprising an active pharmaceutical ingredient, a high viscosity liquid carrier material, a hydrophobic solvent, and a hydrophilic solvent are disclosed. Also disclosed are methods of manufacturing and using the compositions. The compositions are suitable for use, e.g., as depot formulations.

10 Claims, 27 Drawing Sheets

(51) Int. Cl.

| | | |
|---|---|---|
| A61K 31/355 | (2006.01) | |
| A61K 45/06 | (2006.01) | |
| A61K 47/10 | (2017.01) | |
| A61K 47/14 | (2017.01) | |
| A61K 47/26 | (2006.01) | |
| C08G 65/26 | (2006.01) | |
| A61K 31/7032 | (2006.01) | |
| C07C 31/08 | (2006.01) | |
| C08G 65/34 | (2006.01) | |
| C12P 19/12 | (2006.01) | |

(52) U.S. Cl.
CPC .............. *A61K 45/06* (2013.01); *A61K 47/10* (2013.01); *A61K 47/14* (2013.01); *A61K 47/26* (2013.01); *A61K 31/7032* (2013.01); *C07C 31/08* (2013.01); *C08G 65/26* (2013.01); *C08G 65/34* (2013.01); *C12P 19/12* (2013.01)

(56) References Cited

U.S. PATENT DOCUMENTS

| | | | |
|---|---|---|---|
| 5,100,899 | A | 3/1992 | Calne |
| 5,120,725 | A | 6/1992 | Kao et al. |
| 5,120,727 | A | 6/1992 | Kao et al. |
| 5,120,842 | A | 6/1992 | Failli et al. |
| 5,145,684 | A | 9/1992 | Liversidge et al. |
| 5,177,203 | A | 1/1993 | Failli et al. |
| 5,212,155 | A | 5/1993 | Calne |
| 5,242,910 | A | 9/1993 | Damanj |
| 5,310,865 | A | 5/1994 | Enomoto et al. |
| 5,387,589 | A | 2/1995 | Kulkarni |
| 5,403,833 | A | 4/1995 | Calne |
| 5,527,907 | A | 6/1996 | Or et al. |
| 5,536,729 | A | 7/1996 | Waranis et al. |
| 5,747,058 | A | 5/1998 | Tipton et al. |
| 5,968,542 | A | 10/1999 | Tipton |
| 5,989,591 | A | 11/1999 | Nagi |
| 6,329,386 | B1 | 12/2001 | Mollison |
| 6,376,517 | B1 | 4/2002 | Ross et al. |
| 6,890,546 | B2 | 5/2005 | Mollison et al. |
| 7,824,700 | B2 | 11/2010 | Cleland et al. |
| 7,833,543 | B2 | 11/2010 | Gibson et al. |
| 7,906,136 | B2 | 3/2011 | Wong et al. |
| 8,222,271 | B2 | 7/2012 | Kleinman et al. |
| 8,313,763 | B2 | 11/2012 | Margaron et al. |
| 8,367,097 | B2 | 2/2013 | Mudumba et al. |
| 8,415,401 | B2 | 4/2013 | Yum et al. |
| 8,492,400 | B2 | 7/2013 | Mudumba et al. |
| 8,501,216 | B2 | 8/2013 | Cleland et al. |
| 8,618,088 | B2 | 12/2013 | Wen et al. |
| 8,637,070 | B2 | 1/2014 | Mudumba et al. |
| 8,663,639 | B2 | 3/2014 | Dor |
| 8,846,072 | B2 | 9/2014 | Verity |
| 8,852,638 | B2 | 10/2014 | Luk et al. |
| 9,011,915 | B2 | 4/2015 | Wong et al. |
| 9,233,160 | B2 | 1/2016 | Yum et al. |
| 2004/0101557 | A1 | 5/2004 | Gibson et al. |
| 2004/0151753 | A1 | 8/2004 | Chen et al. |
| 2005/0064010 | A1 | 3/2005 | Cooper et al. |
| 2006/0257450 | A1 | 11/2006 | Mudumba et al. |
| 2006/0264453 | A1 | 11/2006 | Mudumba et al. |
| 2007/0280992 | A1 | 12/2007 | Margaron et al. |
| 2008/0038316 | A1 | 2/2008 | Wong et al. |
| 2010/0034801 | A1 | 2/2010 | Li et al. |
| 2012/0034279 | A1 | 2/2012 | Cooper et al. |
| 2012/0114637 | A1 | 5/2012 | Nivaggioli et al. |
| 2012/0225033 | A1 | 9/2012 | Van Osdol et al. |
| 2012/0330005 | A1 | 12/2012 | Junnarkar et al. |
| 2013/0189369 | A1 | 7/2013 | Marsh et al. |
| 2013/0289069 | A1 | 10/2013 | Verity |
| 2014/0294977 | A1 | 10/2014 | Sekar et al. |
| 2015/0265581 | A1 | 9/2015 | Kleinman et al. |
| 2016/0038479 | A1 | 2/2016 | Zamloot et al. |
| 2016/0038592 | A1 | 2/2016 | Yum et al. |
| 2016/0038596 | A1 | 2/2016 | Wright et al. |
| 2016/0303093 | A1 | 10/2016 | Mudumba et al. |
| 2018/0042907 | A1 | 2/2018 | Okabe et al. |
| 2018/0185489 | A1 | 7/2018 | Miyazaki et al. |

FOREIGN PATENT DOCUMENTS

| | | |
|---|---|---|
| EP | 1372729 | 1/2004 |
| EP | 2167039 | 3/2010 |
| EP | 1793803 | 6/2017 |
| WO | 92/05179 | 4/1992 |
| WO | 2004/011054 | 2/2004 |
| WO | 2004/081196 | 9/2004 |
| WO | 2007/092620 | 8/2007 |
| WO | 2008/082563 | 7/2008 |
| WO | 2008/143992 | 11/2008 |
| WO | 2014/190248 | 11/2014 |
| WO | 2016/079330 | 5/2016 |
| WO | 2016/148228 | 9/2016 |
| WO | 2017/002941 | 1/2017 |
| WO | 2018/005777 | 1/2018 |
| WO | 2018/128173 | 7/2018 |

OTHER PUBLICATIONS

Fallor, M.K., et al., "Ocular toxicity of experimental intravitreal vitamin E", *J. Toxicol.—Cut. & Ocular Toxicol.*, 3(4), 337-345, 1984.

Hayward et al., "Total Synthesis of Rapamycin Via a Novel Titanium-Mediated Aldol Macrocyclization Reaction", J. Am. Chem. Soc., 115, 1993, pp. 9345-9346.

Manzano, R., et al., "Testing intravitreal toxicity of rapamycin in rabbit eyes", *Arq. Bras. Oftalmol.*, 72(1), pp. 18-22, 2009.

Nicolaou et al., "Total Synthesis of Rapamycin", J. Am. Chem. Soc., 115, 1993, pp. 4419-4420.

Paiva et al., "Incorporation of Acetate, Propionate, and Methionine Into Rapamycin by Streptomycetes hygroscopicus", J Nat Prod, 54, 1991, pp. 167-177.

Romo et al., "Total Synthesis of (-) Rapamycin Using an Evans-Tishchenko Fragment Coupling", J. Am. Chem. Soc., 115, 1993, pp. 7906-7907.

Sehgal et al., "Rapamycin (AY-22,989), A New Antifungal Antibiotic. II. Fermentation, Isolation and Characterization", J. Antibiot. (Tokyo), 28, 1975, pp. 727-732.

Sehgal et al., "Demethoxyrapamycin (AY-24,668), A New Antifungal Antibiotic", J. Antibiot. (Tokyo) 36, 1983, pp. 351-354.

Sun, M., et al., "The influence of co-solvents on the stability and bioavailability of rapamycin formulated in self-microemulsifying drug delivery systems", *Drug Devel. & Industrial Pharma.*, 37(8), 986-994, 2011.

Swindle, K., et al., "Recent advances in polymeric vitreous substitutes", *Expert Rev. Opthalmol.*, 2(2), 255-265, 2007.

Vezina et al., "Rapamycin (AY-22,989), A New Antifungal Antibiotic. I. Taxonomy of the Producing Streptomycete and Isolation of the Active Principle", J. Antibiot. (Tokyo), 28, 1975, pp. 721-726.

Woo, H., et al., "Preclinical evaluation of injectable sirolimus formulated with polymeric nanoparticle for cancer therapy", *Int'l J. Nanomedicine*, vol. 7, Apr. 26, 2012, pp. 2197-2208.

International Preliminary Report on Patentability for PCT/US2017/068777, dated Jul. 2, 2019.

Official Communication issued in International Bureau of WIPO Patent Application No. PCT/US 18/67724, dated Mar. 26, 2019.

Office Action issued in Russia Counterpart Patent Appl. No. 201990127, dated Apr. 1, 2019, along with an English translation thereof.

DEPOT FORMULATIONS

CROSS-REFERENCE TO RELATED APPLICATIONS

This application claims priority to U.S. Provisional Application No. 62/356,613, filed Jun. 30, 2016, and to U.S. Provisional Application No. 62/440,658, filed Dec. 30, 2016. The disclosures of U.S. Provisional Application No. 62/356,613 and U.S. Provisional Application No. 62/440,658 are incorporated herein by reference.

FIELD OF THE INVENTION

The present disclosure relates to pharmaceutical depot formulations and uses thereof, including ophthalmic pharmaceutical depot formulations.

BACKGROUND

Certain ophthalmic conditions, such as uveitis, wet and dry age-related macular degeneration (AMD), diabetic macular edema (DME), diabetic retinopathy (DR) and keratomycosis, require long-term treatment. While drug treatments can be given systemically (e.g., orally), such treatment exposes the entire body to the drug, and is not able to focus the treatment on the area in greatest need of treatment. An ophthalmic depot formulation should be able to concentrate treatment on the area in need of treatment, while reducing systemic exposure of patients' bodies to the medication, and reducing frequency of administration.

However, ophthalmic depot formulations are more challenging to develop than other implants and depot formulations. An ophthalmic depot must minimize, or preferably completely avoid, affecting vision, but the eye has limited space, and may be sensitive to pressure and/or distortion. Thus an ophthalmic depot foimulation—whether, e.g., intrahumorous or subconjunctival—should be limited in physical size, i.e., volume. However, the depot formulation should at the same time contain enough active pharmaceutical ingredient (API) to avoid the need for frequent re-application (since application methods are typically invasive and inconvenient, e.g., by injection in a hospital or clinical setting).

With regard to intra-humorous (e.g., intra-vitreous) depots, because these are placed into fluid environments, it is also important for the depot to remain cohesive. A depot that is not cohesive can break up into many separate globules. These globules have a greater collective surface area than a cohesive depot, which can affect the rate of API release. A large number of globules also has the potential to adversely impact vision.

Implanted or injected formulations, such as ophthalmic (e.g., intra-vitreous) depots, are highly invasive, inconvenient, and may require administration by a healthcare professional. Therefore, it is usually considered advantageous for depot formulations to exhibit controlled or extended release after the pharmaceutical composition is administered to the patient, and which preferably exhibits continued drug efficacy over a long period.

There remains a long-felt need for improved depot formulations, including ophthalmic depot formulations and methods for treating ophthalmic conditions. For instance, there remains a long-felt need for sirolimus depot formulations and methods of use thereof for treating ophthalmic conditions. There remains a long-felt need for a depot formulation, including an ophthalmic depot formulation, capable of providing sustained release of an active ingredient. There remains a need for depot formulations, preferably ophthalmic depot formulations, which attain sustained release via a composition consisting essentially of an active pharmaceutical ingredient, a high viscosity liquid carrier material (HVLCM), a hydrophobic solvent; and a hydrophilic solvent, which composition preferably does not comprise other excipients materially affecting the rate or extent of the sustained release.

SUMMARY

Certain non-limiting aspects of the disclosure are provided below:

1. A composition comprising:
    an active pharmaceutical ingredient;
    a high viscosity liquid carrier material (HVLCM);
    a first hydrophobic solvent; and
    a hydrophilic solvent;
    wherein the composition is a solution at 25° C. and 1 atmosphere and/or wherein the composition has a viscosity ranging from about 1 cP to about 150 cP at 25° C. and 1 atmosphere.

2. A composition comprising:
    an active pharmaceutical ingredient;
    a high viscosity liquid carrier material (HVLCM), wherein the HVLCM is present in an amount ranging from about 0.5 wt % to about 15 wt %, based on weight of the composition;
    a first hydrophobic solvent, wherein the first hydrophobic solvent is present in an amount ranging from about 30 wt % to about 50 wt %, based on weight of the composition; and
    a hydrophilic solvent;
    wherein the composition is a solution at 25° C. and 1 atmosphere and/or wherein the composition has a viscosity ranging from about 1 cP to about 150 cP at 25° C. and 1 atmosphere.

3. A composition comprising:
    an active pharmaceutical ingredient;
    a high viscosity liquid carrier material (HVLCM), wherein the HVLCM is present in an amount ranging from about 0.5 wt % to about 15 wt %, based on weight of the composition;
    a first hydrophobic solvent, wherein the first hydrophobic solvent is present in an amount ranging from about 80 wt % to about 95 wt %, based on weight of the composition; and
    a hydrophilic solvent;
    wherein the composition is a solution at 25° C. and 1 atmosphere and/or wherein the composition has a viscosity ranging from about 1 cP to about 150 cP at 25° C. and 1 atmosphere.

4. A composition comprising:
    an active pharmaceutical ingredient, wherein the active pharmaceutical ingredient comprises sirolimus;
    a high viscosity liquid carrier material (HVLCM);
    a first hydrophobic solvent; and
    a hydrophilic solvent.

5. A composition comprising:
    an active pharmaceutical ingredient, wherein the active pharmaceutical ingredient comprises sirolimus;
    a high viscosity liquid carrier material (HVLCM), wherein the HVLCM is present in an amount ranging from about 0.5 wt % to about 15 wt %, based on weight of the composition;

a first hydrophobic solvent, wherein the first hydrophobic solvent is present in an amount ranging from about 30 wt % to about 50 wt %, based on weight of the composition; and
a hydrophilic solvent.
6. A composition comprising:
an active pharmaceutical ingredient, wherein the active pharmaceutical ingredient comprises sirolimus;
a high viscosity liquid carrier material (HVLCM), wherein the HVLCM is present in an amount ranging from about 0.5 wt % to about 15 wt %, based on weight of the composition;
a first hydrophobic solvent, wherein the first hydrophobic solvent is present in an amount ranging from about 80 wt % to about 95 wt %, based on weight of the composition; and
a hydrophilic solvent.
7. A composition comprising:
an active pharmaceutical ingredient;
a first hydrophobic solvent;
a second hydrophobic solvent different from the first hydrophobic solvent, the second hydrophobic solvent comprising at least one of a trialkyl citrate and an acetyl trialkyl citrate, wherein alkyl groups of each of the trialkyl citrate and the acetyl trialkyl citrate are the same or different, and have a number of carbon atoms of 3 to 5; and
a hydrophilic solvent.
8. A composition comprising:
an active pharmaceutical ingredient;
a polyalkylene glycol;
a first hydrophobic solvent; and
a hydrophilic solvent different from the polyalkylene glycol.
9. A composition comprising:
an active pharmaceutical ingredient, wherein the active pharmaceutical ingredient comprises sirolimus;
a polyalkylene glycol, wherein the polyalkylene glycol is present in an amount ranging from about 40 wt % to about 55 wt %;
a first hydrophobic solvent, wherein the first hydrophobic solvent is present in an amount ranging from about 30 wt % to about 50 wt %, based on weight of the composition; and
a hydrophilic solvent different from the polyalkylene glycol.
10. A composition comprising:
an active pharmaceutical ingredient;
a poloxamer;
a first hydrophobic solvent; and
a hydrophilic solvent.
11. A composition comprising:
an active pharmaceutical ingredient;
an antioxidant;
a first hydrophobic solvent; and
a hydrophilic solvent.
12. A composition comprising:
an active pharmaceutical ingredient;
an antioxidant;
a first hydrophobic solvent, wherein the first hydrophobic solvent is present in an amount ranging from about 30 wt % to about 50 wt %, based on weight of the composition; and
a hydrophilic solvent.
13. A composition comprising:
an active pharmaceutical ingredient;
an antioxidant;
a first hydrophobic solvent, wherein the first hydrophobic solvent is present in an amount ranging from about 80 wt % to about 95 wt %, based on weight of the composition; and
a hydrophilic solvent.
14. The composition of any one of aspects 7 to 13, wherein the composition further comprises a high viscosity liquid carrier material (HVLCM).
15. The composition of any one of aspects 1, 4, and 14, wherein the HVLCM is present in an amount ranging from about 0.1 wt % to about 50 wt %, based on weight of the composition.
16. The composition of any one of aspects 1, 4, and 14, wherein the HVLCM is present in an amount ranging from about 0.5 wt % to about 50 wt %, based on weight of the composition.
17. The composition of any one of aspects 1, 4, and 14, wherein the HVLCM is present in an amount ranging from about 30 wt % to about 60 wt %, based on weight of the composition.
18. The composition of aspect 15, wherein the HVLCM is present in an amount ranging from about 40 wt % to about 50 wt %, based on weight of the composition.
19. The composition of aspect 15, wherein the HVLCM is present in an amount ranging from about 1 wt % to about 20 wt %, based on weight of the composition.
20. The composition of aspect 19, wherein the HVLCM is present in an amount ranging from about 5 wt % to about 15 wt %, based on weight of the composition.
21. The composition of aspect 15, wherein the HVLCM is present in an amount ranging from about 0.1 wt % to about 10 wt %, based on weight of the composition.
22. The composition of any one of aspects 1 to 6 and 14, wherein the HVLCM is present in an amount ranging from about 0.8 wt % to about 10 wt %, based on weight of the composition.
23. The composition of any one of aspects 1 to 6 and 14, wherein the HVLCM is present in an amount ranging from about 0.5 wt % to about 5 wt %, based on weight of the composition.
24. The composition of any one of aspects 1 to 6 and 14 to 23, wherein the HVLCM comprises sucrose acetate isobutyrate (SAIB).
25. The composition of any one of aspects 1 to 24, wherein the composition comprises from about 1 wt % to about 10 wt % of the active pharmaceutical ingredient, based on weight of the composition.
26. The composition of aspect 25, wherein the composition comprises from about 1 wt % to about 5 wt % of the active pharmaceutical ingredient, based on weight of the composition.
27. The composition of any one of aspects 1 to 26, wherein the active pharmaceutical ingredient comprises an antibiotic.
28. The composition of any one of aspects 1 to 3, 7, 8, and 10 to 27, wherein the active pharmaceutical ingredient comprises sirolimus.
29. The composition of any one of aspects 1 to 28, wherein the active pharmaceutical ingredient comprises a substance other than sirolimus.
30. The composition of any one of aspects 1 to 28, wherein the active pharmaceutical ingredient does not comprise an ophthalmic drug other than sirolimus.
31. The composition of any one of aspects 1 to 30, wherein the first hydrophobic solvent is present in an amount ranging from about 10 wt % to about 95 wt %, based on weight of the composition.

32. The composition of aspect 31, wherein the first hydrophobic solvent is present in an amount ranging from about 30 wt % to about 60 wt %, based on weight of the composition.
33. The composition of aspect 32, wherein the first hydrophobic solvent is present in an amount ranging from about 40 wt % to about 50 wt %, based on weight of the composition.
34. The composition of any one of aspects 1 to 31, wherein the first hydrophobic solvent is present in an amount ranging from about 35 wt % to about 55 wt %, based on weight of the composition.
35. The composition of aspect 34, wherein the first hydrophobic solvent is present in an amount ranging from about 35 wt % to about 50 wt %, based on weight of the composition.
36. The composition of aspect 35, wherein the first hydrophobic solvent is present in an amount ranging from about 35 wt % to about 45 wt %, based on weight of the composition.
37. The composition of aspect 31, wherein the first hydrophobic solvent is present in an amount ranging from about 80 wt % to about 95 wt %, based on weight of the composition.
38. The composition of any one of aspects 1 to 37 wherein the first hydrophobic solvent comprises at least one of methyl benzoate, ethyl benzoate, n-propyl benzoate, isopropyl benzoate, butyl benzoate, isobutyl benzoate, sec-butyl benzoate, tert-butyl benzoate, isoamyl benzoate, and benzyl benzoate.
39. The composition of any one of aspects 1 to 38, wherein the first hydrophobic solvent comprises benzyl benzoate.
40. The composition of any one of aspects 1 to 39, wherein the first hydrophobic solvent does not comprise 1,1,1,2 tetrafluoroethane.
41. The composition of any one of aspects 1 to 39, wherein the first hydrophobic solvent does not comprise a fluorinated hydrocarbon.
42. The composition of any one of aspects 1 to 39, wherein the first hydrophobic solvent does not comprise a propellant.
43. The composition of any one of aspects 1 to 42, wherein the hydrophilic solvent is present in an amount ranging from about 1 wt % to about 70 wt %, based on weight of the composition.
44. The composition of any one of aspects 1 to 42, wherein the hydrophilic solvent is present in an amount ranging from about 2 wt % to about 60 wt %, based on weight of the composition.
45. The composition of aspect 43, wherein the hydrophilic solvent is present in an amount ranging from about 1 wt % to about 10 wt %, based on weight of the composition.
46. The composition of any one of aspects 1 to 45, wherein the hydrophilic solvent is present in an amount less than 10 wt %, based on weight of the composition.
47. The composition of aspect 46, wherein the hydrophilic solvent is present in an amount ranging from about 1 wt % to about 7 wt %, based on weight of the composition.
48. The composition of any one of aspects 1 to 47, wherein the hydrophilic solvent is present in an amount less than 5 wt %, based on weight of the composition.
49. The composition of any one of aspects 1 to 48, wherein the hydrophilic solvent comprises at least one of ethanol, triethyl acetyl citrate (ATEC), dimethylsulfoxide (DMSO), N-methyl pyrrolidone (NMP), propylene glycol, dimethyl acetamide (DMA), and polyethylene glycol (PEG).
50. The composition of any one of aspects 1 to 49, wherein the hydrophilic solvent comprises ethanol.
51. The composition of any one of aspects 1 to 49, wherein the hydrophilic solvent comprises ATEC.
52. The composition of any one of aspects 1 to 51, wherein the hydrophilic solvent comprises at least ethanol and ATEC.
53. The composition of any one of aspects 1 to 52, wherein the hydrophilic solvent comprises PEG.
54. The composition of any one of aspects 1 to 7 and 10 to 49, wherein the hydrophilic solvent comprises at least ethanol and PEG.
55. The composition of any one of aspects 1 to 7 and 10 to 54, wherein the hydrophilic solvent is present in an amount ranging from about 3 wt % to about 55 wt %, based on weight of the composition.
56. The composition of any one of aspects 50, 52, 54 and 55, wherein the ethanol is present in an amount ranging from about 1 wt % to about 10 wt %, based on weight of the composition.
57. The composition of any one of aspects 50, 52, 54 and 56, wherein the ethanol is present in an amount ranging from about 3 wt % to about 10 wt %, based on weight of the composition.
58. The composition of any one of aspects 53 to 57, wherein the PEG is present in an amount ranging from about 30 wt % to about 60 wt %, based on weight of the composition.
59. The composition of aspect 58, wherein the PEG is present in an amount ranging from about 35 wt % to about 50 wt %, based on weight of the composition.
60. The composition of aspect 58, wherein the PEG is present in an amount ranging from about 40 wt % to about 55 wt %, based on weight of the composition.
61. The composition of aspect 59, wherein the PEG is present in an amount ranging from about 40 wt % to about 50 wt %, based on weight of the composition.
62. The composition of any one of aspects 1 to 6 and 8 to 61, further comprising a trialkyl citrate and/or acetyl trialkyl citrate, wherein alkyl groups of each of the trialkyl citrate and the acetyl trialkyl citrate are the same or different, and have a number of carbon atoms of 3 to 5.
63. The composition of aspect 7 or 62, wherein the trialkyl citrate and/or acetyl trialkyl citrate is present in an amount ranging from about 10 wt % to about 95 wt %, based on weight of the composition.
64. The composition of aspect 7 or 62, wherein the trialkyl citrate and/or acetyl trialkyl citrate is present in an amount ranging from about 35 wt % to about 65 wt %, based on weight of the composition.
65. The composition of aspect 7 or 62, wherein the trialkyl citrate and/or acetyl trialkyl citrate is present in an amount ranging from about 30 wt % to about 60 wt %, based on weight of the composition.
66. The composition of aspect 65, wherein the trialkyl citrate and/or acetyl trialkyl citrate is present in an amount ranging from about 40 wt % to about 50 wt %, based on weight of the composition.
67. The composition of any one of aspects 7 and 62 to 66, wherein the number of carbon atoms of the alkyl group of the trialkyl citrate and/or acetyl trialkyl citrate is 4.
68. The composition of any one of aspects 7 and 62 to 67, wherein the trialkyl citrate is tri-n-butyl citrate, and the acetyl trialkyl citrate is acetyl tri-n-butyl citrate.
69. The composition of any one of aspects 7 and 62 to 67, wherein the trialkyl citrate and/or acetyl trialkyl citrate comprises acetyl tri-n-butyl citrate.
70. The composition of any one of aspects 1 to 69, wherein the composition comprises water.

71. The composition of any one of aspects 1 to 70, wherein the composition comprises less than 1 wt % of water.
72. The composition of any one of aspects 1 to 70, wherein the composition comprises less than 0.5 wt % of water.
73. The composition of any one of aspects 1 to 7 and 11 to 52, 55 to 57, and 62 to 72, wherein the composition is polymer-free apart from the active pharmaceutical ingredient which optionally comprises a polymer.
74. The composition of any one of aspects 1 to 72, wherein the composition includes at least one of polyalkylene glycol and poloxamer, and wherein the composition is otherwise polymer-free apart from the active pharmaceutical ingredient which optionally comprises a polymer.
75. The composition of any one of aspects 1 to 72, further comprising a polymer.
76. The composition of aspect 75, wherein the polymer is present in an amount ranging from about 0.1 wt % to about 30 wt %, based on weight of the composition.
77. The composition of aspect 75 or 76, wherein the polymer comprises a polyester.
78. The composition of any one of aspects 75 to 77, wherein the polymer comprises at least one of poly(lactic acid) (glycolic acid), poly(lactic acid), and polycaprolactone.
79. The composition of any one of aspects 1 to 78, further comprising a surfactant.
80. The composition of any one of aspects 1 to 78, further comprising at least one member selected from poloxamer, polyethoxylated castor oil, polyoxyethylated hydroxystearic acid, sorbitan monooleate, and sorbitan monolaurate.
81. The composition of aspect 80, wherein the at least one member is present in an amount ranging from about 0.1 wt % to about 10 wt %, based on weight of the composition.
82. The composition of any one of aspects 1 to 81, further comprising triethyl citrate.
83. The composition of any one of aspects 1 to 82, further comprising ascorbyl palmitate.
84. The composition of any one of aspects 1 to 9, 11 to 72, and 75 to 83, further comprising poloxamer.
85. The composition of aspect 10 or 84, wherein the poloxamer is present in an amount ranging from about 0.5 wt % to about 10 wt %.
86. The composition of aspect 10 or 84, wherein the poloxamer is present in an amount ranging from about 0.5 wt % to about 2 wt %.
87. The composition of aspect 10 or 84, wherein the poloxamer is present in an amount ranging from about 0.1 wt % to about 5 wt %.
88. The composition of any one of aspects 1 to 87, further comprising an acid precursor.
89. The composition of any one of aspects 1 to 88, wherein at least 98% of the active pharmaceutical ingredient in the composition remains after storage in a 2 ml crimp sealed glass vial for 18 weeks at 5° C./60% RH.
90. The composition of any one of aspects 1 to 89, wherein at least 90% of the active pharmaceutical ingredient in the composition remains after storage in a 2 ml crimp sealed glass vial for 18 weeks at 25° C./60% RH.
91. The composition of any one of aspects 1 to 10 and 14 to 90, wherein the composition further comprises an antioxidant.
92. The composition of any one of aspects 11 to 13 and 91, wherein the antioxidant is present in an amount ranging from about 0.5 wt % to about 5 wt %, based on weight of the composition.
93. The composition of any one of aspects 11 to 13, 91 and 92, wherein the antioxidant comprises vitamin E.
94. The composition of aspect 93, wherein the vitamin E is present in an amount ranging from about 1 wt % to about 50 wt %, based on weight of the composition.
95. The composition of any one of aspects 93 and 94, wherein the vitamin E is present in an amount less than 10 wt %, based on weight of the composition.
96. The composition of aspect 95, wherein the vitamin E is present in an amount ranging from about 0.1 wt % to about 5 wt %, based on weight of the composition.
97. The composition of any one of aspects 11 to 13 and 93 to 96, wherein the vitamin E is present in an amount of less than 5 wt %, based on weight of the composition.
98. The composition of aspect 97, wherein the vitamin E is present in an amount ranging from about 0.5 wt % to about 2 wt %, based on weight of the composition.
99. The composition of aspect 93, wherein a weight ratio of HVLCM to vitamin E ranges from about 60:1 to about 1:2.
100. The composition of aspect 93, wherein a weight ratio of HVCLM to vitamin E ranges from about 10:1 to about 1:1.8.
101. The composition of aspect 93, wherein a weight ratio of HVLCM to vitamin E ranges from about 5:1 to about 1:1.5.
102. The composition of aspect 93, wherein a weight ratio of HVLCM to vitamin E ranges from about 2:1 to about 1:1.5.
103. The composition of aspect 99, wherein the HVLCM comprises SAIB.
104. The composition of aspect 100, wherein the HVLCM comprises SAIB.
105. The composition of aspect 101, wherein the HVLCM comprises SAIB.
106. The composition of aspect 102, wherein the HVLCM comprises SAIB.
107. The composition of aspect 93, wherein the composition comprises SAIB, and the composition has a weight ratio of SAIB:vitamin E ranging from about 0.5 to about 10.
108. The composition of any one of aspects 93 to 107, wherein the weight ratio of HVLCM to vitamin E is such that the density, at 25° C. and 1 atm, of a mixture consisting of said HVLCM and said vitamin E in said weight ratio is at least 1 g/ml.
109. The composition of aspect 108, wherein said density is at least 1.05 g/ml.
110. The composition of any one of aspects 1 to 109, wherein the composition further comprises a lipidic ester.
111. The composition of any one of aspects 1 to 110, wherein the composition further comprises a fatty ester.
112. The composition of any one of aspects 1 to 111, wherein the composition further comprises at least one of lauryl lactate and lauryl glycol.
113. The composition of any one of aspects 1 to 112, wherein the composition has a density at 25° C. and 1 atmosphere ranging from 1.02 g/ml to 1.15 g/ml.
114. The composition of any one of aspects 1 to 113, wherein the composition has a viscosity ranging from about 1 cP to about 150 cP at 25° C. and 1 atmosphere.
115. The composition of any one of aspects 1 to 113, wherein the composition has a viscosity ranging from about 5 cP to about 50 cP at 25° C. and 1 atmosphere.
116. The composition of any one of aspects 1 to 113, wherein the composition has a viscosity ranging from about 10 cP to about 30 cP at 25° C. and 1 atmosphere.
117. The composition of any one of aspects 1 to 116, wherein the composition is other than an emulsion.
118. The composition of any one of aspects 1 to 117, wherein the % cumulative release of the active pharmaceutical ingredient from the composition is less than 50% at T=24 hr when assayed by injecting 100 μL of the composition in 5 mL of release medium consisting of phosphate buffered saline with 0.1 wt % sodium dodecyl sulfate to form a sample, and placing the sample on an orbital shaker rotating at 30 rpm at 37° C.

119. The composition of any one of aspects 1 to 118, wherein the active pharmaceutical ingredient comprises sirolimus, and wherein the hydrophilic solvent comprises ethanol.

120. The composition of aspect 119, wherein the HVLCM comprises sucrose acetate isobutyrate.

121. The composition of aspect 119 or 120, wherein the first hydrophobic solvent comprises benzyl benzoate.

122. The composition of any one of aspects 119 to 121, comprising vitamin E.

123. The composition of any one of aspects 119 to 122, comprising acetyl tri-n-butyl citrate.

124. The composition of aspect 4, wherein the active pharmaceutical ingredient is present in an amount ranging from about 1 wt % to about 10 wt %, based on weight of the composition;
the HVLCM is present in an amount ranging from about 30 wt % to about 60 wt %, based on weight of the composition;
the HVLCM comprises SAIB;
the first hydrophobic solvent is present in an amount ranging from about 30 wt % to about 60 wt %, based on weight of the composition;
the first hydrophobic solvent comprises benzyl benzoate;
the hydrophilic solvent is present in an amount ranging from about 1 wt % to about 10 wt %, based on weight of the composition;
the hydrophilic solvent comprises ethanol;
the composition further comprises vitamin E; and
the vitamin E is present in an amount ranging from about 0.1 wt % to about 5 wt %, based on weight of the composition.

125. The composition of aspect 124, wherein the SAIB comprises sucrose esterified with two acetic acid and six isobutyric acid moieties.

126. The composition of aspect 125, wherein the sucrose esterified with two acetic acid and six isobutyric acid moieties is present in an amount ranging from 7 wt % to about 15 wt %, based on weight of the composition.

127. The composition of any one of aspects 124 to 126, further comprising poloxamer, wherein the poloxamer is present in an amount ranging from about 0.1 wt % to about 5 wt %, based on weight of the composition.

128. The composition of aspect 4, wherein the active pharmaceutical ingredient is present in an amount ranging from about 1 wt % to about 10 wt %, based on weight of the composition;
the HVLCM is present in an amount ranging from about 1 wt % to about 20 wt %, based on weight of the composition;
the HVLCM comprises SAIB;
the first hydrophobic solvent is present in an amount ranging from about 30 wt % to about 60 wt %, based on weight of the composition;
the first hydrophobic solvent comprises benzyl benzoate;
the hydrophilic solvent comprises at least ethanol and PEG;
the ethanol is present in an amount ranging from about 1 wt % to about 10 wt %, based on weight of the composition;
the PEG is present in an amount ranging from about 30 wt % to about 60 wt %, based on weight of the composition;
the composition further comprises vitamin E; and
the vitamin E is present in an amount ranging from about 0.1 wt % to about 5 wt %, based on weight of the composition.

129. The composition of aspect 128, wherein the SAIB comprises sucrose esterified with two acetic acid and six isobutyric acid moieties.

130. The composition of aspect 129, wherein the sucrose esterified with two acetic acid and six isobutyric acid moieties is present in an amount ranging from about 0.25 wt % to about 5 wt %, based on weight of the composition.

131. The composition of aspect 4, wherein the active pharmaceutical ingredient is present in an amount ranging from about 1 wt % to about 10 wt %, based on weight of the composition;
the HVLCM is present in an amount ranging from about 0.1 wt % to about 10 wt %, based on weight of the composition;
the HVLCM comprises SAIB;
the first hydrophobic solvent is present in an amount ranging from about 30 wt % to about 60 wt %, based on weight of the composition;
the first hydrophobic solvent comprises benzyl benzoate;
the hydrophilic solvent comprises at least ethanol and PEG;
the ethanol is present in an amount ranging from about 1 wt % to about 10 wt %, based on weight of the composition;
the PEG is present in an amount ranging from about 30 wt % to about 60 wt %, based on weight of the composition;
the composition further comprises vitamin E; and
the vitamin E is present in an amount ranging from about 0.1 wt % to about 5 wt %, based on weight of the composition.

132. The composition of any one of aspects 1 to 131, wherein:
the active pharmaceutical ingredient comprises sirolimus in an amount ranging from about 1 wt % to about 5 wt %, based on weight of the composition;
the HVLCM comprises sucrose acetate isobutyrate (SAIB) in an amount ranging from about 0.1 wt % to about 10 wt %, based on weight of the composition;
the first hydrophobic solvent comprises benzyl benzoate in an amount ranging from about 30 wt % to about 45 wt %, based on weight of the composition;
the hydrophilic solvent comprises (i) ethanol in an amount ranging from about 1 wt % to about 10 wt %, based on weight of the composition; and (ii) PEG in an amount ranging from about 40 wt % to about 50 wt %, based on weight of the composition; and
the composition further comprises vitamin E in an amount ranging from about 0.5 wt % to about 2 wt %, based on weight of the composition.

133. The composition of any one of aspects 1 to 132, the composition consisting essentially of:
sirolimus in an amount ranging from about 1 wt % to about 5 wt %, based on weight of the composition;
SAIB in an amount ranging from about 0.1 wt % to about 10 wt %, based on weight of the composition;
benzyl benzoate in an amount ranging from about 30 wt % to about 45 wt %, based on weight of the composition;

ethanol in an amount ranging from about 1 wt % to about 10 wt %, based on weight of the composition;
PEG400 in an amount ranging from about 40 wt % to about 50 wt %, based on weight of the composition; and
vitamin E in an amount ranging from about 0.5 wt % to about 2 wt %, based on weight of the composition.

134. The composition of any one of aspects 1 to 133, the composition consisting essentially of:
sirolimus in an amount ranging from about 1 wt % to about 5 wt %, based on weight of the composition;
SAIB in an amount not exceeding about 10 wt %, based on weight of the composition; benzyl benzoate;
the hydrophilic solvent selected from the group consisting of ethanol and PEG400; and
vitamin E in an amount ranging from about 0.5 wt % to about 2 wt %, wherein a weight ratio of SAIB to vitamin E exceeds about 0.5.

135. The composition of any one of aspects 131 to 134, wherein the SAIB comprises sucrose esterified with two acetic acid and six isobutyric acid moieties.

136. The composition of aspect 135, wherein the sucrose esterified with two acetic acid and six isobutyric acid moieties is present in an amount ranging from about 0.025 wt % to about 2.5 wt %, based on weight of the composition.

137. The composition of aspect 4, wherein the active pharmaceutical ingredient is present in an amount ranging from about 1 wt % to about 10 wt %, based on weight of the composition;
the HVLCM is present in an amount ranging from about 0.1 wt % to about 10 wt %, based on weight of the composition;
the HVLCM comprises SAIB;
the first hydrophobic solvent is present in an amount ranging from about 80 wt % to about 95 wt %, based on weight of the composition;
the first hydrophobic solvent comprises benzyl benzoate;
the hydrophilic solvent comprises at least ethanol;
the ethanol is present in an amount ranging from about 1 wt % to about 10 wt %, based on weight of the composition;
the composition further comprises vitamin E; and
the vitamin E is present in an amount ranging from about 0.1 wt % to about 5 wt %, based on weight of the composition.

138. The composition of aspect 137, wherein the SAIB comprises sucrose esterified with two acetic acid and six isobutyric acid moieties.

139. The composition of aspect 138, wherein the sucrose esterified with two acetic acid and six isobutyric acid moieties is present in an amount ranging from about 0.025 wt % to about 2.5 wt %, based on weight of the composition.

140. The composition of aspect 7, wherein the active pharmaceutical ingredient is present in an amount ranging from about 1 wt % to about 10 wt %, based on weight of the composition;
the active pharmaceutical ingredient comprises sirolimus;
the composition further comprising a high viscosity liquid carrier material (HVLCM) present in an amount ranging from about 0.1 wt % to about 10 wt %, based on weight of the composition;
the HVLCM comprises SAIB;
the first hydrophobic solvent is present in an amount ranging from about 30 wt % to about 60 wt %, based on weight of the composition;
the first hydrophobic solvent comprises benzyl benzoate;
the second hydrophobic solvent is present in an amount ranging from about 30 wt % to about 60 wt %, based on weight of the composition;
the second hydrophobic solvent comprises acetyl tri-n-butyl citrate (ATBC);
the hydrophilic solvent is present in an amount ranging from about 1 wt % to about 10 wt %, based on weight of the composition;
the hydrophilic solvent comprises ethanol;
the composition further comprises vitamin E; and
the vitamin E is present in an amount ranging from about 0.1 wt % to about 5 wt %, based on weight of the composition.

141. The composition of aspect 140, wherein the SAIB comprises sucrose esterified with two acetic acid and six isobutyric acid moieties.

142. The composition of aspect 141, wherein the sucrose esterified with two acetic acid and six isobutyric acid moieties is present in an amount ranging from about 0.025 wt % to about 2.5 wt %, based on weight of the composition.

143. The composition of aspect 4, wherein the active pharmaceutical ingredient is present in an amount ranging from about 1 wt % to about 5 wt %, based on weight of the composition;
the HVLCM is present in an amount ranging from about 40 wt % to about 50 wt %, based on weight of the composition;
the HVLCM comprises SAIB;
the first hydrophobic solvent is present in an amount ranging from about 40 wt % to about 50 wt %, based on weight of the composition;
the first hydrophobic solvent comprises benzyl benzoate;
the hydrophilic solvent is present in an amount ranging from about 1 wt % to about 7 wt %, based on weight of the composition;
the hydrophilic solvent comprises ethanol;
the composition further comprises vitamin E; and
the vitamin E is present in an amount ranging from about 0.5 wt % to about 2 wt %, based on weight of the composition.

144. The composition of aspect 143, wherein the SAIB comprises sucrose esterified with two acetic acid and six isobutyric acid moieties.

145. The composition of aspect 144, wherein the sucrose esterified with two acetic acid and six isobutyric acid moieties is present in an amount ranging from about 10 wt % to about 13 wt %, based on weight of the composition.

146. The composition of aspect 143, wherein the amount of the active pharmaceutical ingredient present therein is about 3 wt %, based on weight of the composition;
the amount of the HVLCM present therein is about 47.5 wt %, based on weight of the composition;
the amount of the first hydrophobic solvent present therein is about 43.7 wt %, based on weight of the composition;
the amount of the ethanol present therein is about 4.8 wt %, based on weight of the composition; and
the amount of the vitamin E present therein is about 1 wt %, based on weight of the composition.

147. The composition of aspect 146, wherein the SAIB comprises sucrose esterified with two acetic acid and six isobutyric acid moieties.

148. The composition of aspect 147, wherein the sucrose esterified with two acetic acid and six isobutyric acid moieties is present in an amount of about 12 wt %, based on weight of the composition.

149. The composition of aspect 4, wherein the active pharmaceutical ingredient is present in an amount ranging from about 1 wt % to about 5 wt %, based on weight of the composition;
 the HVLCM is present in an amount ranging from about 5 wt % to about 15 wt %, based on weight of the composition;
 the HVLCM comprises SAIB;
 the first hydrophobic solvent is present in an amount ranging from about 35 wt % to about 45 wt %, based on weight of the composition;
 the first hydrophobic solvent comprises benzyl benzoate;
 the hydrophilic solvent comprises at least ethanol and PEG;
 the ethanol is present in an amount ranging from about 1 wt % to about 10 wt %, based on weight of the composition;
 the PEG is present in an amount ranging from about 35 wt % to about 50 wt %, based on weight of the composition;
 the composition further comprises vitamin E; and
 the vitamin E is present in an amount ranging from about 0.5 wt % to about 2 wt %, based on weight of the composition.

150. The composition of aspect 149, wherein the SAIB comprises sucrose esterified with two acetic acid and six isobutyric acid moieties.

151. The composition of aspect 150, wherein the sucrose esterified with two acetic acid and six isobutyric acid moieties is present in an amount ranging from about 1 wt % to about 4 wt %, based on weight of the composition.

152. The composition of aspect 149, wherein the amount of the active pharmaceutical ingredient present therein is about 3 wt %, based on weight of the composition;
 the amount of the HVLCM present therein is about 9.7 wt %, based on weight of the composition;
 the amount of the first hydrophobic solvent present therein is about 38.8 wt %, based on weight of the composition;
 the amount of the ethanol present therein is about 4.8 wt %, based on weight of the composition;
 the amount of the PEG present therein is about 42.7 wt %, based on weight of the composition; and
 the amount of the vitamin E therein is about 1 wt %, based on weight of the composition.

153. The composition of aspect 152, wherein the SAIB comprises sucrose esterified with two acetic acid and six isobutyric acid moieties.

154. The composition of aspect 153, wherein the sucrose esterified with two acetic acid and six isobutyric acid moieties is present in an amount of about 2.5 wt %, based on weight of the composition.

155. The composition of aspect 4, wherein the active pharmaceutical ingredient is present in an amount ranging from about 1 wt % to about 5 wt %, based on weight of the composition;
 the HVLCM is present in an amount ranging from about 0.5 wt % to about 5 wt %, based on weight of the composition;
 the HVLCM comprises SAIB;
 the first hydrophobic solvent is present in an amount ranging from about 35 wt % to about 50 wt %, based on weight of the composition;
 the first hydrophobic solvent comprises benzyl benzoate;
 the hydrophilic solvent comprises at least ethanol and PEG;
 the ethanol is present in an amount ranging from about 1 wt % to about 10 wt %, based on weight of the composition;
 the PEG is present in an amount ranging from about 40 wt % to about 50 wt %, based on weight of the composition;
 the composition further comprises vitamin E; and
 the vitamin E is present in an amount ranging from about 0.5 wt % to about 2 wt %, based on weight of the composition.

156. The composition of aspect 155, wherein the SAIB comprises sucrose esterified with two acetic acid and six isobutyric acid moieties.

157. The composition of aspect 156, wherein the sucrose esterified with two acetic acid and six isobutyric acid moieties is present in an amount ranging from about 0.1 wt % to about 1 wt %, based on weight of the composition.

158. The composition of aspect 155, wherein the amount of the active pharmaceutical ingredient present therein is about 3 wt %, based on weight of the composition;
 the amount of the HVLCM present therein is about 1 wt %, based on weight of the composition;
 the amount of the first hydrophobic solvent present therein is about 43.7 wt %, based on weight of the composition;
 the amount of the ethanol present therein is about 4.8 wt %, based on weight of the composition;
 the amount of the PEG present therein is about 46.5 wt %, based on weight of the composition; and
 the amount of the vitamin E therein is about 1 wt %, based on weight of the composition.

159. The composition of aspect 158, wherein the SAIB comprises sucrose esterified with two acetic acid and six isobutyric acid moieties.

160. The composition of aspect 159, wherein the sucrose esterified with two acetic acid and six isobutyric acid moieties is present in an amount of about 0.25 wt %, based on weight of the composition.

161. The composition of aspect 4, wherein the active pharmaceutical ingredient is present in an amount ranging from about 1 wt % to about 5 wt %, based on weight of the composition;
 the HVLCM is present in an amount ranging from about 0.5 wt % to about 5 wt %, based on weight of the composition;
 the HVLCM comprises SAIB;
 the first hydrophobic solvent is present in an amount ranging from about 80 wt % to about 95 wt %, based on weight of the composition;
 the first hydrophobic solvent comprises benzyl benzoate;
 the hydrophilic solvent comprises at least ethanol;
 the ethanol is present in an amount ranging from about 1 wt % to about 10 wt %, based on weight of the composition;
 the composition further comprises vitamin E; and
 the vitamin E is present in an amount ranging from about 0.5 wt % to about 2 wt %, based on weight of the composition.

162. The composition of aspect 161, wherein the SAIB comprises sucrose esterified with two acetic acid and six isobutyric acid moieties.

163. The composition of aspect 162, wherein the sucrose esterified with two acetic acid and six isobutyric acid moieties is present in an amount ranging from about 0.1 wt % to about 1 wt %, based on weight of the composition.

164. The composition of aspect 7, wherein the active pharmaceutical ingredient is present in an amount ranging from about 1 wt % to about 5 wt %, based on weight of the composition; the composition further comprising a high viscosity liquid carrier material (HVLCM) present in an amount ranging from about 0.5 wt % to about 5 wt %, based on weight of the composition;
the HVLCM comprises SAIB;
the first hydrophobic solvent is present in an amount ranging from about 35 wt % to about 50 wt %, based on weight of the composition;
the first hydrophobic solvent comprises benzyl benzoate;
the second hydrophobic solvent is present in an amount ranging from about 40 wt % to about 50 wt %, based on weight of the composition;
the second hydrophobic solvent comprises acetyl tri-n-butyl citrate (ATBC);
the hydrophilic solvent comprises ethanol;
the ethanol is present in an amount ranging from about 1 wt % to about 10 wt %, based on weight of the composition;
the composition further comprises vitamin E; and
the vitamin E is present in an amount ranging from about 0.5 wt % to about 2 wt %, based on weight of the composition.
165. The composition of aspect 164, wherein the SAIB comprises sucrose esterified with two acetic acid and six isobutyric acid moieties.
166. The composition of aspect 165, wherein the sucrose esterified with two acetic acid and six isobutyric acid moieties is present in an amount ranging from about 0.1 wt % to about 1 wt %, based on weight of the composition.
167. The composition of aspect 164, wherein the amount of the active pharmaceutical ingredient present therein is about 3 wt %, based on weight of the composition;
the amount of the HVLCM present therein is about 1 wt %, based on weight of the composition;
the amount of the first hydrophobic solvent present therein is about 43.7 wt %, based on weight of the composition;
the amount of the second hydrophilic solvent present therein is about 46.5 wt %, based on weight of the composition;
the amount of the ethanol present therein is about 4.8 wt %, based on weight of the composition; and
the amount of the vitamin E therein is about 1 wt %, based on weight of the composition.
168. The composition of aspect 167, wherein the SAIB comprises sucrose esterified with two acetic acid and six isobutyric acid moieties.
169. The composition of aspect 168, wherein the sucrose esterified with two acetic acid and six isobutyric acid moieties is present in an amount of about 0.25 wt %, based on weight of the composition.
170. The composition of any one of aspects 1 to 169, wherein:
the active pharmaceutical ingredient comprises sirolimus in an amount ranging from about 1 wt % to about 5 wt %, based on weight of the composition;
the HVLCM comprises sucrose acetate isobutyrate (SAIB) in an amount ranging from about 0.1 wt % to about 10 wt %, based on weight of the composition;
the first hydrophobic solvent comprises benzyl benzoate in an amount ranging from about 80 wt % to about 95 wt %, based on weight of the composition;
the hydrophilic solvent comprises ethanol in an amount ranging from about 1 wt % to about 10 wt %, based on weight of the composition; and
the composition further comprises vitamin E in an amount ranging from about 0.5 wt % to about 2 wt %, based on weight of the composition.
171. The composition of any one of aspects 1 to 170, the composition consisting essentially of:
sirolimus in an amount ranging from about 1 wt % to about 5 wt %, based on weight of the composition;
SAIB in an amount ranging from about 0.1 wt % to about 10 wt %, based on weight of the composition;
benzyl benzoate in an amount ranging from about 80 wt % to about 95 wt %, based on weight of the composition;
ethanol in an amount ranging from about 1 wt % to about 10 wt %, based on weight of the composition; and
vitamin E in an amount ranging from about 0.5 wt % to about 2 wt %, based on weight of the composition.
172. The composition of aspect 170 or 171, wherein the SAIB comprises sucrose esterified with two acetic acid and six isobutyric acid moieties.
173. The composition of aspect 172, wherein the sucrose esterified with two acetic acid and six isobutyric acid moieties is present in an amount ranging from about 0.025 wt % to about 1 wt %, based on weight of the composition.
174. The composition of aspect 4, wherein the amount of the active pharmaceutical ingredient present therein is about 3 wt %, based on weight of the composition;
the HVLCM comprises SAIB present at about 2 wt %, based on weight of the composition;
the first hydrophobic solvent comprises benzyl benzoate present at about 42.7 wt %, based on weight of the composition;
the hydrophilic solvent comprises PEG present at about 46.5 wt %, based on weight of the composition;
the hydrophilic solvent further comprises ethanol present at about 4.8 wt %, based on weight of the composition; and
the composition further comprising vitamin E present at about 1 wt %, based on weight of the composition.
175. The composition of aspect 4, wherein the amount of the active pharmaceutical ingredient present therein is about 3 wt %, based on weight of the composition;
the HVLCM comprises SAIB present at about 3 wt %, based on weight of the composition;
the first hydrophobic solvent comprises benzyl benzoate present at about 41.7 wt %, based on weight of the composition;
the hydrophilic solvent comprises PEG present at about 46.5 wt %, based on weight of the composition;
the hydrophilic solvent further comprises ethanol present at about 4.8 wt %, based on weight of the composition; and
the composition further comprising vitamin E present at about 1 wt %, based on weight of the composition.
176. The composition of aspect 4, wherein the amount of the active pharmaceutical ingredient present therein is about 3 wt %, based on weight of the composition;
the HVLCM comprises SAIB present at about 4 wt %, based on weight of the composition;
the first hydrophobic solvent comprises benzyl benzoate present at about 40.7 wt %, based on weight of the composition;
the hydrophilic solvent comprises PEG present at about 46.5 wt %, based on weight of the composition;
the hydrophilic solvent further comprises ethanol present at about 4.8 wt %, based on weight of the composition; and the composition further comprising vitamin E present at about 1 wt %, based on weight of the composition.

177. The composition of aspect 4, wherein the amount of the active pharmaceutical ingredient present therein is about 3 wt %, based on weight of the composition;
the HVLCM comprises SAIB present at about 4.9 wt %, based on weight of the composition;
the first hydrophobic solvent comprises benzyl benzoate present at about 39.8 wt %, based on weight of the composition;
the hydrophilic solvent comprises PEG present at about 46.5 wt %, based on weight of the composition;
the hydrophilic solvent further comprises ethanol present at about 4.8 wt %, based on weight of the composition; and
the composition further comprising vitamin E present at about 1 wt %, based on weight of the composition.

178. The composition of aspect 4, wherein the amount of the active pharmaceutical ingredient present therein is about 3 wt %, based on weight of the composition;
the HVLCM comprises SAIB present at about 5.9 wt %, based on weight of the composition;
the first hydrophobic solvent comprises benzyl benzoate present at about 38.8 wt %, based on weight of the composition;
the hydrophilic solvent comprises PEG present at about 46.5 wt %, based on weight of the composition;
the hydrophilic solvent further comprises ethanol present at about 4.8 wt %, based on weight of the composition; and
the composition further comprising vitamin E present at about 1 wt %, based on weight of the composition.

179. The composition of aspect 4, wherein the amount of the active pharmaceutical ingredient present therein is about 3 wt %, based on weight of the composition;
the HVLCM comprises SAIB present at about 6.8 wt %, based on weight of the composition;
the first hydrophobic solvent comprises benzyl benzoate present at about 37.9 wt %, based on weight of the composition;
the hydrophilic solvent comprises PEG present at about 46.5 wt %, based on weight of the composition;
the hydrophilic solvent further comprises ethanol present at about 4.8 wt %, based on weight of the composition; and
the composition further comprising vitamin E present at about 1 wt %, based on weight of the composition.

180. The composition of aspect 4, wherein the amount of the active pharmaceutical ingredient present therein is about 3 wt %, based on weight of the composition;
the HVLCM comprises SAIB present at about 7.8 wt %, based on weight of the composition;
the first hydrophobic solvent comprises benzyl benzoate present at about 36.9 wt %, based on weight of the composition;
the hydrophilic solvent comprises PEG present at about 46.5 wt %, based on weight of the composition;
the hydrophilic solvent further comprises ethanol present at about 4.8 wt %, based on weight of the composition; and
the composition further comprising vitamin E present at about 1 wt %, based on weight of the composition.

181. The composition of aspect 4, wherein the amount of the active pharmaceutical ingredient present therein is about 3 wt %, based on weight of the composition;
the HVLCM comprises SAIB present at about 8.8 wt %, based on weight of the composition;
the first hydrophobic solvent comprises benzyl benzoate present at about 35.9 wt %, based on weight of the composition;
the hydrophilic solvent comprises PEG present at about 46.5 wt %, based on weight of the composition;
the hydrophilic solvent further comprises ethanol present at about 4.8 wt %, based on weight of the composition; and
the composition further comprising vitamin E present at about 1 wt %, based on weight of the composition.

182. The composition of aspect 4, wherein the amount of the active pharmaceutical ingredient present therein is about 3 wt %, based on weight of the composition;
the HVLCM comprises SAIB present at about 9.7 wt %, based on weight of the composition;
the first hydrophobic solvent comprises benzyl benzoate present at about 35 wt %, based on weight of the composition;
the hydrophilic solvent comprises PEG present at about 46.5 wt %, based on weight of the composition;
the hydrophilic solvent further comprises ethanol present at about 4.8 wt %, based on weight of the composition; and
the composition further comprising vitamin E present at about 1 wt %, based on weight of the composition.

183. The composition of aspect 4, wherein the amount of the active pharmaceutical ingredient present therein is about 3 wt %, based on weight of the composition;
the HVLCM comprises SAIB present at about 1 wt %, based on weight of the composition;
the first hydrophobic solvent comprises benzyl benzoate present at about 90.2 wt %, based on weight of the composition;
the hydrophilic solvent comprises ethanol present at about 4.8 wt %, based on weight of the composition; and
the composition further comprising vitamin E present at about 1 wt %, based on weight of the composition.

184. The composition of aspect 4, wherein the amount of the active pharmaceutical ingredient present therein is about 3 wt %, based on weight of the composition;
the HVLCM comprises SAIB present at about 2 wt %, based on weight of the composition;
the first hydrophobic solvent comprises benzyl benzoate present at about 89.2 wt %, based on weight of the composition;
the hydrophilic solvent comprises ethanol present at about 4.8 wt %, based on weight of the composition; and
the composition further comprising vitamin E present at about 1 wt %, based on weight of the composition.

185. The composition of aspect 4, wherein the amount of the active pharmaceutical ingredient present therein is about 3 wt %, based on weight of the composition;
the HVLCM comprises SAIB present at about 2.9 wt %, based on weight of the composition;
the first hydrophobic solvent comprises benzyl benzoate present at about 88.3 wt %, based on weight of the composition;
the hydrophilic solvent comprises ethanol present at about 4.8 wt %, based on weight of the composition; and
the composition further comprising vitamin E present at about 1 wt %, based on weight of the composition.

186. The composition of aspect 4, wherein the amount of the active pharmaceutical ingredient present therein is about 3 wt %, based on weight of the composition;
the HVLCM comprises SAIB present at about 3.9 wt %, based on weight of the composition;

the first hydrophobic solvent comprises benzyl benzoate present at about 87.3 wt %, based on weight of the composition;
the hydrophilic solvent comprises ethanol present at about 4.8 wt %, based on weight of the composition; and
the composition further comprising vitamin E present at about 1 wt %, based on weight of the composition.

187. The composition of aspect 4, wherein the amount of the active pharmaceutical ingredient present therein is about 3 wt %, based on weight of the composition;
the HVLCM comprises SAIB present at about 4.9 wt %, based on weight of the composition;
the first hydrophobic solvent comprises benzyl benzoate present at about 86.3 wt %, based on weight of the composition;
the hydrophilic solvent comprises ethanol present at about 4.8 wt %, based on weight of the composition; and
the composition further comprising vitamin E present at about 1 wt %, based on weight of the composition.

188. The composition of aspect 4, wherein the amount of the active pharmaceutical ingredient present therein is about 3 wt %, based on weight of the composition;
the HVLCM comprises SAIB present at about 5.8 wt %, based on weight of the composition;
the first hydrophobic solvent comprises benzyl benzoate present at about 85.4 wt %, based on weight of the composition;
the hydrophilic solvent comprises ethanol present at about 4.8 wt %, based on weight of the composition; and
the composition further comprising vitamin E present at about 1 wt %, based on weight of the composition.

189. The composition of aspect 4, wherein the amount of the active pharmaceutical ingredient present therein is about 3 wt %, based on weight of the composition;
the HVLCM comprises SAIB present at about 6.8 wt %, based on weight of the composition;
the first hydrophobic solvent comprises benzyl benzoate present at about 84.4 wt %, based on weight of the composition;
the hydrophilic solvent comprises ethanol present at about 4.8 wt %, based on weight of the composition; and
the composition further comprising vitamin E present at about 1 wt %, based on weight of the composition.

190. The composition of aspect 4, wherein the amount of the active pharmaceutical ingredient present therein is about 3 wt %, based on weight of the composition;
the HVLCM comprises SAIB present at about 7.8 wt %, based on weight of the composition;
the first hydrophobic solvent comprises benzyl benzoate present at about 83.4 wt %, based on weight of the composition;
the hydrophilic solvent comprises ethanol present at about 4.8 wt %, based on weight of the composition; and
the composition further comprising vitamin E present at about 1 wt %, based on weight of the composition.

191. The composition of aspect 4, wherein the amount of the active pharmaceutical ingredient present therein is about 3 wt %, based on weight of the composition;
the HVLCM comprises SAIB present at about 8.7 wt %, based on weight of the composition;
the first hydrophobic solvent comprises benzyl benzoate present at about 82.5 wt %, based on weight of the composition;
the hydrophilic solvent comprises ethanol present at about 4.8 wt %, based on weight of the composition; and
the composition further comprising vitamin E present at about 1 wt %, based on weight of the composition.

192. The composition of aspect 4, wherein the amount of the active pharmaceutical ingredient present therein is about 3 wt %, based on weight of the composition;
the HVLCM comprises SAIB present at about 9.7 wt %, based on weight of the composition;
the first hydrophobic solvent comprises benzyl benzoate present at about 81.5 wt %, based on weight of the composition;
the hydrophilic solvent comprises ethanol present at about 4.8 wt %, based on weight of the composition; and
the composition further comprising vitamin E present at about 1 wt %, based on weight of the composition.

193. A composition comprising:
an active pharmaceutical ingredient, wherein the active pharmaceutical ingredient comprises sirolimus;
means for extending a release profile of the pharmaceutical active ingredient when the composition is administered to a patient in need thereof.

194. The composition of any one of aspects 1 to 193, wherein when the composition is administered as a single dose intra-ocularly to a rabbit, the composition provides a median release profile of pharmaceutically active ingredient within ±20% of the release profile of C908 of FIG. 13.

195. The composition of aspect 194, wherein the single dose comprises 30 μL.

196. The composition of any of aspects 194 or 195, wherein the active pharmaceutical ingredient comprises 0.9 mg sirolimus.

197. The composition of any one of aspects 1 to 196, wherein when the composition is administered intra-ocularly as a single dose to a rabbit, a median amount of pharmaceutical active ingredient released from the composition at 1 month after administration ranges from 1% to 20% or 2% to 15% of a total amount of the pharmaceutical active ingredient in the composition at the time of administration.

198. The composition of any one of aspects 1 to 197, wherein when the composition is administered intra-ocularly as a single dose to a rabbit, a median amount of pharmaceutical active ingredient released from the composition at 3 months after administration ranges from 10% to 60% or 20% to 50% of a total amount of the pharmaceutical active ingredient in the composition at the time of administration.

199. The composition of any one of aspects 1 to 198, wherein when the composition is administered intra-ocularly as a single dose to a rabbit, a median amount of pharmaceutical active ingredient released from the composition at 6 months after administration ranges from 30% to 100% or 40% to 90% of a total amount of the pharmaceutical active ingredient in the composition at the time of administration.

200. The composition of any one of aspects 1 to 199, wherein when the composition is placed in phosphate buffered saline with 0.1% (w/v) sodium dodecyl sulfate at 37° C., an amount of pharmaceutical active ingredient released from the composition at 1 day of placement in the phosphate buffered saline ranges from 5% to 50% or 10% to 40% of a total amount of the pharmaceutical active ingredient in the composition.

201. The composition of aspect 200, wherein the placed composition comprises 75 μL.

202. The composition of any of aspects 200 or 201, wherein the active pharmaceutical ingredient comprises 3 wt %, based on weight of the composition.

203. The composition of any one of aspects 1 to 202, wherein when the composition is placed in phosphate buffered saline with 0.1% (w/v) SDS at 37° C., an amount of pharmaceutical active ingredient released from the composition at 5 days of placement in the phosphate buffered saline ranges from 5% to 75% or 10% to 50% of a total amount of the pharmaceutical active ingredient in the composition.

204. The composition of any one of aspects 1 to 203, wherein when the composition is placed in phosphate buffered saline with 0.1% (w/v) SDS at 37° C., an amount of pharmaceutical active ingredient released from the composition at 10 days of placement in the phosphate buffered saline ranges from 5% to 85% or 15% to 60% of a total amount of the pharmaceutical active ingredient in the composition.

205. The composition of any one of aspects 1 to 204, containing the components in a ratio sufficient to maintain a therapeutically effective concentration of the active pharmaceutical ingredient for a period of at least 3 months when the composition is administered intra-ocularly as a single dose to a human patient.

206. The composition of any one of aspects 1 to 205, containing the components in a ratio sufficient to maintain a therapeutically effective retina-choroid concentration of the active pharmaceutical ingredient for a period of at least 3 months when the composition is administered intra-ocularly as a single dose to a human patient.

207. The composition of any one of aspects 1 to 206, the composition comprising SAIB and vitamin E, the composition having a weight ratio of SAIB:vitamin E ranging from about 0.5 to about 20.

208. The composition of any one of aspects 1 to 207, wherein the composition is pharmaceutically acceptable.

209. The composition of any one of aspects 1 to 208, wherein the composition is formulated for injection.

210. The composition of any one of aspects 1 to 209, which comprises
sirolimus in an amount of about 3 wt %, based on weight of the composition
SAIB in an amount of about 1 wt %, based on weight of the composition;
benzyl benzoate in an amount of about 43.7 wt %, based on weight of the composition;
ethanol in an amount of about 4.8 wt %, based on weight of the composition;
PEG400 present in an amount of about 46.5 wt %, based on weight of the composition; and
vitamin E in an amount of about 1 wt %, based on weight of the composition.

211. A method of treating a subject afflicted with an eye condition, the method comprising:
administering a composition to an eye of a subject in need thereof, wherein the composition comprises an effective amount of an active pharmaceutical ingredient capable of treating the eye condition, the composition comprising:
an active pharmaceutical ingredient;
a high viscosity liquid carrier material (HVLCM);
a first hydrophobic solvent; and
a hydrophilic solvent.

212. A method of treating a subject afflicted with an eye condition, the method comprising:
administering a composition to an eye of a subject in need thereof, wherein the composition comprises an effective amount of an active pharmaceutical ingredient capable of treating the eye condition, the composition comprising:
an active pharmaceutical ingredient;
a high viscosity liquid carrier material (HVLCM), wherein the HVLCM is present in an amount ranging from about 0.5 wt % to about 15 wt %, based on weight of the composition;
a first hydrophobic solvent, wherein the first hydrophobic solvent is present in an amount ranging from about 30 wt % to about 50 wt %, based on weight of the composition; and
a hydrophilic solvent.

213. A method of treating a subject afflicted with an eye condition, the method comprising:
administering a composition to an eye of a subject in need thereof, wherein the composition comprises an effective amount of an active pharmaceutical ingredient capable of treating the eye condition, the composition comprising:
an active pharmaceutical ingredient;
a high viscosity liquid carrier material (HVLCM), wherein the HVLCM is present in an amount ranging from about 0.5 wt % to about 15 wt %, based on weight of the composition;
a first hydrophobic solvent, wherein the first hydrophobic solvent is present in an amount ranging from about 80 wt % to about 95 wt %, based on weight of the composition; and
a hydrophilic solvent.

214. A method of treating a subject afflicted with an eye condition, the method comprising:
administering the composition of any one of aspects 1 to 210 to an eye of a subject in need thereof, wherein the composition comprises an effective amount of an active pharmaceutical ingredient capable of treating the eye condition.

215. The method of any one of aspects 211 to 214, wherein the eye condition comprises uveitis, diabetic macular edema, or wet age-related macular degeneration.

216. The method of any one of aspects 211 to 214, wherein the eye condition comprises uveitis or wet age-related macular degeneration.

217. The method of any one of aspects 211 to 216, wherein the administering comprises injecting.

218. The method of aspect 217, wherein up to 50 µl of the composition is injected.

219. The method of aspect 217, wherein about 20 µl to about 30 µl of the composition is injected.

220. The method of any one of aspects 211 to 219, wherein the composition is injected with a needle having a size ranging from 27 G to 30 G.

221. The method of any one of aspects 211 to 220, wherein the composition is injected with a needle having a length ranging from about 1 cm to about 3 cm.

222. The method of any one of aspects 211 to 221, wherein at least 20% of the total amount of active pharmaceutical ingredient administered remains in the vitreous of the subject three months after the composition is injected into the vitreous of the subject.

223. A method of treating a subject afflicted with an eye condition, the method comprising:
administering the composition of any one of aspects 1 to 210 to the vitreous of a subject in need thereof, wherein the composition comprises an effective amount of an active pharmaceutical ingredient capable of treating the eye condition.

224. A method comprising:
administering to a patient a composition as defined in any one of aspects 1 to 210, wherein the composition provides a median release profile of pharmaceutically active ingredient within ±20% of the release profile of C908 of FIG. 13.

225. The method of aspect 224, which is a method as defined in any one of aspects 211 to 223.

226. The method of any one of aspects 211 to 225, wherein the composition is administered intra-ocularly as a single dose to a human patient and a median amount of pharmaceutical active ingredient released from the composition at 1 month after administration ranges from 1% to 20% or 2% to 15% of a total amount of the pharmaceutical active ingredient in the composition at the time of administration.

227. The method of any one of aspects 211 to 226, wherein the composition is administered intra-ocularly as a single dose to a human patient and a median amount of pharmaceutical active ingredient released from the composition at 3 months after administration to a human patient ranges from 10% to 60% or 20% to 50% of a total amount of the pharmaceutical active ingredient in the composition at the time of administration.

228. The method of any one of aspects 211 to 227, wherein the composition is administered intra-ocularly as a single dose to a human patient and a median amount of pharmaceutical active ingredient released from the composition at 6 months after administration ranges from 30% to 100% or 40% to 90% of a total amount of the pharmaceutical active ingredient in the composition at the time of administration.

229. The method of any one of aspects 211 to 228, wherein the composition comprises from 0.1 mg to 500 mg of the pharmaceutical active ingredient.

230. The method of any one of aspects 211 to 229, wherein a plasma Cmax of the pharmaceutical active ingredient ranges from 1 ng/mL to 10 ng/mL.

231. The method of any one of aspects 211 to 230, wherein a plasma Cmax of the pharmaceutical active ingredient is less than 10 ng/ml.

232. A composition as defined in any one of aspects 1 to 210 for use as a medicament.

233. A composition as defined in any one of aspects 1 to 210 for use in treatment of an eye condition, wherein the active pharmaceutical ingredient comprises an ophthalmic drug.

234. A composition for use of aspect 233, wherein the eye condition comprises uveitis, diabetic macular edema, or wet age-related macular degeneration.

235. A composition for use of aspect 233, wherein the eye condition comprises uveitis or wet age-related macular degeneration.

236. A composition for use of any one of aspects 232 to 235, wherein the active pharmaceutical ingredient comprises sirolimus.

237. The composition for use of any one of aspects 232 to 236, wherein the use comprises administering the composition intra-ocularly as a single dose to a human patient and a median amount of pharmaceutical active ingredient released from the composition at 1 month after administration ranges from 1% to 20% or 2% to 15% of a total amount of the pharmaceutical active ingredient in the composition at the time of administration.

238. The composition for use of any one of aspects 232 to 237, wherein the use comprises administering the composition intra-ocularly as a single dose to a human patient and a median amount of pharmaceutical active ingredient released from the composition at 3 months after administration ranges from 10% to 60% or 20% to 50% of a total amount of the pharmaceutical active ingredient in the composition at the time of administration.

239. The composition for use of any one of aspects 232 to 238, wherein the use comprises administering the composition intra-ocularly as a single dose to a human patient and a median amount of pharmaceutical active ingredient released from the composition at 6 months after administration to a human patient ranges from 30% to 100% or 40% to 90% of a total amount of the pharmaceutical active ingredient in the composition at the time of administration.

240. The composition for use of any one of aspects 232 to 239, wherein the composition comprises from 0.1 mg to 500 mg of the pharmaceutical active ingredient.

241. The composition for use of any one of aspects 232 to 240, wherein a plasma Cmax of the pharmaceutical active ingredient ranges from 1 ng/mL to 10 ng/mL.

242. The composition for use of any one of aspects 232 to 241, wherein a plasma Cmax of the pharmaceutical active ingredient is less than 10 ng/ml.

243. Use of the combination of components in a composition as defined in any one of aspects 1 to 210 or use of the composition for the manufacture of a medicament for the treatment of an eye condition, wherein the active pharmaceutical ingredient comprises an ophthalmic drug.

244. Use of aspect 243, wherein the eye condition comprises uveitis, diabetic macular edema, or wet age-related macular degeneration.

245. Use of aspect 243, wherein the eye condition comprises uveitis or wet age-related macular degeneration.

246. Use of any one of aspects 243 to 245, wherein the active pharmaceutical ingredient comprises sirolimus.

247. The use of any one of aspects 243 to 246, wherein the composition is administered intra-ocularly as a single dose to a human patient and a median amount of pharmaceutical active ingredient released from the composition at 1 month after administration ranges from 1% to 20% or 2% to 15% of a total amount of the pharmaceutical active ingredient in the composition at the time of administration.

248. The use of any one of aspects 243 to 247, wherein the composition is administered intra-ocularly as a single dose to a human patient and a median amount of pharmaceutical active ingredient released from the composition at 3 months after administration to a human patient ranges from 10% to 60% or 20% to 50% of a total amount of the pharmaceutical active ingredient in the composition at the time of administration.

249. The use of any one of aspects 243 to 248, wherein the composition is administered intra-ocularly as a single dose to a human patient and a median amount of pharmaceutical active ingredient released from the composition at 6 months after administration ranges from 30% to 100% or 40% to 90% of a total amount of the pharmaceutical active ingredient in the composition at the time of administration.

250. The use of any one of aspects 243 to 249, wherein the composition comprises from 0.1 mg to 500 mg of the pharmaceutical active ingredient.

251. The use of any one of aspects 243 to 250, wherein a plasma Cmax of the pharmaceutical active ingredient ranges from 1 ng/mL to 10 ng/mL.

252. The use of any one of aspects 243 to 251, wherein a plasma Cmax of the pharmaceutical active ingredient is less than 10 ng/ml.

253. A method for forming a depot, comprising bringing the composition of any one of aspects 1 to 210 into contact with water, a phosphate buffer solution, a body fluid or a simulated body fluid.

254. A method for forming a depot, comprising bringing the composition of any one of aspects 1 to 210 into contact with the vitreous humor of a subject.

255. A unit dosage form comprising the composition of any one of aspects 1 to 210, wherein the unit dosage form comprises from 0.4 mg to 1 mg of the pharmaceutical active ingredient.

256. The unit dosage form of aspect 255, wherein the composition is contained within a vial.

257. The unit dosage form of aspect 255, wherein the composition is contained within a syringe.

258. The unit dosage form of aspect 255, wherein the composition is contained within a needle-free injector.

259. A receptacle containing the composition of any one of aspects 1 to 210.

260. A needle-free injector comprising the composition of any one of aspects 1 to 210, wherein the composition comprises a pharmaceutical active ingredient.

BRIEF DESCRIPTIONS OF THE DRAWINGS

FIGS. 1a, 1b, and 1c show in vitro drug release from several compositions of the present disclosure.

Figure 9:
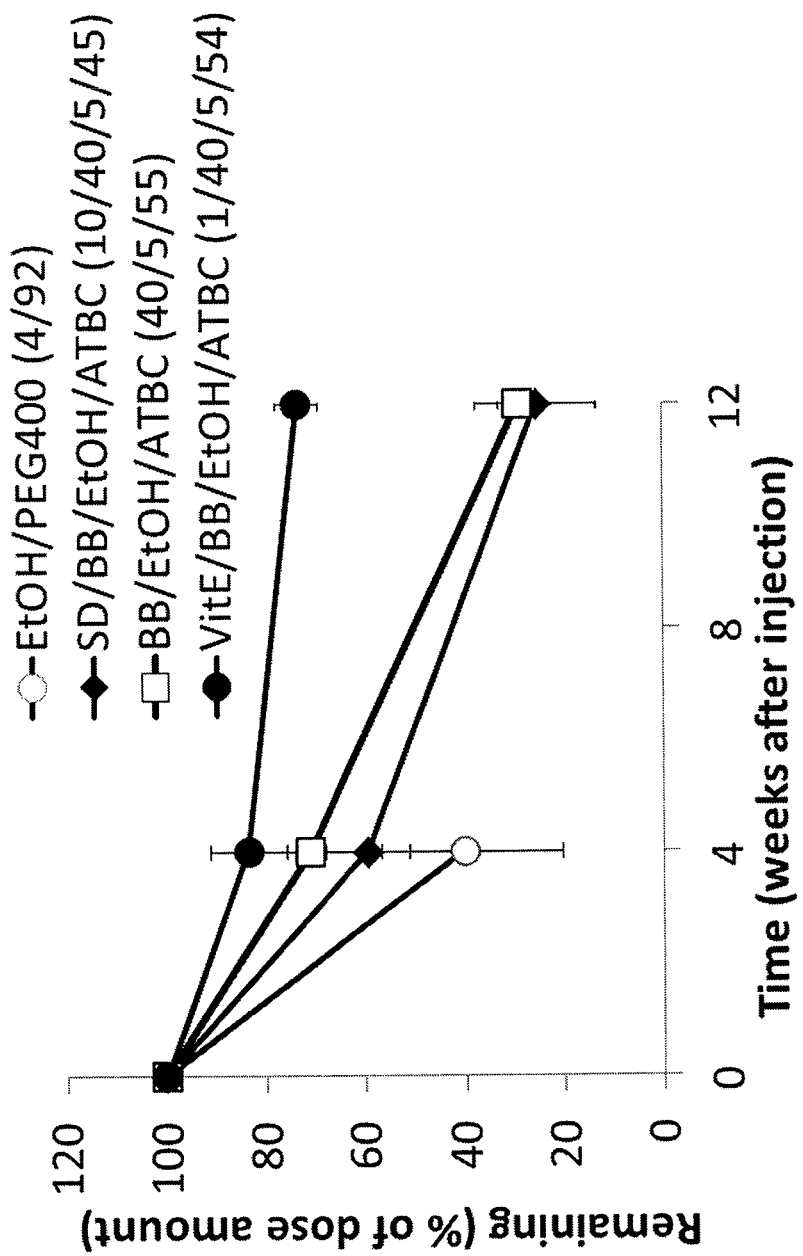

FIG. 9 shows the remaining dose amount in the intravitreal depot. Each point represents mean±SD (3-4 eyes). Time 0 is nominal value (100%).

Figure 10:
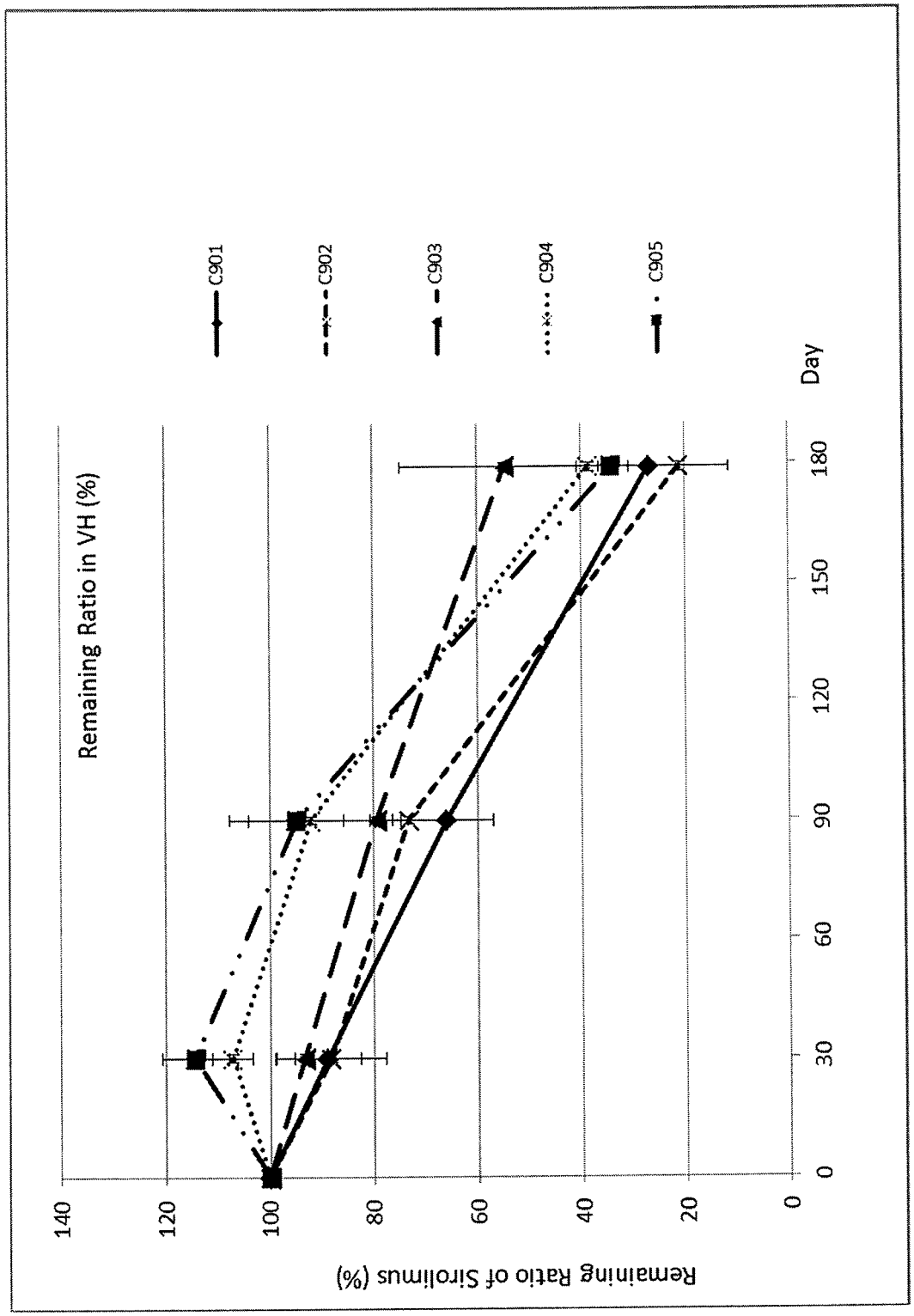

FIG. 10 shows sirolimus remaining in vitreous humor as described in more detail below in Example 9.

Figure 11:
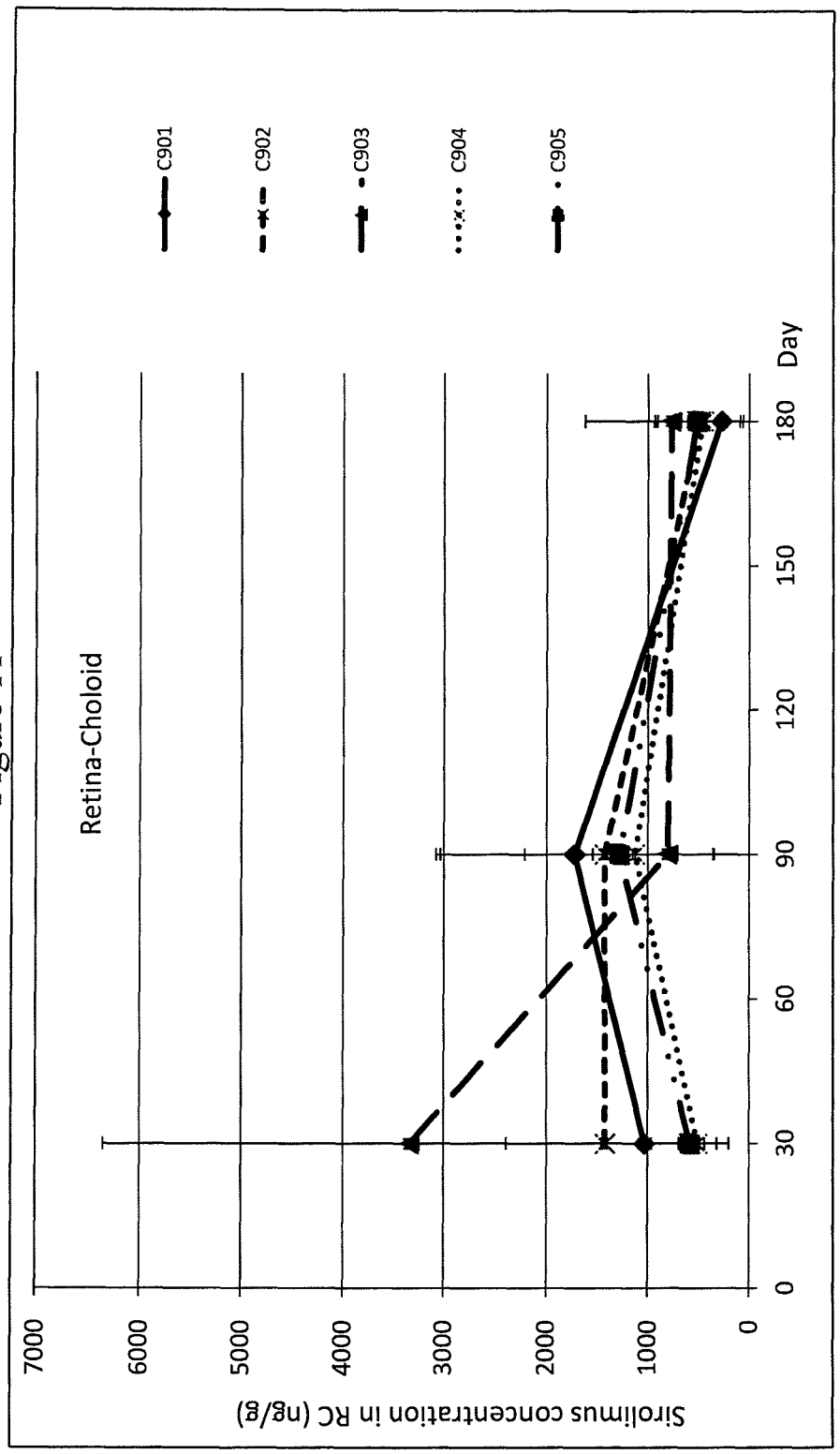

FIG. 11 shows sirolimus concentration in RC over time as described in more detail below in Example 9.

Figure 12:
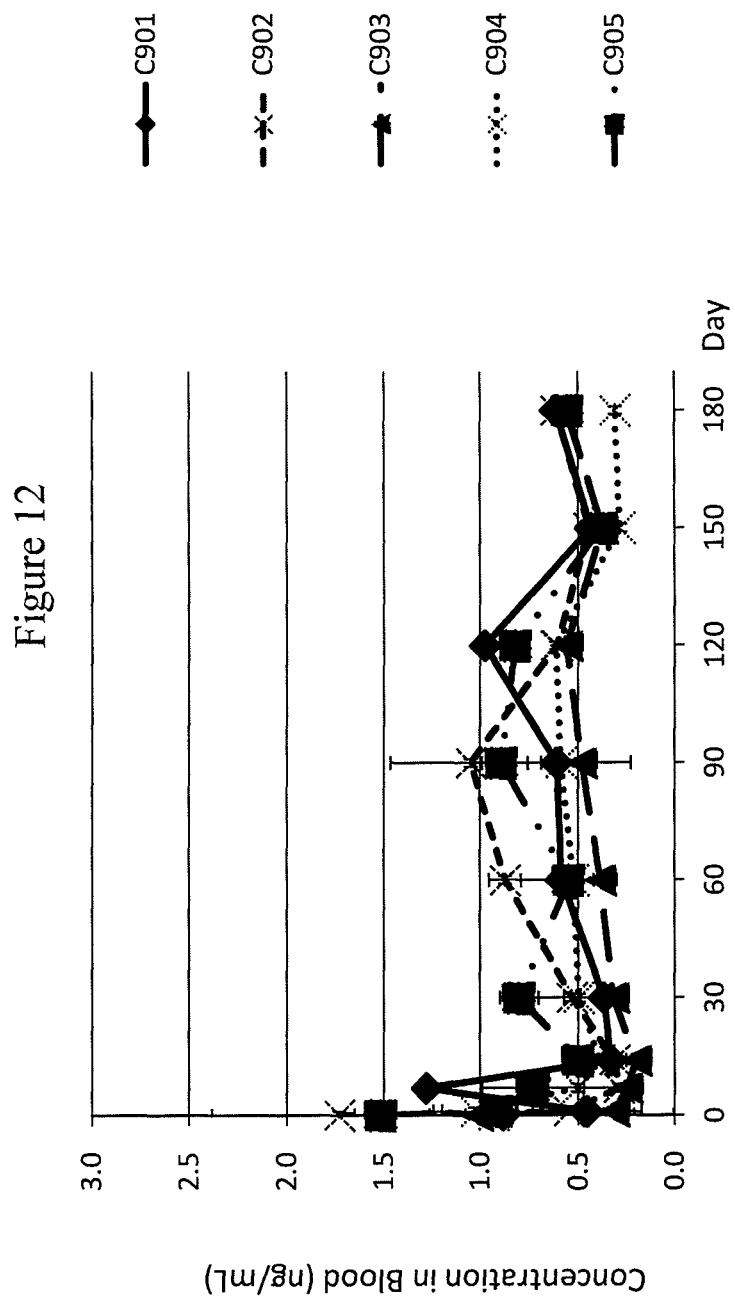

FIG. 12 shows sirolimus blood concentration after placement of intra vitreal depots as described in more detail below in Example 9.

Figure 13:
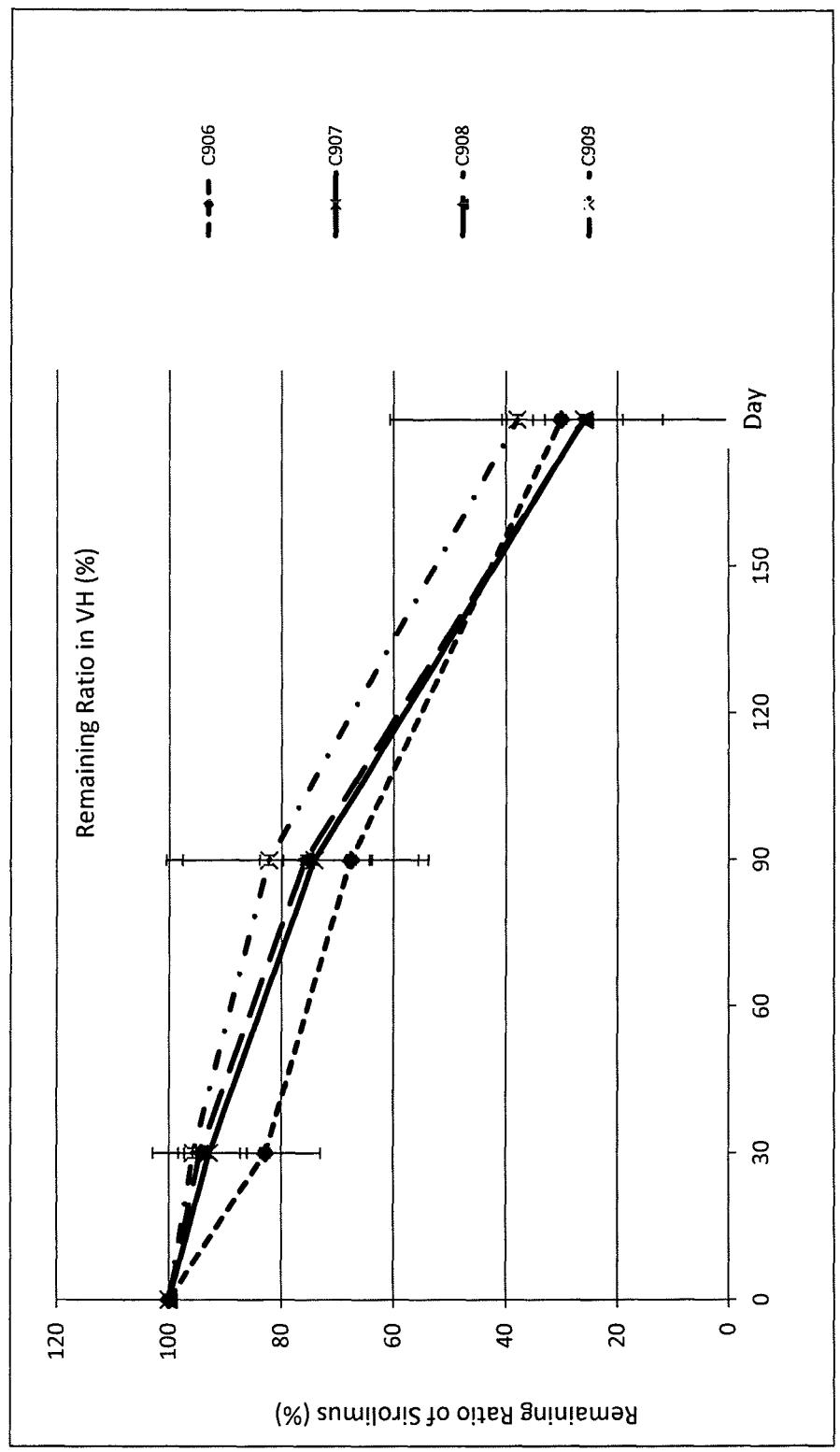

FIG. 13 shows sirolimus remaining in vitreous humor as described in more detail below in Example 10.

Figure 14:
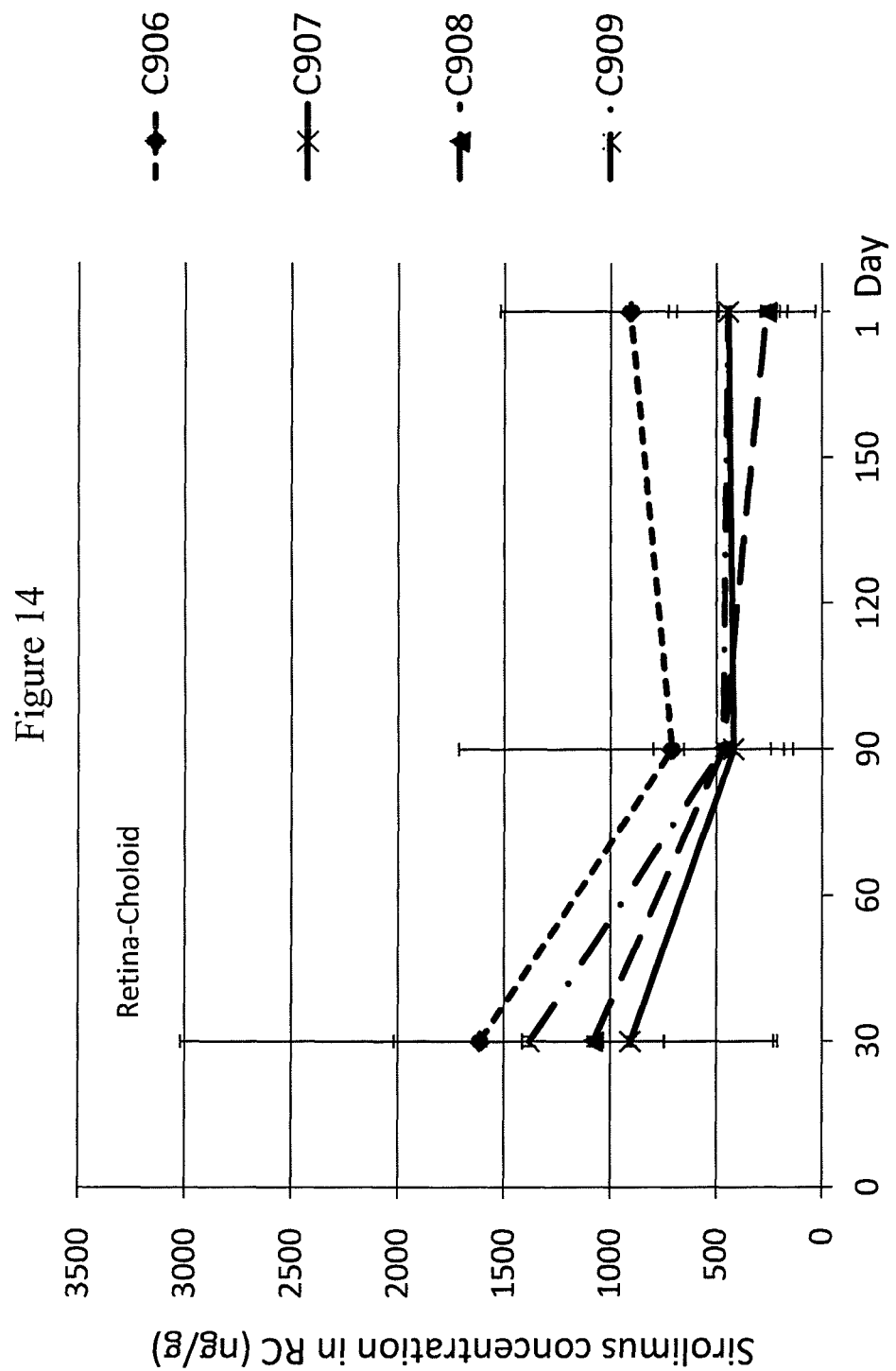

FIG. 14 shows sirolimus concentration in RC over time as described in more detail below in Example 10.

Figure 15:
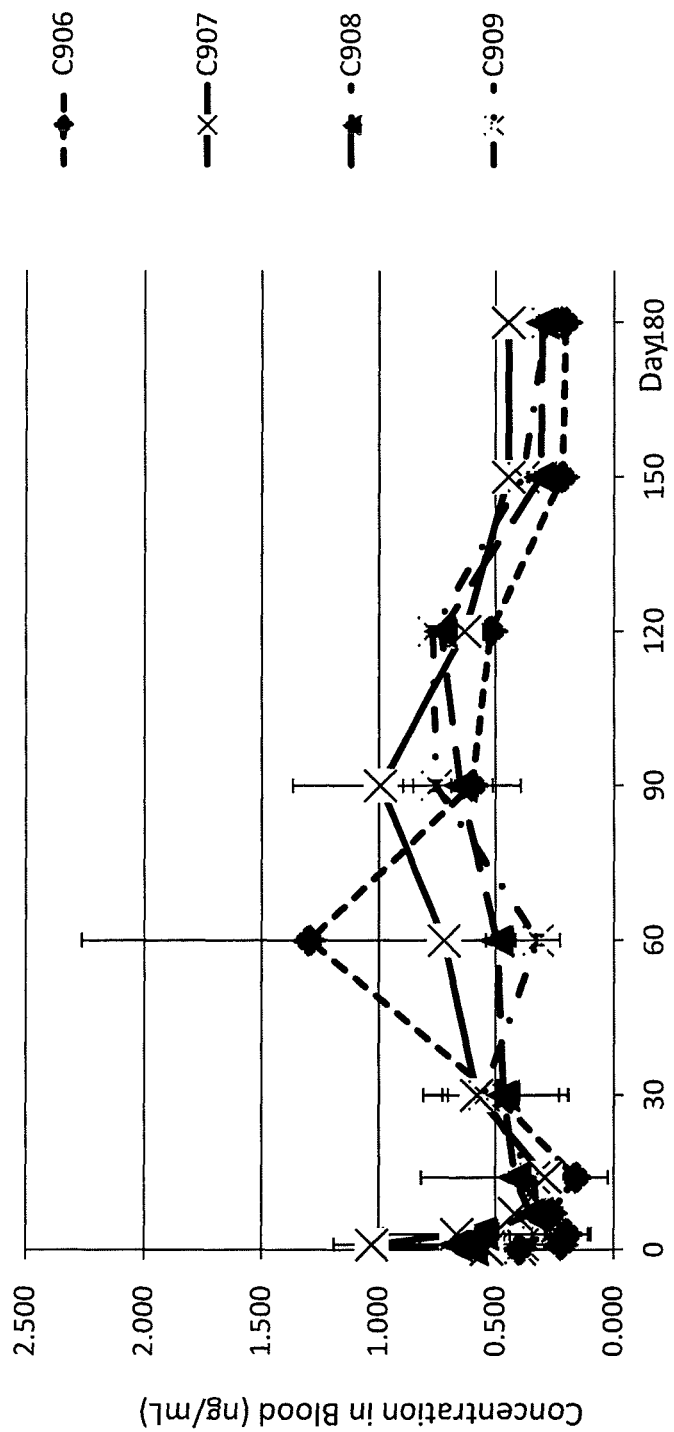

FIG. 15 shows sirolimus blood concentration after placement of intra vitreal depots as described in more detail below in Example 10.

Figure 16:
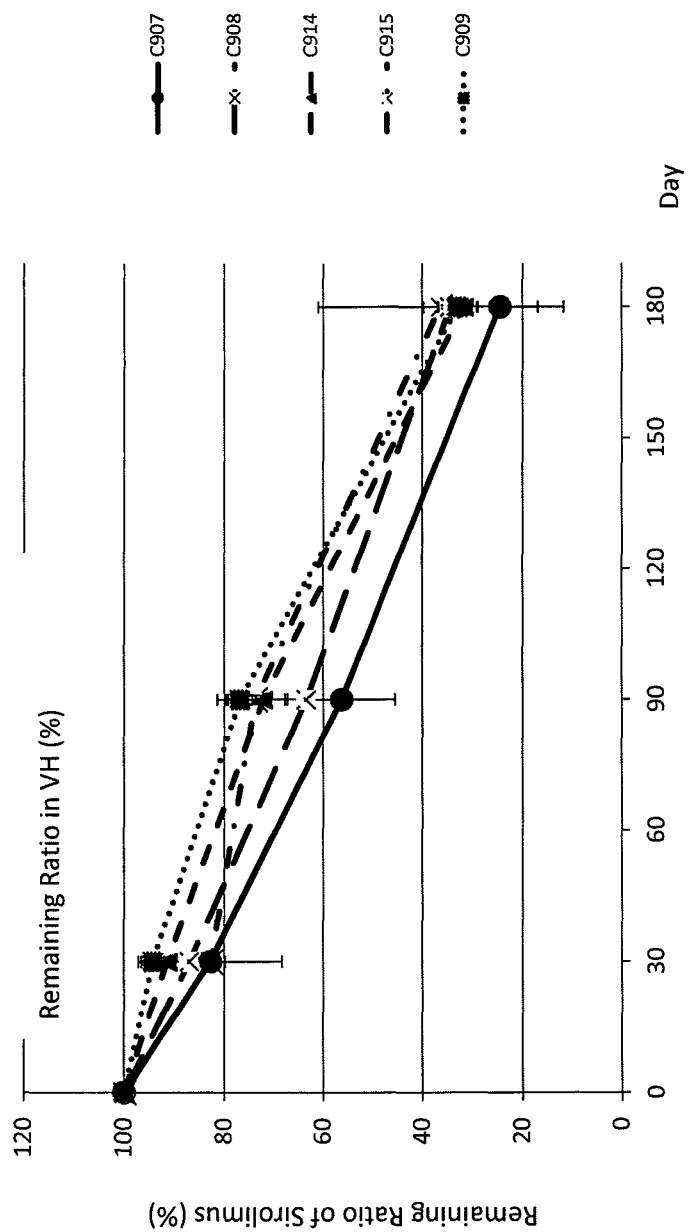

FIG. 16 shows sirolimus remaining in vitreous humor as described in more detail below in Example 11.

Figure 17:
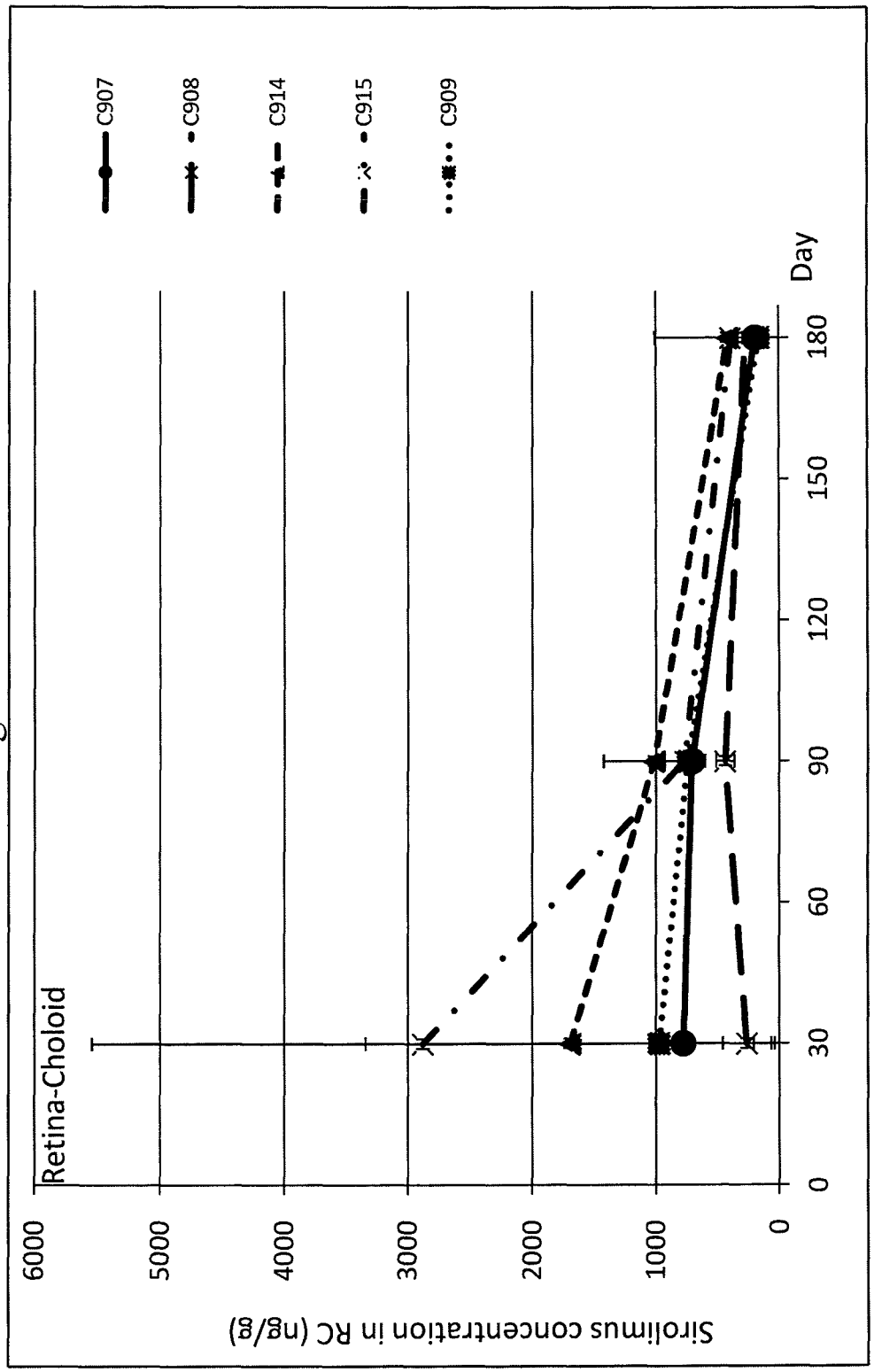

FIG. 17 shows sirolimus concentration in RC over time as described in more detail below in Example 11.

Figure 18:
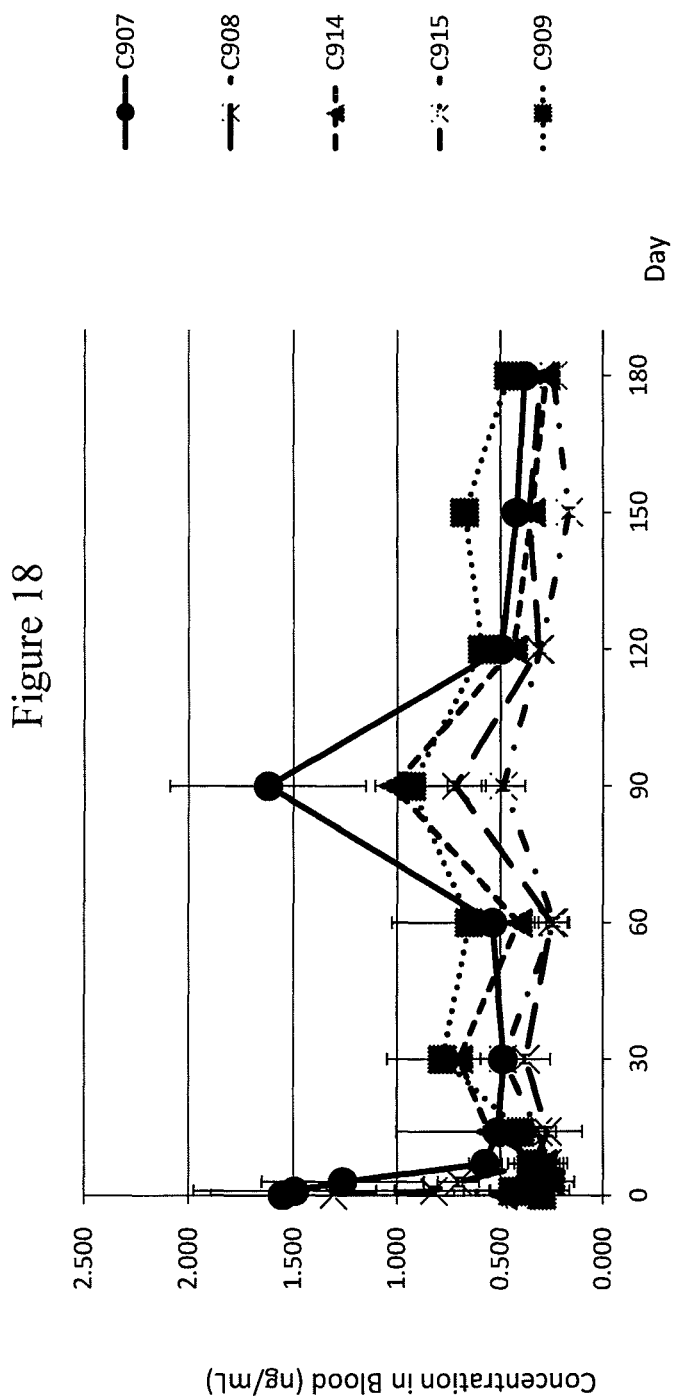

FIG. 18 shows sirolimus blood concentration after placement of intra vitreal depots as described in more detail below in Example 11.

Figure 19:
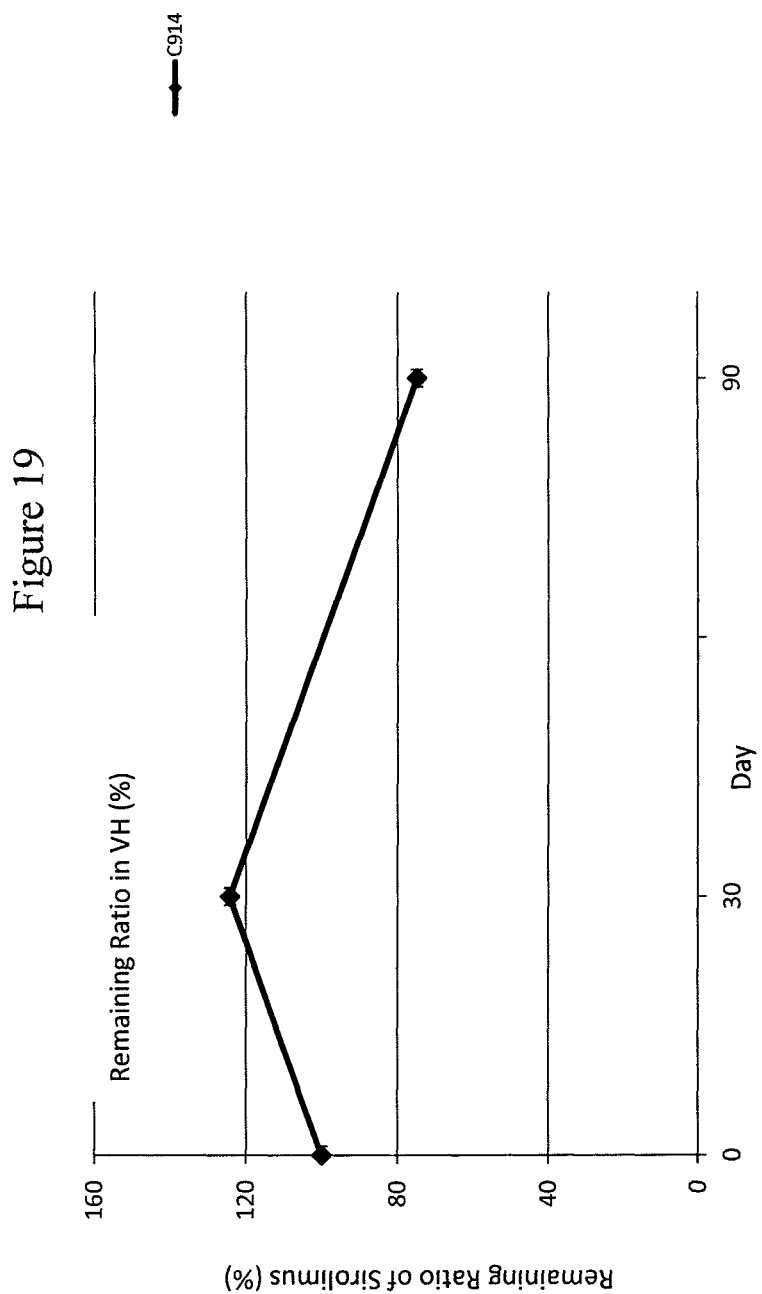

FIG. 19 shows sirolimus remaining in vitreous humor as described in more detail below in Example 12.

Figure 20:
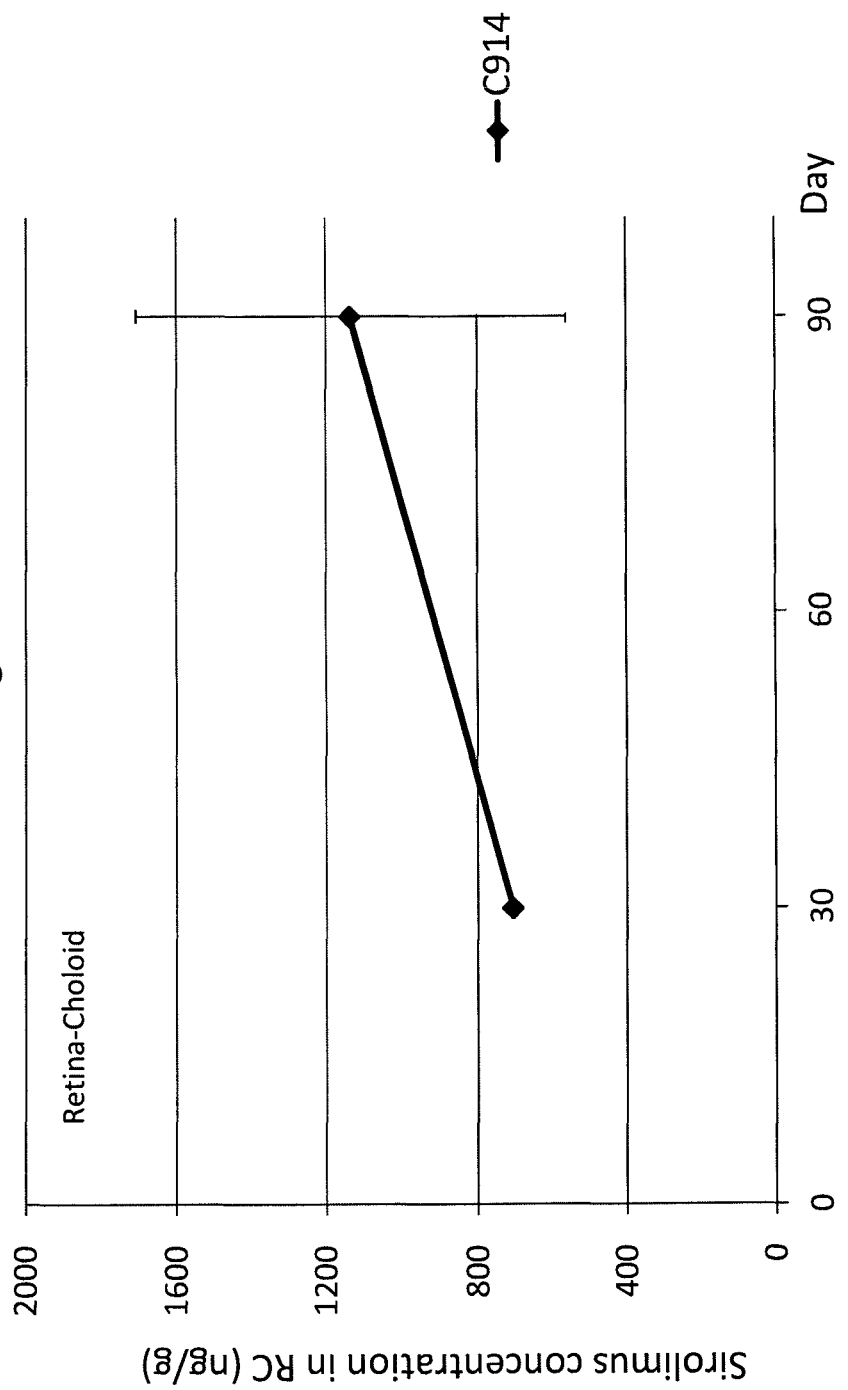

FIG. 20 shows sirolimus concentration in RC over time as described in more detail below in Example 12.

Figure 21:
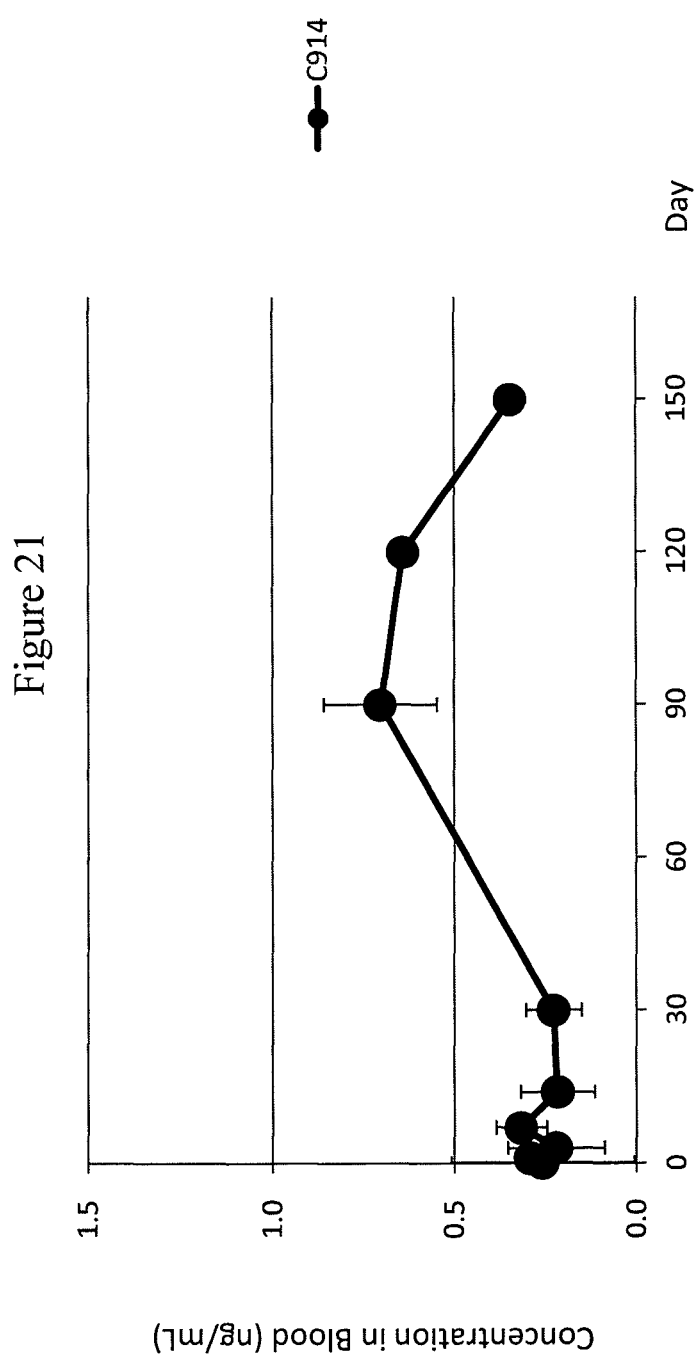

FIG. 21 shows sirolimus blood concentration after placement of intra vitreal depots as described in more detail below in Example 12.

Figure 22:
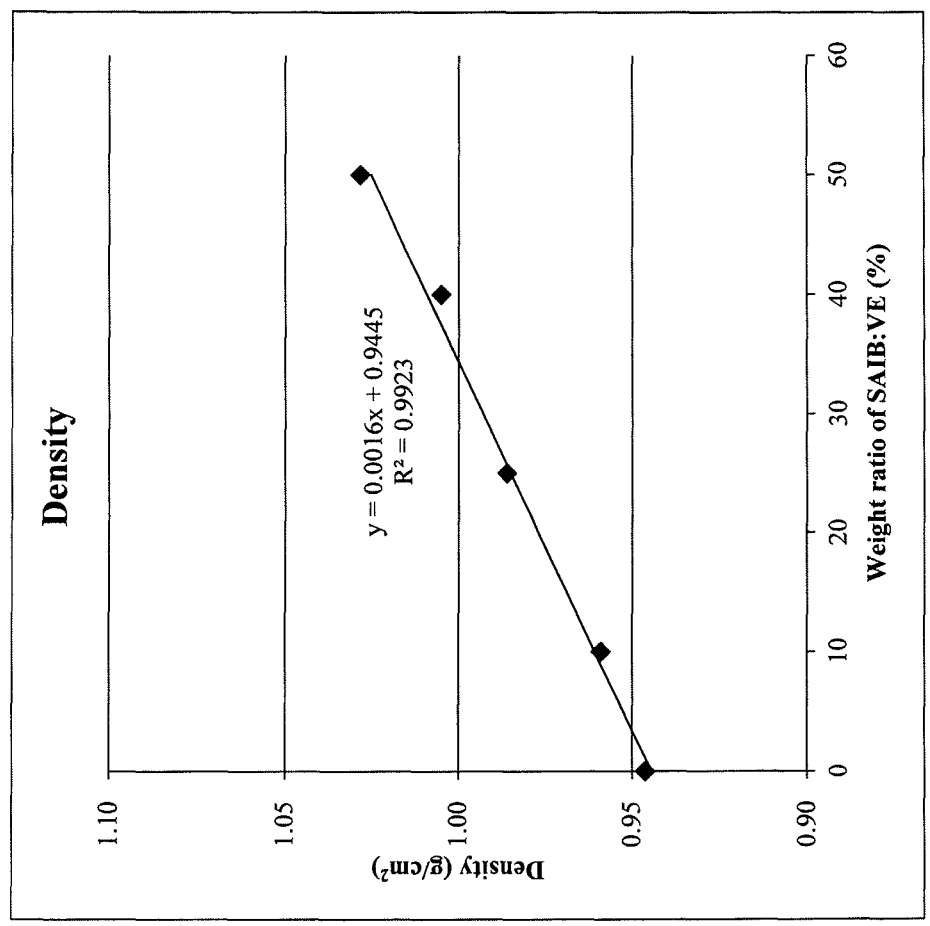

FIG. 22 plots the density at 25° C. of mixtures consisting of SAIB and vitamin E, as a function of the weight ratio of SAIB:VE.

Figure 23:
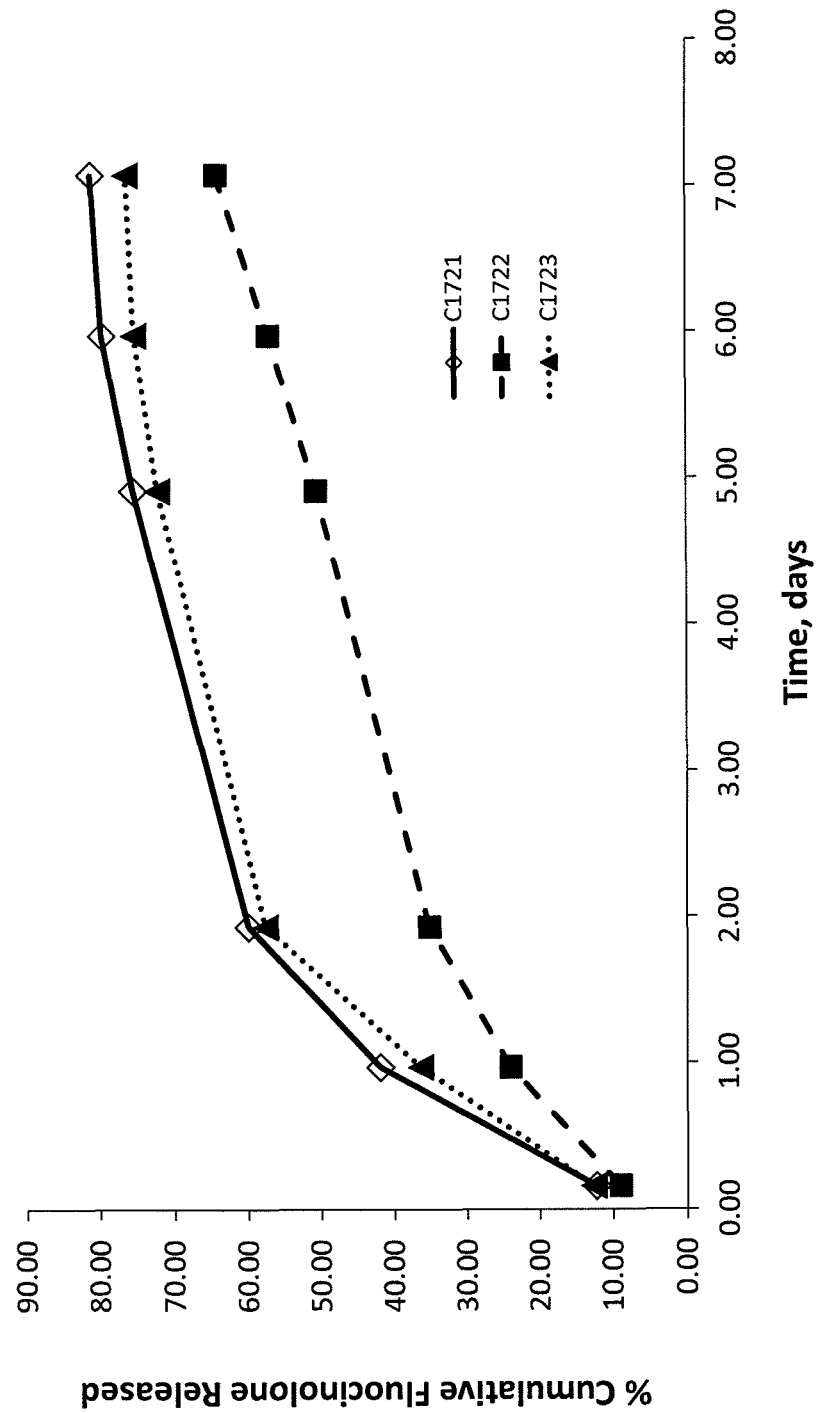

FIG. 23 shows the release profiles of inventive compositions comprising fluocinolone as active pharmaceutical ingredient.

Figure 24:
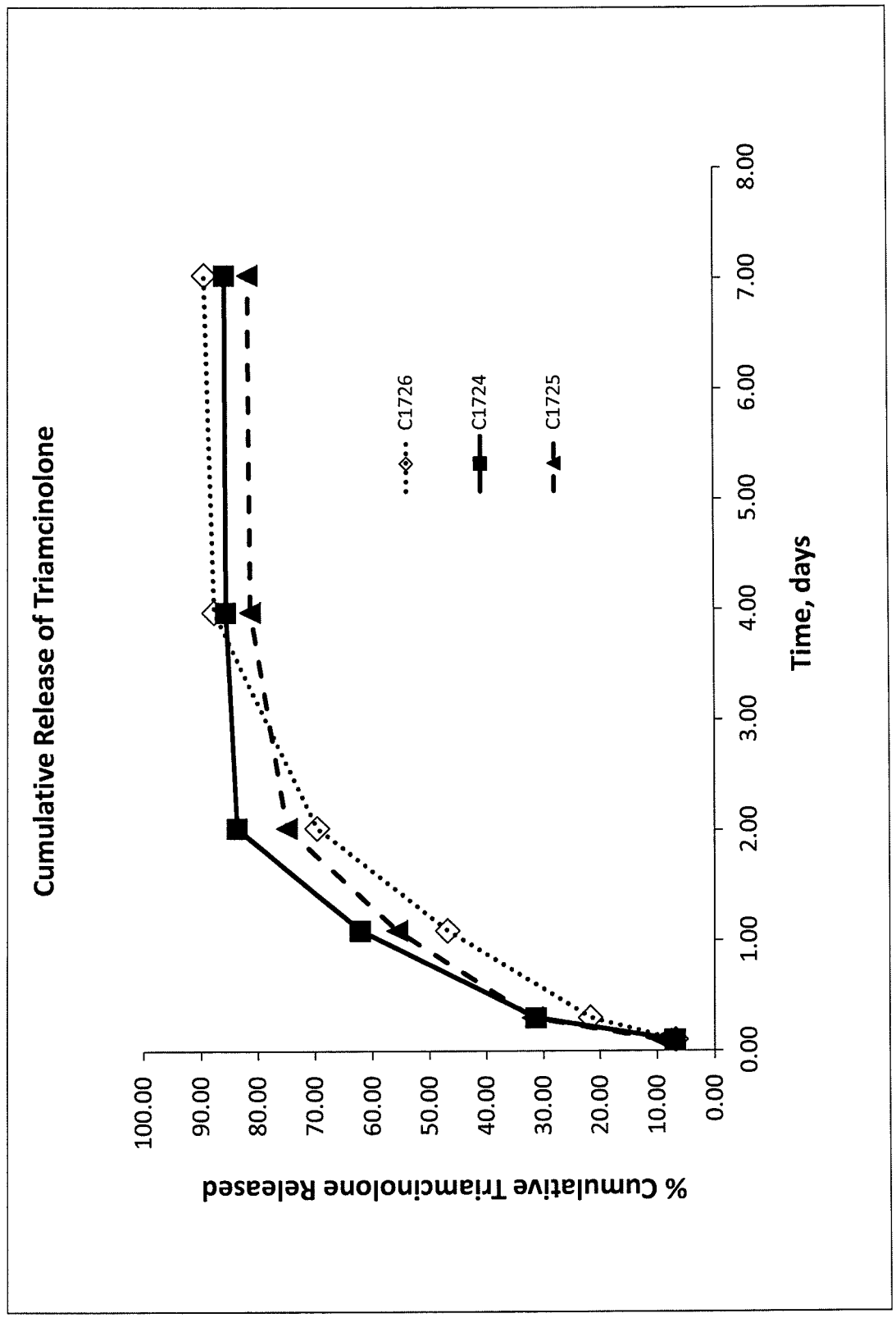

FIG. 24 shows the release profiles of inventive compositions comprising triamcinolone as active pharmaceutical ingredient.

Figure 25:
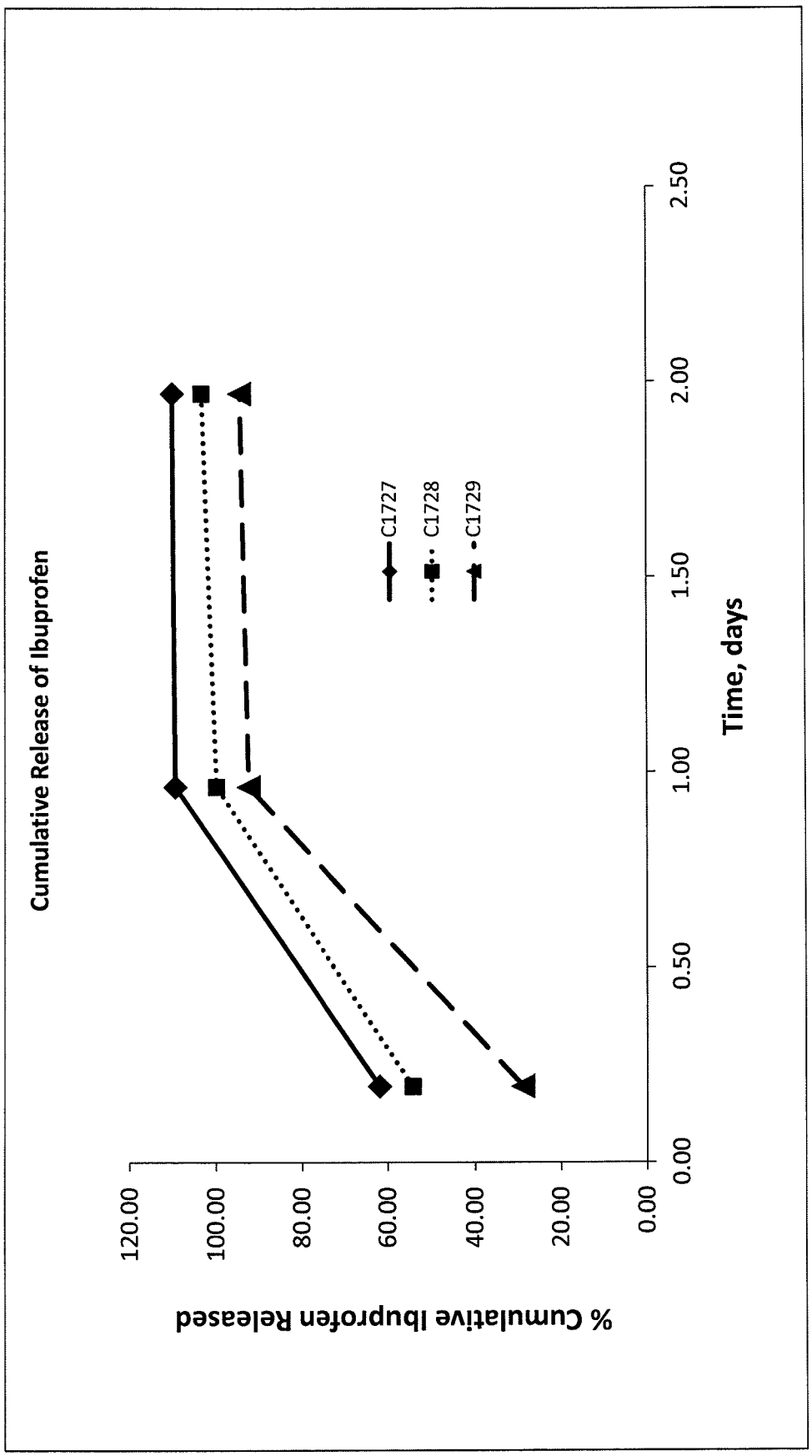

FIG. 25 shows the release profiles of inventive compositions comprising ibuprofen as active pharmaceutical ingredient.

DETAILED DESCRIPTION

Quantities may be described herein as a set of upper preferred values and a set of lower preferred values. Preferred ranges include any ranges formed from an upper preferred value and a lower preferred value, as well as two lower preferred values and two upper preferred values. The Examples also disclose quantities (e.g., weight percents, ratios, etc.). Preferred ranges also include ranges formed from two values disclosed in examples, and ranges formed from one value disclosed in an example, and another value disclosed in either a set of upper or lower values. All such ranges are expressly disclosed herein.

Formulations according to the present disclosure generally comprise an active pharmaceutical ingredient (API) in a carrier composition. In some cases, the carrier composition comprises one or more of a high viscosity liquid carrier material (HVLCM), a hydrophobic solvent, a hydrophilic solvent, and an antioxidant. In some cases, the carrier composition comprises one or more of a high viscosity liquid carrier material (HVLCM), a hydrophobic solvent, a hydrophilic solvent, a polymer, an antioxidant, and other excipients.

Any biologically active substance (BAS) or active pharmaceutical ingredient (API) or active compound suitable for a depot formulation may be used in compositions of the present disclosure. Furthermore, as used herein, descriptions regarding administration, dosages, weight percent, and similar aspects of the present disclosure set forth herein with regard to any one of BAS, API, or active compound are intended to also apply to the other substances, ingredients, or compounds, unless otherwise noted. Some exemplary classes of API include immunosuppressants, anti-inflammatories, and antibiotics. Biologically active substances, API's, and active compounds described herein also include pharmaceutically acceptable prodrugs, derivatives, analogs, salts, derivatives, and esters thereof.

The term "biologically active substance" as used herein refers to an inorganic or organic molecule including a drug, peptide, protein, carbohydrate (including monosaccharides, oligosaccharides, and polysaccharides), nucleoprotein, mucoprotein, lipoprotein, synthetic polypeptide or protein, or a small molecule linked to a protein, glycoprotein, steroid, nucleic acid (any form of DNA, including cDNA, or RNA, or a fragment thereof), nucleotide, nucleoside, oligonucleotides (including antisense oligonucleotides), gene, lipid, hormone, or combination thereof, that causes a biological effect when administered in vivo to an animal, including but not limited to birds and mammals, including humans.

Suitable proteins include, but are not limited to, human growth hormone, fibroblast growth factor (FGF), erythropoietin (EPO), platelet derived growth factor (PDGF), granulocyte colony stimulating factor (g-CSF), bovine somatotropin (BST), tumor necrosis factor (TNF), transforming growth factor-beta (TGF-Beta), interleukins, insulin, and interferons, such as α-interferon, β-interferon, and the like.

The term drug (or active pharmaceutical ingredient, API), as used herein, refers to any substance used internally or externally as a medicine for the treatment, cure, or prevention of a disease or disorder, and includes but is not limited to immunosuppressants, anesthetics, analgesics, chemotherapeutic agents, steroids (including retinoids), hormones, antibiotics, antivirals, antifungals, antiproliferatives, antihistamines, anticoagulants, antiphoto-aging agents, melanotropic peptides, nonsteroidal and steroidal anti-inflammatory compounds, antipsychotics, and radiation absorbers, including UV-absorbers.

The term biologically active substance also includes agents such as insecticides, pesticides, fungicides, rodenticides, and plant nutrients and growth promoters.

The term pharmaceutically acceptable means safe and effective for pharmaceutical use, which can include human or veterinary use, preferably human use. A composition that is pharmaceutically acceptable is preferably suitable for use to treat a medical condition in an animal or human. A pharmaceutically acceptable composition preferably comprises, consists essentially of, or consists of, a combination of one or more active pharmaceutical ingredients, and one or more pharmaceutically acceptable excipients.

Immunosuppressants include any immunosuppressant useful in depot formulations, including macrolide lactones, cyclosporines, and others. Immunosuppressants include APIs having immunosuppressant activity, even if the API is not primarily used as an immunosuppressant in any particular formulation or use thereof.

Therapeutic agents that may be used include but are not limited to compounds that act by binding members of the immunophilin family of cellular proteins. Such compounds are known as "immunophilin binding compounds." Immunophilin binding compounds include but are not limited to the "limus" family of macrolide lactone compounds. Examples of limus compounds that may be used include but are not limited to sirolimus (rapamycin) and its water soluble analog SDZ-RAD (Novartis), TAFA-93 (Isotechnika), tacrolimus, everolimus, RAD-001 (Novartis), pimecrolimus, temsirolimus, CCI-779 (Wyeth), AP23841 (Ariad), AP23573 (Ariad), and ABT-578 (Abbott Laboratories). Limus compound analogs and derivatives that may be used include but are not limited to the compounds described in U.S. Pat. Nos. 5,527,907; 6,376,517; 6,329,386; and 6,890,546; each of which is incorporated herein by reference in their entirety. Therapeutic agents also include analogs, prodrugs, salts, derivatives and esters of limus compounds.

In some compositions of the present disclosure the therapeutic agent comprises, consists essentially of, or consists of, a limus compound. In some compositions of the present disclosure the therapeutic agent comprises, consists essentially of, or consists of, an immunophilin binding compound. In some compositions of the present disclosure the therapeutic agent comprises, consists essentially of, or consists of, an mTOR inhibitor or an analog, derivative, salt, ester or prodrug thereof (e.g., TAFA93). In some compositions of the present disclosure the therapeutic agent comprises, consists essentially of, or consists of, a cyclophilin or an FK-506 binding protein (FKBP).

Other sirolimus derivatives that may be used include, without limitation, 7-epi-rapamycin, 7-thiomethyl-rapamycin, 7-epi-trimethoxyphenyl-rapamycin, 7-epi-thiomethyl-rapamycin, 7-demethoxy-rapamycin, 32-demethoxy-rapamycin, 2-desmethyl-rapamycin, mono- and di-ester derivatives of rapamycin, 27-oximes of rapamycin; 42-oxo analog of rapamycin; bicyclic rapamycins; rapamycin dimers; silyl ethers of rapamycin; rapamycin arylsulfonates and sulfamates, mono-esters and di-esters at positions 31 and 42, 30-demethoxy rapamycin, and other derivatives described in Vezina et al., "Rapamycin (AY-22,989), A New Antifungal Antibiotic. I. Taxonomy Of The Producing Streptomycete And Isolation Of The Active Principle" J. Antibiot. (Tokyo) 28:721-726 (1975); Sehgal et al., "Rapamycin (AY-22,989), A New Antifungal Antibiotic. II. Fermentation, Isolation And Characterization" J. Antibiot. (Tokyo) 28:727-732 (1975); Sehgal et al., "Demethoxyrapamycin (AY-24, 668), A New Antifungal Antibiotic" J. Antibiot. (Tokyo) 36:351-354 (1983); and Paiva et al., "Incorporation Of Acetate, Propionate, And Methionine Into Rapamycin By Streptomycetes hygroscopicus" J Nat Prod 54:167-177 (1991), WO 92/05179, EP 467606, Caufield et al., "Hydrogenated Rapamycin Derivatives" U.S. Pat. No. 5,023,262; Kao et al., "Bicyclic Rapamycins" U.S. Pat. No. 5,120,725; Kao et al., "Rapamycin Dimers" U.S. Pat. No. 5,120,727; Failli et al., "Silyl Ethers Of Rapamycin" U.S. Pat. No. 5,120,842; Failli et al., "Rapamycin 42-Sulfonates And 42-(N-carboalkoxy) Sulfamates Useful As Immunosuppressive Agents" U.S. Pat. No. 5,177,203; Nicolaou et al., "Total Synthesis Of Rapamycin" J. Am. Chem. Soc. 115: 4419-4420 (1993); Romo et al, "Total Synthesis Of (–) Rapamycin Using An Evans-Tishchenko Fragment Coupling" J. Am. Chem. Soc. 115:7906-7907 (1993); and Hayward et al, "Total Synthesis Of Rapamycin Via A Novel Titanium-Mediated Aldol Macrocyclization Reaction" J. Am. Chem. Soc., 115:9345-9346 (1993), each of which is incorporated herein by reference in its entirety.

The limus family of compounds may be used in the formulations and methods for the treatment, prevention, inhibition, delaying the onset of, or causing the regression of the diseases and conditions described herein.

Additional non-limiting examples of pharmacological materials include anti-infectives such as nitrofurazone, sodium propionate, antibiotics (including penicillin, tetracycline, oxytetracycline, chlorotetracycline, bacitracin, nystatin, streptomycin, neomycin, polymyxin, gramicidin, chloramphenicol, erythromycin, and azithromycin), sulfonamides, including sulfacetamide, sulfamethizole, sulfamethazine, sulfadiazine, sulfamerazine, and sulfisoxazole, and anti-virals including idoxuridine, ganciclovir, trifluridine, and vidarabine; anti-inflammatories such as NSAIDS (including acetyl salicylic acid, ibuprofen, ketoprofen, naproxen, celecoxib, diclofenac, diflunisal, etodolac, indomethacin, ketorolac, nabumetone, oxiprozin, piroxicam, salsalate, and tolmetin), steroids or glucocorticosteroids (including prednisolone, prednisone, medrol, beclomethsone, budesonide, flunisolide, fluticasone and triamcinolone); analgesics such as NSAIDS, opioids (including morphine, fentanyl, tramadol, oxycodone, methadone, hydrocodone, hydromorphone, loperamide, meperidine, tapentadol, oxymorphone, propoxyphene, remifentanil, sufentanil, alfentanil, levorphanol, codeine, and dihydrocodeine), and paracetamol (acetaminophen); antiallergenics such as antazoline, methapyritene, chlorpheniramine, pyrilamine prophenpyridamine, hydrocortisone, cortisone, hydrocortisone acetate, dexamethasone, dexamethasone 21-phosphate, fluocinolone, triamcinolone, medrysone, prednisolone, prednisolone 21-sodium succinate, and prednisolone acetate; desensitizing agents such as ragweed pollen antigens, hay fever pollen antigens, dust antigen and milk antigen; vaccines such as smallpox, yellow fever, distemper, hog cholera, chicken pox, antivenom, scarlet fever, diphtheria toxoid, tetanus toxoid, pigeon pox, whooping cough, influenza, rabies, mumps, measles, poliomyelitic, and Newcastle disease; decongestants such as phenylephrine, naphazoline, and tetrahydrazoline; miotics and anticholinesterases such as pilocarpine, esperine salicylate, carbachol, diisopropyl fluorophosphate, phospholine iodide, and demecarium bromide; parasympatholytics such as atropine sulfate, cyclopentolate, homatropine, scopolamine, tropicamide, eucatropine, and hydroxyamphetamine; sympathomimetics such as epinephrine; antipsychotics, such as olanzapine, risperidone; narcotic antagonists, such as naltrexone, naloxone, nalnothene; sedatives and hypnotics such as pentobarbital sodium, phenobarbital, secobarbital sodium, codeine, (a-bromoisovaleryl) urea, carbromal; psychic energizers such as 3-(2-aminopropyl) indole acetate and 3-(2-aminobutyl) indole acetate; tranquilizers such as reserpine, chlorpromayline, and thiopropazate; anesthetics, such as benzocaine, bupivacaine, etidocaine, lidocaine, mepivacaine, pramoxine, prilocaine, procaine, proparacaine, ropivacaine, tetracaine, levobupivacaine, chloroprocaine, butacaine, propoxycaine, phenacaine, hexylcaine, isobucaine, cyclomethycaine, benoxinate, diperodon, dibucaine, meprylcaine, dimethisoquin, pramoxine, butamben, dyclonine (with and without augmenting agents such as dexamethasone or epinephrine); tricyclic antidepressants such as amitriptyline or nortryptyline; androgenic steroids such as methyl-testosterone and fluorymesterone; estrogens such as estrone, 17-fl-estradiol, ethinyl estradiol, and diethyl stilbestrol; progestational agents such as progesterone, megestrol, melengestrol, chlormadinone, ethisterone, norethynodrel, 19-norprogesterone, norethindrone, medroxyprogesterone and 17-0-hydroxyprogesterone; humoral agents such as the Prostaglandins, for example PGEI, PGE2 and PGF2; antipyretics such as aspirin, sodium salicylate, and salicylamide; antispasmodics such as atropine, methantheline, papaverine, and methscopolamine bromide; antimalarials such as the 4-aminoquinolines, 8-aminoquinolines, chloroquine, and pyrimethamine; antihistamines such as diphenhydramine, dimenhydrinate, tripelennamine, perphenazine, and chlorphenazine; cardioactive agents such as dibenzhydroflume thiazide, flumethiazide, chlorothiazide, and aminotrate; statins, such as atorvastatin, cerivastatin, fluvastatin, lovastatin, pravastatin, simvastatin, and related compounds; antiasthmatics, such as cromolyn; bone resorption prevention agents, such as bisphosphonates, including as nonlimiting examples alendronate, risendronate, zolendronate, pamidronate, and ibandronate; calcium regulating hormones, such as calcitonin; nutritional agents such as natural and synthetic bioactive peptides; and proteins, including growth factors, cell adhesion factors, cytokines, and biological response modifiers.

In some compositions of the present disclosure, the active pharmaceutical ingredient is capable of treating an eye condition, e.g. it comprises a substance that is capable of treating an eye condition. Such a substance is also known as an ophthalmic drug. In some compositions of the present disclosure, the active pharmaceutical ingredient does not comprise an ophthalmic drug other than sirolimus, and in some aspects the active pharmaceutical ingredient does not comprise an ophthalmic drug.

The active compound is included in the composition in an amount sufficient to deliver to the host human or animal an effective amount to achieve a desired effect. The amount of drug or biologically active agent incorporated into the composition depends upon the desired release profile, the concentration of drug required for a biological effect, and the desired period of release of the drug.

The concentration of active compound in the composition will also depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The composition may be administered in one dosage, or may be divided into a number of smaller doses to be administered at varying intervals of time.

The biologically active substance is typically present in amounts and/or concentrations capable of administering effective amounts to a patient in need of the biologically active substance. The amount and/or concentration depends on the biologically active substance used, and can also depend on the situs of administration. The amount and/or concentration of biologically active substance can be determined by a person of ordinary skill using the present specification for guidance. As a general matter, higher concentrations are preferred since this may permit administrations of depots having smaller volumes. Concentrations generally should not be so high that the BAS or other components have a high probability of precipitating since this could affect performance (e.g., bioavailability) and/or have other adverse effects. In the case of some ophthalmic depots, high concentration/low volume is preferred, but precipitation should be avoided since this can affect vision and/or impact bioavailability of the BAS (e.g., sirolimus). Without limiting the disclosure, the biologically active substance is typically present in the present composition in amounts of at least 0.05 wt %, 0.1 wt %, 0.5 wt %, 1 wt %, or 2 wt %, based on weight of the composition. The biologically active substance is typically present in the composition in amounts up to 20 wt %, 10 wt %, 7 wt %, 5 wt %, 4 wt %, or 3 wt %, based on weight of the composition. In some cases, the biologically active substance comprises sirolimus present in an amount ranging from 1 wt % to 10 wt %, based on weight of the composition.

Compositions of the present disclosure can include one or more biologically active substance (BAS), API, or active compound. When two or more BASs are used, they can be from the same therapeutic class, or from different therapeutic classes. For example, the active pharmaceutical ingredient may comprise sirolimus and at least one further therapeutic agent, e.g., at least one further ophthalmic drug. Some possible combinations of BASs include sirolimus and tacrolimus; sirolimus and cyclosporine; and sirolimus and prednisolone.

Compositions of the present disclosure preferably comprise a pharmaceutically acceptable high viscosity liquid carrier material (HVLCM), preferably pharmaceutically acceptable for ophthalmic depots. The HVLCM is non-polymeric, non-water soluble, and has a viscosity of at least 5,000 cP, (and optionally at least 10,000; 15,000; 20,000; 25,000; or even 50,000 cP) at 37° C. The HVLCM preferably does not crystallize neat under ambient or physiological conditions of a subject. The term non-water soluble refers to a material that is soluble in water to a degree of less than 1 wt % under ambient conditions, e.g., room temperature or 23° C. The term "non-polymeric" in this context refers to esters or mixed esters having essentially no repeating units in the acid moiety of the ester, as well as esters or mixed esters having acid moieties wherein functional units in the acid moiety are repeated a small number of times (i.e., oligomers). Generally, materials having more than five identical and adjacent repeating units or -mers in the acid moiety of the ester are excluded by the term "nonpolymeric" as used herein, but materials containing dimers, trimers, tetramers, or pentamers are included within the scope of this term.

The HVLCM may comprise, consist essentially of, or consist of, sucrose acetate isobutyrate ("SAIB"). SAIB is an exemplary HVLCM.

The term "SAIB" refers to molecules of sucrose whose eight native hydroxyl groups are each esterified with a —COCH$_3$ (acetyl) or —COCH(CH$_3$)$_2$ (isobutyryl) moiety. SAIB is a commercially available product, sold for example in the form of a mixture of compounds having different patterns of acetyl and isobutyryl substitutions of the native sucrose hydroxyl groups (e.g. differing ratios of acetyl to isobutyryl moieties and/or different ring positions of the acetyl and isobutyryl moieties). A skilled artisan would understand that SAIB typically comprises a mixture of differently-substituted "isoforms," which includes a sucrose molecule nominally esterified preferably with two acetic acid and six isobutyric acid moieties. Thus, the HVLCM may comprise, consist essentially of, or consist of SAIB in which the native sucrose molecule is esterified with two acetic acid and six isobutyric acid moieties—the structure of which is set forth in U.S. Pat. No. 5,747,058, which is incorporated herein by reference in its entirety.

SAIB is orally non-toxic and is used as to stabilize emulsions in the food industry. It is a very viscous liquid and has an unusual property that there is a dramatic change in viscosity with small additions of heat or with the addition of solvents. It is soluble in a large number of biocompatible solvents. When in solution or in an emulsion, SAIB can be applied via injection or an aerosol spray. SAIB is compatible with cellulose esters and other polymers that can affect the rate of delivery of the substance.

The HVLCM may comprise, consist essentially of, or consist of, nonpolymeric polyalkylene polyol. Non-polymeric polyethylene glycol (PEG) is a preferred polyalkylene polyol. When the HVLCM comprises PEG, the PEG preferably has a molecular weight less than about 220 or 200 daltons. That is, preferably n≤5, where n is the average number of ethylene glycol units in the PEG. Preferred values of n for an HVLCM comprising PEG include n=5, 4, 3, or 2.

In other embodiments, the HVLCM can be stearate esters such as those of propylene glycol, glyceryl, diethylaminoethyl, and glycol, stearate amides and other long-chain fatty acid amides, such as N,N'-ethylene distearamide, stearamide MEA and DEA, ethylene bistearamide, cocoamine oxide, long-chain fatty alcohols, such as cetyl alcohol and stearyl alcohol, long-chain esters such as myristyl myristate, behenyl erucate, and glyceryl phosphates. The HVLCM may comprise acetylated sucrose distearate (Crodesta A-10).

The HVLCM is present in the composition in any amount that achieves the desired properties, e.g., viscosity and/or cohesiveness. The HVLCM is preferably present in amounts equal to or less than 99.5 wt %, 95 wt %, 85 wt %, 60 wt %, or 50 wt %, based on weight of the pharmaceutical composition. The HVLCM is preferably present in the inventive pharmaceutical compositions in amounts equal to or greater than 0.1 wt %, 0.5 wt %, 1 wt %, 10 wt %, 25 wt %, or 40 wt %, based on weight of the pharmaceutical composition. All ranges formed from combinations of these amounts or amounts disclosed in the Examples, e.g., 0.5 wt % to 50 wt %, 25 wt %-85 wt %, and 10 wt %-40 wt %, are also preferred. In some cases, the HVLCM comprises SAIB present in an amount ranging from about 0.1 wt % to 60 wt %, such as about 0.5 wt % to about 50 wt %, about 30 wt % to about 60 wt %, and about 0.1 wt % to about 10 wt % (e.g. about 0.5 wt % to about 5 wt %), based on weight of the composition.

Compositions of the present disclosure preferably comprise a pharmaceutically acceptable hydrophobic solvent, including those pharmaceutically acceptable for ophthalmic depots. Useful hydrophobic solvents exhibit a solubility in water less than 1 wt %, preferably less than 0.5 wt %, more preferably less than 0.1 wt %. Especially preferred are hydrophobic solvents having a solubility in water less than 0.05 wt %. The solubility is measured at 25° C. Some examples of hydrophobic solvents include benzyl benzoate (BB), isopropyl myristate (IPM), isopropyl palmitate, acetyl trialkyl citrate (e.g., acetyl tributyl citrate (ATBC)), and trialkyl citrate (e.g., tributyl citrate (TBC)).

BB and IPM are commercially available products.

Other suitable hydrophobic solvents include triglycerides (e.g., caprylic/capric triglyceride (Miglyol 810)), and dimethyl phthalate, as well as fatty esters and ethers such as ethyl oleate and ethyl caprate.

When used, trialkyl citrate (TAC) may comprise or consist essentially of a compound represented by formula (A) below. In formula (A), $R^a$, $R^b$ and $R^c$ denote the same or different alkyl groups, each having 3 to 5 carbon atoms. The alkyl group is preferably a linear or branched alkyl group, and is more preferably a linear or branched alkyl group having a carbon number of 4. Some preferred trialkyl citrates include those with an n-propyl group, n-butyl group, n-pentyl group, isopropyl group, isobutyl group, sec-butyl group, tert-butyl group, isopentyl group, etc. Trialkyl citrate with three n-butyl groups (referred to herein as tributyl citrate, or TBC) is more preferred.

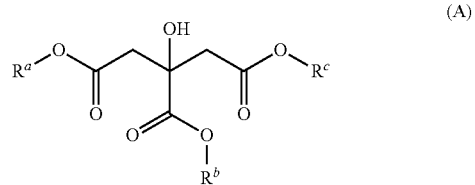

(A)

In Formula (A), $R^a$, $R^b$ and $R^c$ may each be the same, or may be different. Preferably, $R^a$, $R^b$ and $R^c$ are the same.

When used, acetyl trialkyl citrate (ATAC) may comprise or consist essentially of a compound represented by formula (B) below, which is also referred to as trialkyl acetyl citrate and 2-acetoxypropane-1,2,3-trialkyl tricarboxylic acid. In formula (B), $R^a$, $R^b$ and $R^c$ each denote alkyl groups having a carbon number of 3 to 5. The alkyl group is preferably a linear or branched alkyl group, preferably having a carbon number of 4. Some preferred acetyl trialkyl citrates include those with an n-propyl group, n-butyl group, n-pentyl group, isopropyl group, isobutyl group, sec-butyl group, tert-butyl group, isopentyl group, etc. Acetyl trialkyl citrate with three n-butyl groups (referred to herein as acetyl tributyl citrate, or ATBC) is more preferred.

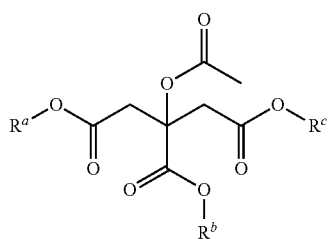

(B)

In Formula (B), $R^a$, $R^b$ and $R^c$ may each be the same, or may be different. Preferably, $R^a$, $R^b$ and $R^c$ are the same.

As hydrophobic solvent, TAC or ATAC may be used individually, or in combination with each other. TAC and/or ATAC may also be used in combination with one or more other hydrophobic solvents. When used in combination, any ratio of TAC:ATAC may be used. Some ratios of TAC:ATAC (volume:volume) include 0:100, 0.1:99.9, 5:95, 10:90, 15:85, 30:70, 50:50, 70:30, 85:15, 90:10, 95:5, 99.9:0.1, and 100:0. Ranges formed from any two of these ratios are also preferred.

The compositions of the present disclosure can comprise any amount of hydrophobic solvent to confer suitable properties to the composition. Compositions of the present disclosure, when they comprise hydrophobic solvent, preferably comprise at least 0.1 wt %, 1 wt %, 2 wt %, 10 wt %, 20 wt %, 30 wt %, and 40 wt %. Compositions of the present disclosure, when they comprise hydrophobic solvent, preferably comprise up to 99 wt %, 95 wt %, 90 wt %, 80 wt %, 70 wt %, 60 wt %, and 50 wt %. In some cases, the hydrophobic solvent comprises benzyl benzoate in an amount ranging from about 30 wt % to about 60 wt %, or about 35 wt % to about 45 wt %, based on weight of the composition. In other cases, the hydrophobic solvent comprises ATBC in an amount ranging from about 30 wt % to about 60 wt %, or about 35 wt % to about 50 wt %, based on weight of the composition.

Compositions of the present disclosure preferably comprise a pharmaceutically acceptable hydrophilic solvent, including those pharmaceutically acceptable for ophthalmic depots. The hydrophilic solvent, when used, is preferably non-polymeric, e.g., other than polyalkylene glycol or polyethylene glycol. A hydrophilic solvent preferably has a solubility in water at least 1 wt %, 2 wt %, 10 wt %, 25 wt %, 50 wt %, up to and including miscibility with water, when measured at 25° C. When a hydrophobic solvent is used, the hydrophilic solvent exhibits a solubility in water greater than the hydrophobic solvent. Some preferred hydrophilic solvents include ethanol, ethyl lactate (EL), dimethyl sulfoxide (DMSO), N-methyl-2-pyrrolidone (NMP), polyalkylene polyol, ethyl acetate, propylene glycol, propylene carbonate, glycerin, and triacetin (TA).

Commercially available hydrophilic solvents may include minor amounts of water. When it is desired to reduce or eliminate water in the inventive pharmaceutical compositions, it may be advantageous to use anhydrous (or dry) hydrophilic solvent. Hydrophilic solvent can be commercially obtained in anhydrous (or low-hydrous) form, and/or hydrophilic solvent containing water can be dried. These same considerations apply to other components of inventive compositions, as well as to pharmaceutical compositions of the present disclosure. Components that form an azeotrope with water (e.g., ethanol) are preferably used in anhydrous form. Anhydrous ethanol includes, for example, products indicated as 99.5% EtOH, 200 proof, and/or comprising less than 0.005% water.

Ethanol, ethyl lactate, dimethyl sulfoxide, N-methyl-2-pyrrolidone, polyalkylene polyols, and triacetin are all widely commercially available products of commerce. When used, ethanol is preferably not denatured. In some cases, ethanol is present in an amount ranging from about 1 wt % to about 10 wt %, based on weight of the composition (e.g. from about 1 wt % to about 7 wt %, such as about 1 wt % to about 5 wt %).

When a hydrophilic solvent includes polyalkylene polyol, any molecular weight (or degree of polymerization) may be used, with the caveat that in order to act as a hydrophilic solvent, the polyalkylene polyol should be a liquid at ambient temperature, e.g., 23° C. A preferred polyalkylene polyol is polyethylene glycol (PEG). PEG 300 (n about 7), PEG 400 (n about 9), and PEG 600 (n about 13) are liquids at 23° C., while PEG 800 (n about 18) is a paste at 23° C. Preferred PEGs as hydrophilic solvent include PEG 600, PEG 400, and PEG 300.

When used, hydrophilic solvent is generally present in amounts up to 70 wt %, up to 60 wt %, up to 50 wt %, up to 40 wt %, up to 30 wt %, up to 20 wt %, up to 15 wt %, or up to 10 wt % of the composition. Though there is generally no lower limit, when hydrophilic solvent is used, it is generally present in amounts of at least 0.1 wt %, at least 1 wt %, at least 2 wt %, at least 3 wt %, at least 4 wt %, or at least 5 wt %. In some cases, the hydrophilic solvent comprises ethanol in an amount ranging from about 1 wt % to about 20 wt %, or about 2 wt % to about 10 wt %, based on weight of the composition. In some cases, the hydrophilic solvent comprises PEG in an amount ranging from about 30 wt % to about 60 wt %, or about 40 wt % to about 50 wt %, based on weight of the composition. In some cases, the compositions of the invention may contain both ethanol and PEG, for example in which the amounts of ethanol and PEG, respectively, each fall within the illustrative amounts outlined herein.

It is possible for a PEG of sufficiently low molecular weight (e.g., n≤5) to act as both HVLCM and hydrophilic solvent, in which case the total amount may be apportioned among the two components, or may be classified solely with one of the two components.

In some cases, the vehicle formulation comprises SAIB, BB, and ethanol. In some other cases, the vehicle formulation comprises SAIB, BB and ethanol and additional components to provide a formulation with a more desirable release profile. In some cases, the formulation provides reproducible release of sirolimus from a composition administered intraocularly as a single dose to a mammalian subject, e.g., a human subject (or patient)

Compositions of the present disclosure optionally include one or more polymers. Including a polymer that can confer beneficial properties to the composition. For example, use of polymer can help to slow API release, helping to give a more sustained release rate. This can help to extend the life of the depot. Reducing the rate of release can also help to control drug exposure, and/or help to control exposure to safe and effective levels, and/or eliminate or reduce overexposure.

Some preferred polymers include poloxamer, polyalkylene polyol, poly(lactic acid)(glycolic acid), poly(lactic acid) (or polylactides), polycaprolactone, polyglycolides, polycaprolactones, polyanhydrides, polyamines, polyurethanes, polyesteramides, polyorthoesters, polydioxanones, polyacetals, polyketals, polycarbonates, polyphosphoesters, polyoxyesters, polyorthocarbonates, polyphosphazenes, succinates, poly(malic acid), poly(amino acids), polyvinylpyrrolidone, polyethylene glycol, polyhydroxycellulose, chitin, chitosan, hyaluronic acid, and copolymers, terpolymers and mixtures thereof. Polymers that are liquid at room temperature, or that are soluble in the disclosed compositions at room temperature, are preferred.

Poloxamers are nonionic triblock copolymers comprising a central hydrophobic chain of polyoxypropylene (poly(propylene oxide)) with two hydrophilic chains of polyoxyethylene (poly(ethylene oxide)). Poloxamers are commercially available and sold under various trade names such as SYNPERONICS, PLURONICS, and KOLLIPHOR. Any suitable grade may be used, with poloxamer P188 being preferred.

When a polymer includes polyalkylene polyol, any molecular weight (or degree of polymerization) may be used, with the caveat that in order to act as a polymer in the present disclosure rather than the HVLCM, the polyalkylene polyol should have a degree of polymerization greater than 5 (that is, n>5). A preferred polyalkylene polyol is polyethylene glycol (PEG). PEG 300 (n about 7), PEG 400 (n about 9), and PEG 800 (n about 18) are preferred as such a polymer.

It is possible for a PEG of suitable molecular weight to act as both polymer (e.g., n>5) and hydrophilic solvent (e.g., n<18), in which case the total amount may be apportioned among the two components, or may be classified solely with one of the components.

Polylactides are lactic acid-based polymers that can be based solely on lactic acid or can be a copolymer, e.g., based on lactic acid, glycolic acid and/or caprolactone, which may include small amounts of other co-monomers that do not substantially affect the advantageous results that can be achieved in accordance with the present disclosure. As used herein, the term "lactic acid" includes the isomers L-lactic acid, D-lactic acid, DL-lactic acid and lactide, while the term "glycolic acid" includes glycolide. Most preferred are one or more of the following polymers: polylactide polymers, commonly referred to as PLA; poly(lactide-co-glycolide) copolymers, commonly referred to as PLGA; and poly(caprolactone-co-lactic acid) (PCL-co-LA). The polymer may have a monomer ratio of lactic acid/glycolic acid of from about 100:0 to about 10:90, such as 100:0 to 15:85, preferably from about 75:25 to about 30:70, more preferably from about 60:40 to about 40:60, and an especially useful copolymer has a monomer ratio of lactic acid/glycolic acid of about 50:50.

The poly(caprolactone-co-lactic acid) (PCL-co-LA) polymer preferably has a co-monomer ratio of caprolactone/lactic acid of from about 10:90 to about 90:10, from about 50:50; preferably from about 35:65 to about 65:35; and more preferably from about 25:75 to about 75:25. In certain embodiments, the lactic acid-based polymer may comprise a blend of about 0% to about 90% caprolactone, about 0% to about 100% lactic acid, and about 0% to about 60% glycolic acid.

Other suitable polymers include PEG-PLGA, poly(vinyl alcohol), and poly(ortho ester).

The polymer may have an average molecular weight of from about 1,000 to about 120,000, such as from about 5,000 to about 50,000 or about 8,000 to about 30,000, as determined by gel permeation chromatography (GPC). For instance, the lactic acid-based polymer preferably has an average molecular weight of from about 1,000 to about 120,000, preferably from about 5,000 to about 50,000, more preferably from about 8,000 to about 30,000, as determined by gel permeation chromatography (GPC). As indicated in U.S. Pat. No. 5,242,910, the polymer can be prepared in accordance with the teachings of U.S. Pat. No. 4,443,340. Alternatively, the lactic acid-based polymer can be prepared directly from lactic acid or a mixture of lactic acid and glycolic acid (with or without a further co-monomer) in accordance with the techniques set forth in U.S. Pat. No. 5,310,865. The contents of all of these patents are incorporated by reference. Suitable lactic acid-based polymers are available commercially. For instance, 50:50 lactic acid:glycolic acid copolymers having molecular weights of 8,000, 10,000, 30,000 and 100,000 are available from Boehringer Ingelheim Chemicals, Inc. (Petersburg, Va.), Medisorb Technologies International L.P. (Cincinnati, Ohio) and Lactel Absorbable Polymers (formerly Birmingham Polymers, Inc.) as described below.

Examples of suitable lactide polymers include, but are not limited to, poly (D,L-lactide) RESOMER L104, PLA-L104, poly (D,L-lactide-co-glycolide) 50:50 RESOMER RG502, poly (D,L-lactide-co-glycolide) 50:50 RESOMER RG502H, poly (D,L-lactide-co-glycolide) 50:50 RESOMER RG503, poly (D,L-lactide-co-glycolide) 50:50 RESOMER RG506, poly L-lactide MW 2,000 (RESOMER L 206, RESOMER L 207, RESOMER L 209, RESOMER L 214); poly D,L-lactide (RESOMER R 104, RESOMER R 202, RESOMER R 203, RESOMER R 206, RESOMER R 207, RESOMER R 208); poly L-lactide-co-D,L-lactide 90:10 (RESOMER LR 209); polyglycolide (RESOMER G 205); poly D,L-lactide-co-glycolide 50:50 (RESOMER RG 504H, RESOMER RG 504, RESOMER RG 505); poly D-L-lactide-co-glycolide 75:25 (RESOMER RG 752, RESOMER RG755, RESOMER RG 756); poly D,L-lactide-co-glycolide 85:15 (RESOMER RG 858); and poly L-lactide-co-trimethylene carbonate 70:30 (RESOMER LT 706) (Boehringer Ingelheim Chemicals, Inc., Petersburg, Va.).

Additional examples include, but are not limited to, DL-lactide/glycolide 100:0 (MEDISORB Polymer 100 DL High, MEDISORB Polymer 100 DL Low); DL-lactide/glycolide 85/15 (MEDISORB Polymer 8515 DL High, MEDISORB Polymer 8515 DL Low); DL-lactide/glycolide 75/25 (MEDISORB Polymer 7525 DL High, MEDISORB Polymer 7525 DL Low); DL-lactide/glycolide 65/35 (MEDISORB Polymer 6535 DL High, MEDISORB Polymer 6535 DL Low); DL-lactide/glycolide 54/46 (MEDISORB Polymer 5050 DL High, MEDISORB Polymer 5050 DL Low); and DL-lactide/glycolide 54/46 (MEDISORB Polymer 5050 DL 2A(3), MEDISORB Polymer 5050 DL 3A(3), MEDISORB Polymer 5050 DL 4A(3)) (Medisorb Technologies International L.P., Cincinnati, Ohio); and Poly D,L-lactide-co-glycolide 50:50; Poly D,L-lactide-co-glycolide 65:35; Poly D,L-lactide-co-glycolide 75:25; Poly D,L-lactide-co-glycolide 85:15; Poly DL-lactide; Poly L-lactide; Poly glycolide; Poly .epsilon.-caprolactone; Poly DL-lactide-co-caprolactone 25:75; and Poly DL-lactide-co-caprolactone 75:25 (Birmingham Polymers, Inc., Birmingham, Ala.).

Polymer may be present in amounts up to 40 wt %, 30 wt %, 20 wt % or 10 wt % of the pharmaceutical composition. When used, polymer may be present in amounts of at least 0.1 wt %, 1 wt %, 2 wt %, 3 wt %, 4 wt %, or 5 wt % of the pharmaceutical composition.

Poloxamers, such as disclosed above, have surfactant properties. Compositions of the present disclosure can optionally comprise one or more surfactant. Surfactants may be particularly useful in compositions having both hydrophilic and hydrophobic components (e.g., ethanol and either SAIB or a hydrophobic solvent). Any surfactant suitable for use in a depot formulation, e.g., an ophthalmic depot formulation, can be used. Non-ionic surfactants are preferred for ophthalmic compositions. Some suitable surfactants include, e.g., poloxamer, polyethoxylated castor oil, polyoxyethylated hydroxystearic acid, propylene glycol fatty esters, and sorbitan fatty esters. Poloxamers are preferred. In some cases, poloxamer is present in an amount ranging from 0.1 wt % to about 5 wt %, based on weight of the composition.

Some polyethoxylated castor oils include polyoxyl 5 castor oil, polyoxyl 9 castor oil, polyoxyl 15 castor oil, polyoxyl 35 castor oil, polyoxyl 40 castor oil, polyoxyl 40 hydrogenated castor oil, and polyoxyl 60 hydrogenated castor oil. Some preferred polyethoxylated castor oils include polyoxyl 35 castor oil (e.g., KOLLIPHOR EL), polyoxyl 40 hydrogenated castor oil (e.g., CREMOPHOR RH40), and polyoxyl 60 hydrogenated castor oil (e.g., CREMOPHOR RH60) available from BASF Corporation of Midland, Mich.

Polyoxyethylated stearic acid includes polyoxyethelene stearates, also known as macrogol stearates, comprise a series of polyethoxylated derivatives of stearic acid. They generally include polyethylene glycol stearates and polyethylene glycol distearates. Some polyethoxylated stearic acids suitable for use in the present disclosure include polyoxyl 2 stearate, polyoxyl 4 stearate, polyoxyl 6 stearate, polyoxyl 8 stearate, polyoxyl 12 stearate, polyoxyl 20 stearate, polyoxyl 2 stearate, polyoxyl 30 stearate, polyoxyl 40 stearate, polyoxyl 50 stearate, polyoxyl 100 stearate, polyoxyl 2 stearate, polyoxyl 150 stearate, polyoxyl 4 distearate, polyoxyl 8 distearate, polyoxyl 12 distearate, polyoxyl 32 distearate, and polyoxyl 150 distearate. Macrogol stearates are commercially available from several suppliers, under trade names including MYRJ (Croda), HODAG (Calgene) KESSCO (Stepan Co.) and PROTAMATE (Protameen Chemicals).

Other suitable surfactants include polysorbate 80 (Tween 80), Solutol HS-15, d-tocopheryl polyethylene glycol 1000 succinate (TPGS), Polyoxyl 8 stearate (PEG 400 monosterate), and Polyoxyl 40 stearate (PEG 1750 monostearate).

Fatty acid esters are suitable surfactants. Among these, propylene glycol fatty acid esters and sorbitan fatty acid esters are suitable nonionic surfactants, and include monoesters, sesqui-esters, and di-esters. Sorbitan fatty acid esters may further include tri-esters. The fatty acid portion of these esters are typically $C_{12}$-$C_{18}$. Preferred fatty acid portions include stearate, isostearate, laurate, palmitate and oleate. Some preferred esters include sorbitan monooleate, propylene glycol monolaurate and sorbitan monolaurate.

Fatty acid esters (preferably $C_{12}$-$C_{18}$) of carboxylic acids are also preferred. These include esters of lactic acid, malic acid, adipic acid, and myristic acid. Some suitable surfactants include Ceraphyl 31 (lauryl lactate ester, Ashland Inc.), Labrafac PG (propylene glycol dicaprylate/dicaprate NF, Gattefosse), and Lauroglycol 90 (Propylene glycol monolaurate (type II) EP/NF; Gattefosse).

Other suitable surfactants include PEG 300 caprylic/capric glycerides (Softigen 767), PEG 300 linoleic glycerides (Labrafil M-2125CS), Glyceryl monooleate (PECEOL), Propylene glycol monolaurate (Lauroglycol FCC).

When a surfactant is used, any suitable amount may be used. Pharmaceutical compositions of the present disclosure may comprise up to 50 wt % surfactant, up to 40 wt % surfactant, up to 30 wt % surfactant, up to 20 wt % surfactant, up to 10 wt % surfactant, up to 5 wt % surfactant, up to 4 wt % surfactant, up to 3 wt % surfactant, up to 2 wt % surfactant, up to 1.5 wt % surfactant, or up to 1 wt % surfactant, based on weight of the composition. Pharmaceutical compositions of the present disclosure comprising surfactant will typically comprise at least 0.01 wt % surfactant, at least 0.1 wt % surfactant, at least 0.2 wt % surfactant, at least 0.4 wt % surfactant, at least 0.6 wt % surfactant, or at least 0.8 wt % surfactant, based on weight of the composition. For example, the amount of surfactant may be from 0.01 wt % to 5 wt %, from 0.2 wt % to 3 wt %, or from 0.6 wt % to 2 wt %.

Some of these excipients have multiple functions, e.g., as hydrophobic solvents and/or surfactants. When a component has multiple functions, e.g., a macromolecule having surfactant properties (e.g., poloxamer, polyethoxylated castor oil, etc.) the component can be apportioned among the functions, e.g., surfactant and polymer components, or can be classified solely with one of the components.

Compositions of the present disclosure optionally comprise at least one antioxidant, preferably an antioxidant suitable for use in ophthalmic depots. Antioxidants are especially preferred when the depot may be subject to oxidation at the situs of administration. For example, a vitreal depot may be exposed to light, and may therefore be subject to photo-initiated free radical formation, such that it may be preferable to include an anti-oxidant capable of neutralizing free radicals. In such embodiments, the at least one antioxidant preferably comprises a tocopherol, a tocotrienol, or combinations thereof. The antioxidant is preferably soluble in the compositions of the present disclosure. Other suitable antioxidants may include one or more of glutathione, lipoic acid, uric acid, carotenes (e.g., vitamin A and its derivatives and analogs), melatonin, ubiquinol (coenzyme Q), ascorbic acid, sodium thiosulfate, cysteine, sodium edetate, ascorbyl palmitate, butylated hydroxyanisole (BHA), butylated hydroxytoluene (BHT), propyl gallate, monothioglycerol, tert-butylhydroquinone (TBHQ), and potassium metabisulfite. Tocopherols and their derivatives and analogues are preferred, of which vitamin E is preferred. Vitamin E includes all forms of tocopherol with antioxidant properties, and includes vitamin E acetate, α-tocopherol and γ-tocopherol; and includes D-, L-, and DL-forms, such as DL-α-tocopherol.

When an antioxidant, e.g., a tocopherol, is used, it can be present in any amount that will confer useful antioxidant properties to the composition for a suitable period of time. A preferred period of time is for the shelf life of the product, e.g., up to its expiration date. Preferred periods of time include 3 months, 6 months, 12 months or 1 year, 18 months or 1.5 years, 24 months or 2 years, 30 months or 2.5 years, 3 years, and 4 years.

When used, the antioxidant is preferably present in an amount up to 50 wt %, 10 wt %, 5 wt %, 1 wt %, 0.1 wt %, or 0.01 wt % based on weight of the composition. Preferred ranges include those formed from these values and/or values in the Examples. In some cases, vitamin E is present in an amount ranging from 0.1 wt % to 5 wt %, based on weight of the composition.

When used in an ophthalmic depot formulation, the HVLCM, preferably SAIB, appears to have several unexpected beneficial properties. While the HVLCM, e.g., SAIB, regulates viscosity and/or cohesiveness of the depot, its presence also contributes to an extended intra-vitreous release profile, over which the density of the depot can remain such that it does not float. Including at least about 0.5 wt % of the HVLCM can be particularly advantageous.

In a preferred embodiment, the HVLCM significantly decreases in viscosity when mixed with a solvent to form a low viscosity liquid carrier vehicle that can be combined with an API to form a pharmaceutical composition. The low viscosity pharmaceutical composition is typically easier to place in the body than a high viscosity composition, because, for example, it flows more easily into and out of syringes or other implantation means. The pharmaceutical composition can have any desired viscosity. It has been found that a viscosity range for the pharmaceutical composition of less than approximately 400 cP, and more particularly less than 200 cP, less than 100 cP, less than 50 cP, or less than 25 cP, at 25° C. and 1 atmosphere, is typically useful for in vivo applications. Though there is no lower target viscosity, the viscosity will generally be at least 1 cP, at least 2 cP, at least 4 cP, at least 6 cP, at least 8 cP, at least 10 cP, or at least 15 cP, at 25° C. and 1 atmosphere.

In compositions comprising SAIB and vitamin E (VE), any weight ratio of SAIB:VE can be used that provides a safe and effective composition. In some aspects of the present invention, the weight ratio of SAIB:VE can be chosen to control the density of the composition (density prior to use, upon injection, and long-term (e.g., at 1, 2, 4, 6 or 12 months)). For example, in an ophthalmic depot composition comprising SAIB and VE, the weight ratio SAIB:VE can be 10, 7.5, 5, 3, 2, 1, 0.8, 0.6, 0.5, 0.4, 0.3, or 0.2. Each of these values can be an open or closed upper or lower limit on the ratio of SAIB:VE (e.g., "at least 1," or "less than 1"). Suitable ranges (with open or closed endpoints) of the weight ratio of SAIB:VE include ranges formed from any pair of these values. For example, the weight ratio of SAIB:VE can be 0.5-10, 0.5-5, 0.5-2, or 1-3. One way to select a SAIB/VE ratio is to assume the composition does not contain any other excipient which can remain in the vitreous (e.g., so that the composition does not float in the vitreous).

In some cases it may be advantageous for a pharmaceutical composition to have low peroxide content, since peroxides are known potent oxidizing agents, and can lead to chemical instability. It may be advantageous in such cases to prepare pharmaceutical compositions from components that have low peroxide content. It is known that a SAIB manufacturing process can lead to peroxide production. When a low peroxide pharmaceutical composition comprising SAIB is required or desired, it may be advantageous to use a low-peroxide SAIB. Low peroxide SAIB is disclosed in U.S. patent publication 2012/0330005, the disclosure of which is incorporated herein by reference in its entirety.

When light encounters a material, they can physically interact with each other in several different ways. These interactions depend on the nature of the light (its wavelength, frequency, energy, etc.) and the nature of the material. Light waves generally interact with an object by some combination of e.g., absorption, reflection, and transmittance/refraction. Transparency is the physical property of allowing light to pass non-diffusively through a material. Translucency refers to the property of allowing light to pass diffusively through a material. Opacity refers to the property of not permitting light to pass through a material. An optically transparent material allows much of the light that falls on it to be transmitted, with little light being diffused, reflected or absorbed. Materials that do not allow the transmission of light are called opaque.

In certain aspects of the present disclosure, such as intravitreal depots, optical transparency of the pharmaceutical composition is a beneficial and preferred property. In other aspects, the pharmaceutical composition is preferably translucent or opaque. When optical transparency is desired, compositions of the present disclosure may non-diffusively transmit at least about 75% of the light, about 80% of the light, about 85% of the light, about 90% of the light, about 95% of the light. Compositions of the present disclosure may non-diffusively transmit up to 100% of the light, 99% of the light, 98% of the light, 97% of the light, or 96% of the light. The percentage of light non-diffusively transmitted may be measured at specific frequencies (e.g., 420-440 nm, 535-555 nm, and/or 565-580 nm), or averaged across the visible spectrum.

The compositions of the present disclosure may be sterile filtered.

Compositions of the present disclosure may be stored under various conditions. For instance, compositions of the present disclosure may be stored at a temperature ranging from about 0° C. to about 30° C., such as about 2° C. to about 25° C., about 4° C. to about 20° C., about 5° C. to about 15° C., or about 7° C. to about 10° C. The compositions of the present disclosure may be stored in various containers, e.g., glass containers.

Compositions of the present disclosure may be used to treat any condition treatable with a topical composition or liquid depot. Ophthalmic conditions that may be treatable with sirolimus include conditions disclosed in U.S. Pat. No. 8,367,097, which is incorporated by reference herein in its entirety. The depot formulation of the present disclosure may be useful as a medicine, e.g., for eye diseases, e.g., age-related macular degeneration, retinopathia diabetica, prematurity retinopathy, occlusion of retinal vein, occlusion of retinal artery, polypoidal choroidal vasculopathy, retinal angiomatous proliferation, myopic choroidal neovascularization, diabetic macular edema, eye tumor, radiation retinopathy, rubeosis iridis, rubeotic glaucoma, proliferative vitreoretinopathy (PVR), primary open-angle glaucoma, secondary open-angle glaucoma, normal tension glaucoma, hypersectretion glaucoma, primary angle-closure glaucoma, secondary angle-closure glaucoma, plateau iris glaucoma, combined mechanism glaucoma, developmental glaucoma, steroid induced glaucoma, exfoliation glaucoma, amyloidotic glaucoma, rubeotic glaucoma, malignant glaucoma, glaucoma capsulare of crystalline lens, plateau iris syndrome, hypertonia oculi, uveitis, intraocular infection, etc. As the disease, it can more preferably be used as a preventative or therapeutic agent for age-related macular degeneration, diabetic retinopathy, primary open-angle glaucoma, normal tension glaucoma, primary angle-closure glaucoma, ocular hypertension, uveitis, intraocular infection, etc. Preferred conditions include uveitis, wet and dry age-related macular degeneration (AMD), diabetic macular edema (DME), diabetic retinopathy (DR) and keratomycosis.

When used ophthalmically, the compositions of the present disclosure may be applied as vitreous and/or subconjunctival depots.

Typically, the composition will be injected from a standard hypodermic syringe, a catheter or a trocar, that has been pre-filled with the pharmaceutical composition. It is often preferred that injections take place using the smallest size needle (i.e., smallest diameter) or catheter to reduce discomfort to the subject when the injection is in ophthalmic, subcutaneous, intramuscular, intravascular (high/low flow), intramyocardial, adventitial, intratumoral, or intracerebral portion, wound sites, tight joint spaces or body cavity of a human or animal. In some cases, the administration comprises intravitreal injection and/or subconjunctival injection. Any needle or catheter size appropriate for the injection site may be used. A higher gauge size is generally preferred (e.g., in order to reduce pain or damage). However, an excessively high gauge may result in complications, such as prolonged injection times or increased injection force due to capillary action and/or viscosity. It is desirable to be able to inject the pharmaceutical composition through a needle or a catheter ranging from 16 gauge and higher, 20 gauge and higher, 22 gauge and higher, 24 gauge and higher, 25 gauge and higher, 26 gauge and higher, 27 gauge and higher, 28 gauge and higher, or 29 gauge and higher. The needle or catheter will typically be 34 gauge and lower, 33 gauge and lower, 32 gauge and lower, 31 gauge and lower, or 30 gauge and lower.

When a syringe is used, any needle length appropriate for the injection site can be used. The needle is preferably long enough to permit the tip to effectively reach the target depot site. The needle is preferably short enough for the operator (e.g., physician or nurse), to maintain control over the syringe and/or injection procedure. For ophthalmic depots, a needle can be at least 0.5 cm, 1 cm, 1.5 cm, or 2 cm in length. For ophthalmic depots, a needle can be up to 4 cm, 3 cm, or 2.5 cm in length.

A person of ordinary skill in the art can determine an appropriate needle size (e.g., gauge and/or length) using the present specification as a guide.

In the case of successively administering the depot formulation of the present disclosure, there is no particular limitation in dosage interval so long as the interval is sufficient to exert the desired drug efficacy; however, being administered at an interval of once in 3 days to once in 5 years may be preferable, such as once a month to once every 9 months, or once every 6 months to once every 8 months. For instance, the composition may be administered at an interval of once in 3 days, once in 5 days, once in 1 week, once in 2 weeks, once in 1 month, once in 2 months, once in 3 months, once in 4 months, once in 5 months, once in 6 months, once in 7 months, once in 8 months, once in 9 months, once in 1 year, once in 2 years, once in 3 years, once in 4 years or once in 5 years may be preferable, and being administered at an interval of once in 2 months, once in 3 months, once in 4 months, once in 5 months, once in 6 months or once in 1 year is often preferable. In addition, the dosage interval can be changed as appropriate.

EXAMPLES

Materials cited in the examples below are commercially available from a number of sources. Some commercial suppliers are disclosed herein. Other commercial suppliers may be available for the products. Naming a possible commercial supplier of a product does not in any way limit the present disclosure.

Polymers (PLGA: dodecanol initiated, L/G 85/15, MW 13.9 KDa), (PLA: dodecanol initiated, MW 13.9 KDa) and (polycaprolactone PCL: dodecanol initiated MW 95.3 KDa) are commercially available as LACTEL brand from Durect Corporation. SAIB was obtained from Durect Corporation.

Solvents include benzyl alcohol (BA), benzyl benzoate, propylene glycol, and dehydrated undenatured 200 proof ethanol, USP grades, such as commercially available from Spectrum Chemicals. N-methyl-2-pyrrolidone (NMP) is commercially available from ISP. Super Refined PEG 400-LQ-(MH) is commercially available from CRODA, and dimethyl sulfoxide (DMSO) is commercially available from Gaylord. Castor oil is commercially available from Spectrum Chemicals. KolliSolve® GTA (Triacetin) is commercially available from BASF, and triethyl citrate (TEC) 99% is commercially available from Sigma Aldrich. High purity acetyl tributyl citrate (ATBC) NF, USP Grade is commercially available from Mutchler Inc.

Synperonic PE/F68-FL-CQ (Poloxamer 188) is commercially available from CRODA. Dulbecco's phosphate buffered saline (PBS), hyaluronic acid (HA) and sodium dodecyl sulfate (SDS), commercially available from Sigma-Aldrich, are used in release media preparation.

Vitamin E (DL-α-tocopherol) is commercially available from BASF.

Sirolimus is commercially available from Althea through Santen Pharmaceutical Company.

Example 1

Referring to Tables 1 and 2 below, the solubility of sirolimus was tested at room temperature in solvents and in mixtures of benzyl benzoate and ethanol.

TABLE 1

Solubility of Sirolimus in Aqueous Media and Solvents at Ambient Temperature

| Medium/Solvent | Solubility, mg/mL |
|---|---|
| PBS, pH 7.4 | Not detected |
| PBS, 0.1% SDS, pH 7.4 | 0.23 |
| PEG 400 | 10.7 |
| Benzyl alcohol (BA) | ≥387 |
| N methyl-2 Pyrrolidone (NMP) | ≥284 |
| Dimethyl sulfoxide (DMSO) | ≥243 |
| Propylene glycol | 11.8 |
| Castor oil | 3.0 |
| Ethanol (EtOH) | 48.5 |
| Benzyl benzoate (BB) | 37.0 |

TABLE 2

Solubility of Sirolimus in Benzyl Benzoate/Ethanol

| BB/EtOH Ratio | Solubility, mg/mL |
|---|---|
| 7 | 162.9 |
| 9 | 125.2 |
| 16 | 90.1 |
| 18 | 85.6 |

Referring to Table 4 below, sirolimus (SRL) was dissolved in various solvents and concentration tested after 8 days at room temperature. Samples were protected from light but were exposed to ambient humidity.

Chemical Stability Testing:

About 2 mL of sirolimus formulations were placed in respective 2 mL crimp sealed glass vials under ambient humidity and stored at 5° C. and 25° C. protected from light exposure. Samples were analyzed by HPLC to determine sirolimus concentration. HPLC instrument and parameters were as follows:

| | |
|---|---|
| Column Oven | Agilent 1100 Thermostatted Column Compartment |
| Pump | Agilent 1100 Quaternary gradient pump with built in Vacuum Degasser |
| Detector | Agilent 1100 UV or Diode Array Detector |
| Refrigerated Autosampler | Agilent 1100 |
| Column | YMC ODS-AQ, 4.6 × 250 mm |

Mobile Phase:
A: 20 mM ammonium formate at pH 4.0
B: Acetonitrile

Gradient Table

| Time, minutes | 0 | 18 | 40 | 45 | 50 | 51 | 60 |
|---|---|---|---|---|---|---|---|
| % B | 65 | 65 | 70 | 90 | 90 | 65 | 65 |
| Flow Rate, mL/min | 0.5 | 0.5 | 1.0 | 1.0 | 1.0 | 0.5 | 0.5 |

Detection: λ = 276 nm

Column Temperature: 50° C.

Preparation of Sirolimus Solution Formulations:

Polymers, at the weight ratios shown in Table 5, were dissolved in solvents/mixture of solvents and mixed until uniform. SAIB, at the weight ratios shown in Table 5, was added to polymer/solvent solutions and mixed at 50° C. until a uniform solution was formed. Sirolimus at 3 wt % to 5 wt % concentration was dissolved in each vehicle.

In Vitro Drug Release Testing:

Between 50-100 μL sirolimus formulation was injected in 5 mL release medium (PBS including 0.1% SDS or 0.05% HA) equilibrated at 37° C. Samples were placed on an orbital shaker rotating at 30 rpm or 50 rpm at 37° C. Sampling was conducted by withdrawing the entire release medium at different time points (e.g. 1, 4, 8, 24 hrs and up to 50 days for some formulations) and replacing with a fresh release medium solution equilibrated at 37° C. Care was taken not to touch the drug depot during sampling. Samples were analyzed by HPLC to determine concentration of sirolimus.

Example 1 Results

Solubility of Sirolimus in Aqueous Media and Solvents:

Addition of 0.1% SDS enhances the aqueous solubility of sirolimus in PBS (Table 1). Solubility of Sirolimus increased in mixtures of benzyl benzoate/ethanol compared with solubility in benzyl benzoate or ethanol. As seen in Table 2, the highest solubility was observed when the ratio of benzyl benzoate/ethanol was 7.

Chemical Stability of Sirolimus in Release Testing Media and Compatibility with Solvents:

Table 3 shows the stability in PBS containing 0.1% SDS for use as the release medium for drug release testing. Compatibility of solvents with sirolimus was tested. Table 4 shows sirolimus recovery after storage in solvents at room temperature.

TABLE 3

Chemical Stability of Sirolimus in Drug Release Testing Medium at 37° C.

| Buffer | Time, Days | Concentration, μg/mL | % Drug Remained | % Drug Remained including all Deg Peaks |
|---|---|---|---|---|
| PBS, 0.1% SDS | T0 | 5.44 | — | — |
|  | 4 | 4.47 | 82.2 | 93.8 |
| PBS, 0.1% SDS, 0.01% BHT | T0 | 5.72 | — | — |
|  | 4 | 4.70 | 82.1 | 90.6 |

TABLE 4

Chemical Stability of Sirolimus in Solvents

| Solvent | Theoretical Concentration, mg/mL | Concentration mg/mL, 8 days at RT | % SRL Recovered Based on Theoretical Concentration |
|---|---|---|---|
| Ethanol (EtOH) | 27.7 | 28.2 | 101.8 |
| PEG 400 | Solubility sample with excess solid | 10.7 | 104.9[1] |
| Benzyl benzoate (BB) | 22.1 | 22.3 | 101.8 |
| Benzyl alcohol (BA) | 43.1 | 42.3 | 98.1 |
| N-methyl-2-pyrrolidone (NMP) | 32.9 | 30.3 | 92.1 |
| Dimethyl sulfoxide (DMSO) | 30.3 | 30.9 | 101.9 |

[1]Based on T0 assayed value

Figure 1A:
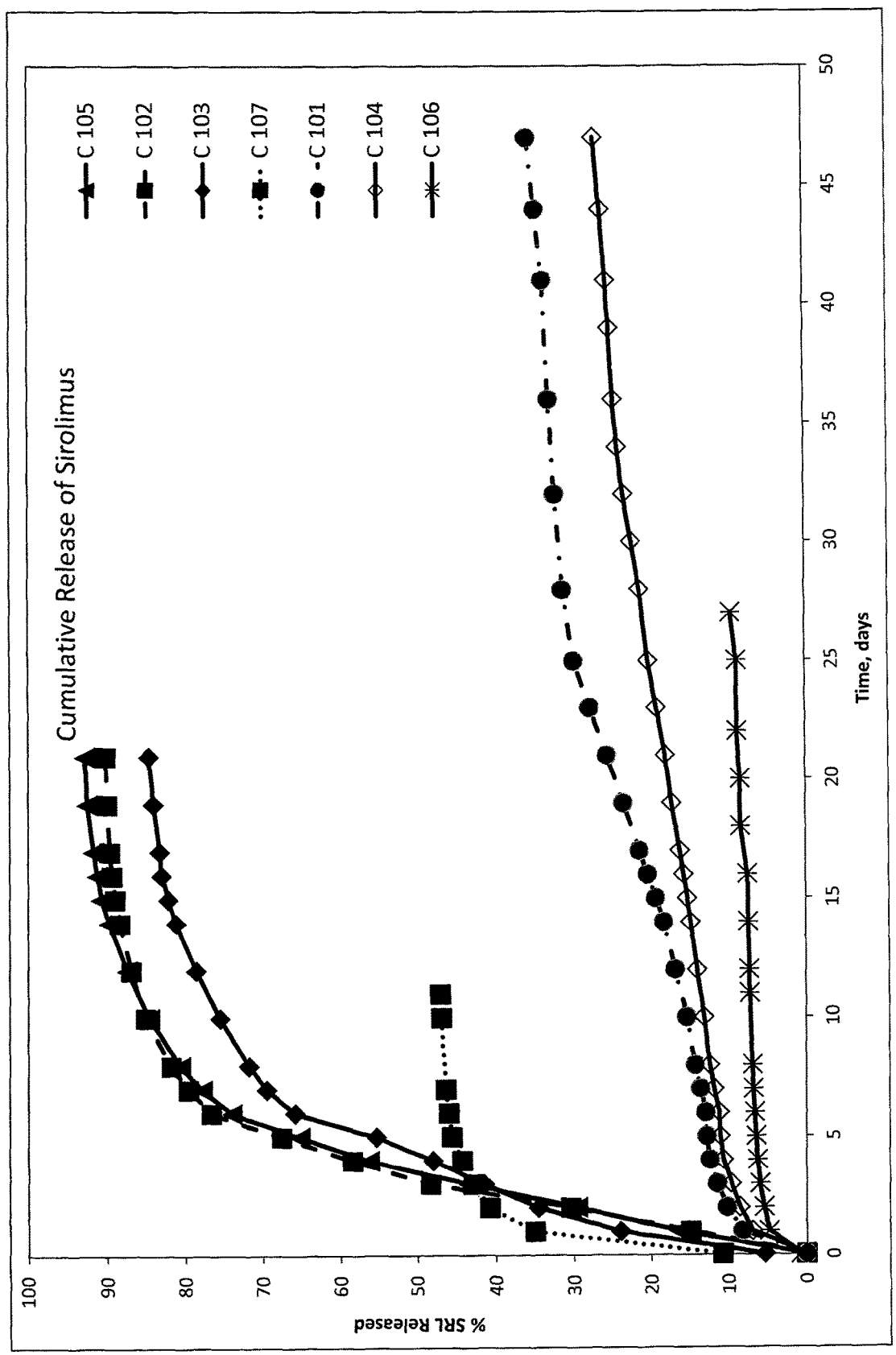
Figure 1B:
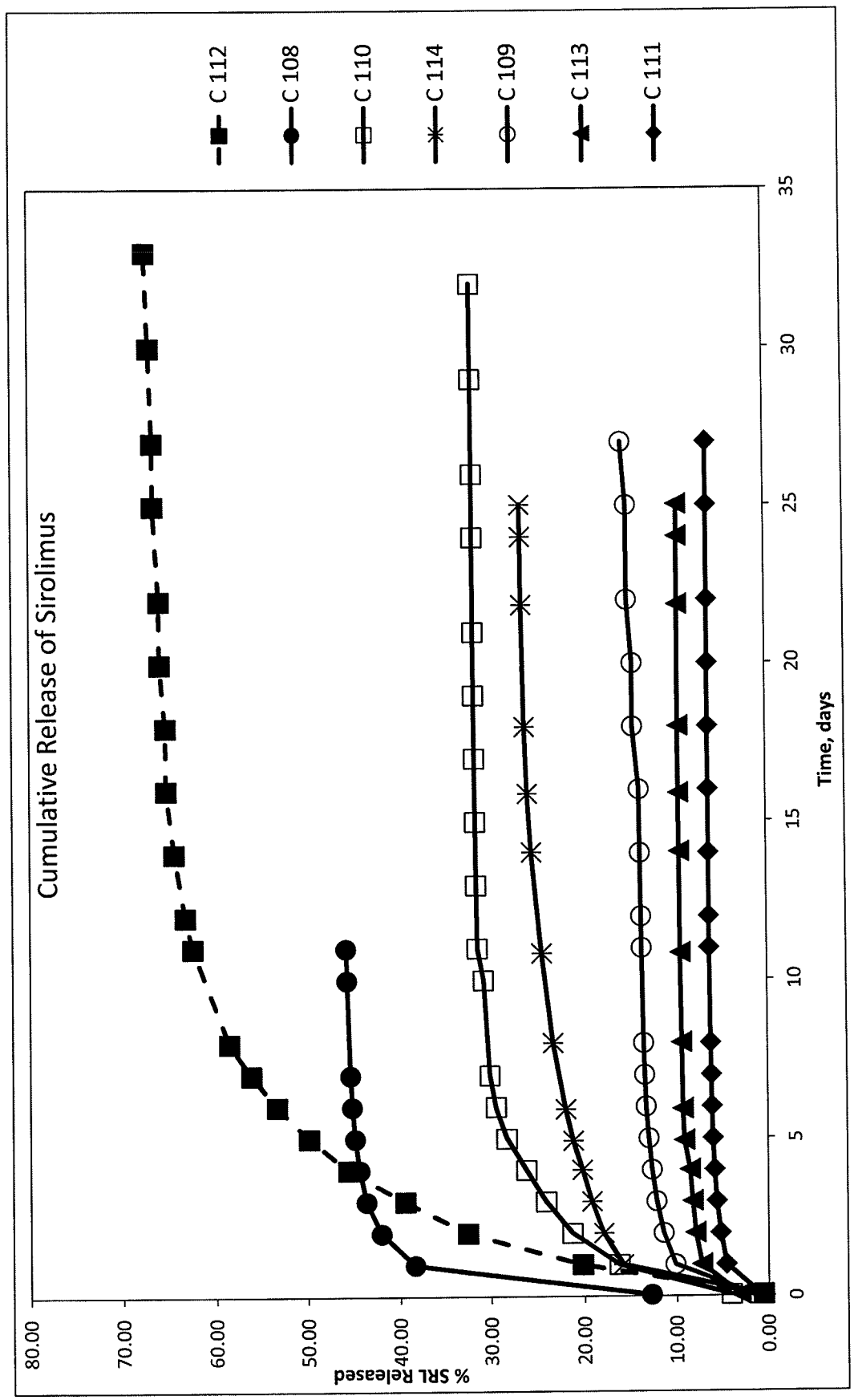
Figure 1C:
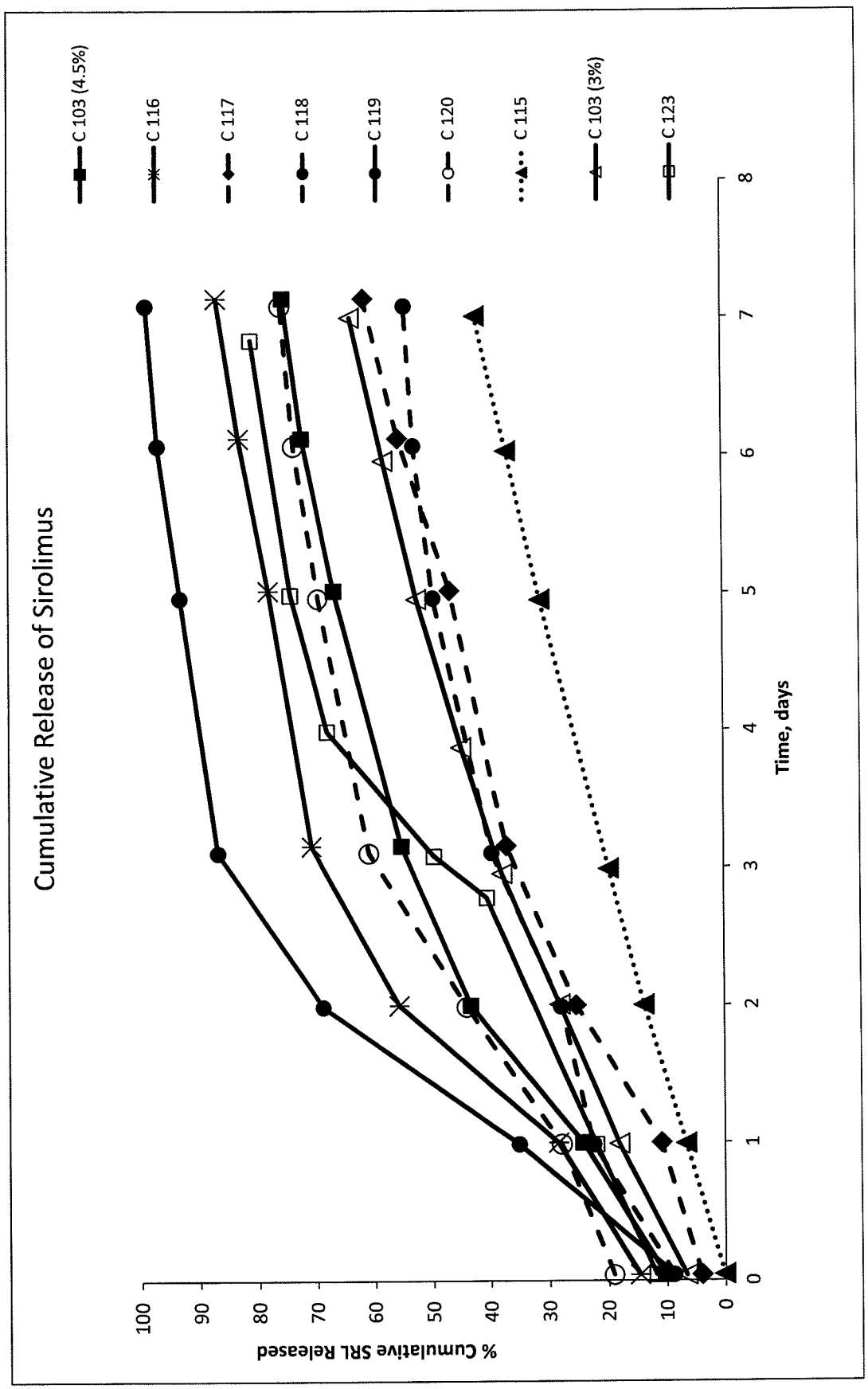
Figure 2:
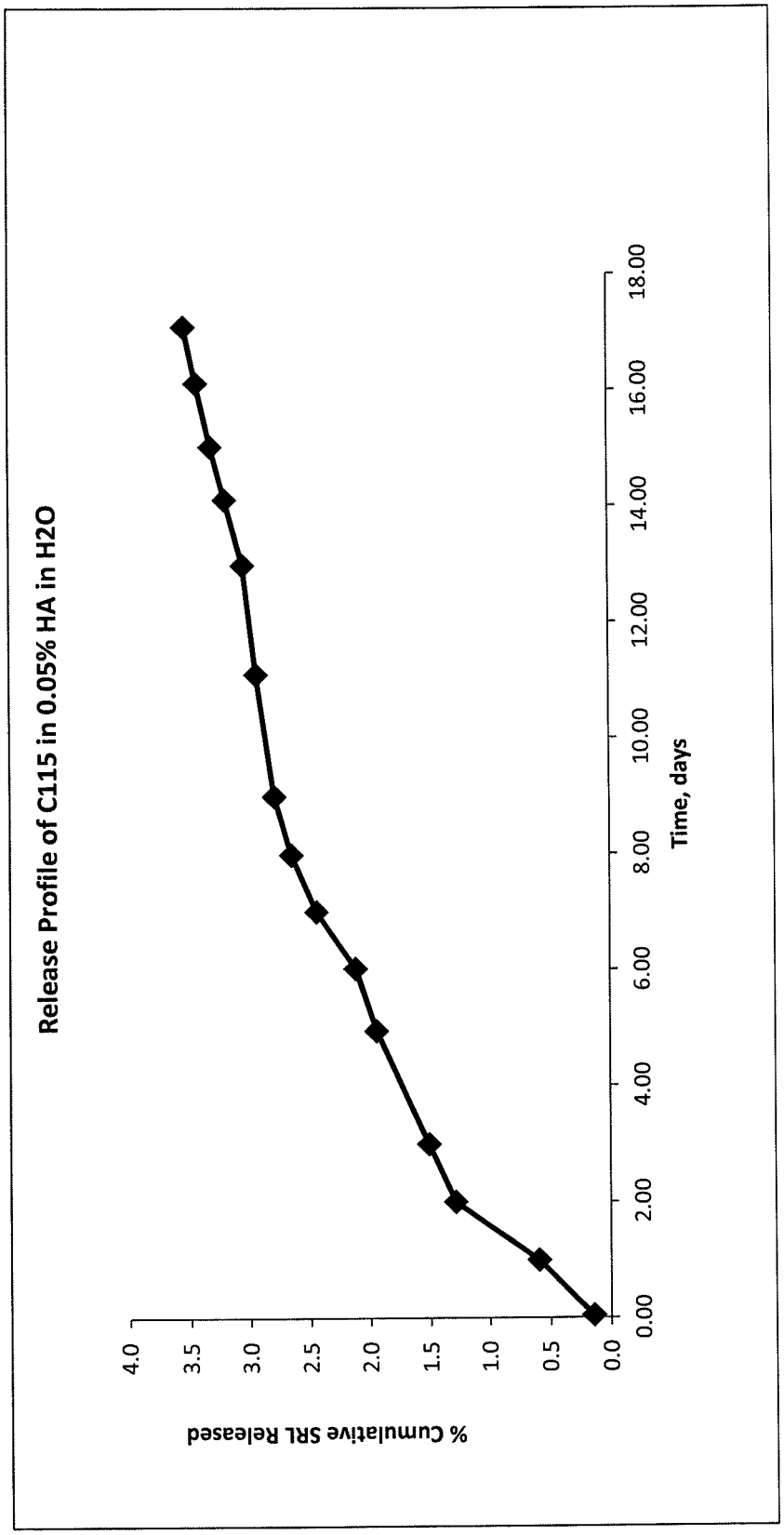
FIG. 2 shows in vitro drug release from a composition of the present disclosure in 0.05% hyaluronic acid (HA) medium.

Evaluation of Prototype Formulations:

Sirolimus solution formulations had low viscosity (injectable through 27 G and 30 G needles). In vitro drug release testing in PBS, 0.1% SDS showed drug release for ≥50 days at 37° C. (FIGS. 1a, 1b, and 1c) and ≥18 days in HA, FIG. 2 (tested only for composition C115). In FIG. 1, composition C105b used vehicle V105, but had a sirolimus concentration of 4.5 wt %.

Table 6 data indicates that sirolimus was stable in the formulations exposed to ambient humidity for minimum of 2 months at 25° C. and 5° C., except for formulations containing NMP (C107, C108, and C110). Storage at 25° C. and 5° C. is preferred condition for commercial products. For preferred composition of the present disclosure, there is no need to store sirolimus formulations under inert conditions and/or at sub-zero temperatures.

The vehicles and pharmaceutical compositions listed in below Tables 5 and 6 were made.

TABLE 5

Vehicles Comprising SAIB

| Vehicle Formulations | Composition of Vehicles (Parts by Weight) |
|---|---|
| V101 | SAIB/BA/PLA (10/80/10) |
| V102 | SAIB/BA/BB/PLA (10/40/40/10) |
| V103 | SAIB/BB/EtOH/PLGA (10/70/10/10) |
| V104 | SAIB/BA/PLGA (10/80/10) |
| V105 | SAIB/BA/BB/PLGA (10/40/40/10) |
| V106 | SAIB/BA/PLA (10/70/20) |
| V107 | SAIB/NMP/PLA (10/70/20) |
| V108 | SAIB/PEG 400/NMP/PLA (10/20/50/20) |
| V109 | SAIB/PEG 400/BA/PLA (10/20/50/20) |
| V110 | SAIB/PG/NMP/PLA (10/20/50/20) |
| V111 | SAIB/PG/BA/PLA (10/20/50/20) |
| V112 | SAIB/BA/BB/PLA (10/60/10/20) |
| V113 | SAIB/NMP/BA/PLA (10/40/30/20) |
| V114 | SAIB/BA/PCL (10/85/5) |
| V115 | SAIB/BB/PEG400/EtOH/PLA (10/40/43/2/5) |
| V116 | SAIB/BB/EtOH (50/45/5) |
| V117 | SAIB/BB/DMSO/PLGA (10/75/10/5) |
| V118 | SAIB/PEG400/DMSO/PLGA (10/50/35/5) |
| V119 | SAIB/BB/DMSO (60/35/5) |
| V120 | SAIB/PEG400/DMSO (46.4/23.0/30.6) |
| V121 | SAIB/BB/PEG400/DMSO/PLGA (9.6/38.4/41.2/6.0/4.8) |
| V122 | SAIB/BB/PEG400/DMSO (14.7/39.1/42.1/4.1) |
| V123 | SAIB/BB/EtOH/PCL (15/78/5/2) |
| V124 | SAIB/BB/PEG 400/EtOH (50/25/20/5) |
| V125 | SAIB/BB/PEG 400/EtOH (50/33/15/2) |
| V126 | SAIB/BB/PEG 400/EtOH (45/35/15/5) |

TABLE 6

Pharmaceutical Compositions Comprising SAIB

| Pharmaceutical Composition Formulations | Pharmaceutical Composition (Parts by Weight) |
|---|---|
| C101 | SAIB/BA/PLA/SRL (9.7/77.6/9.7/3) |
| C102 | SAIB/BA/BB/PLA/SRL (9.7/38.8/38.8/9.7/3) |
| C103 | SAIB/BB/EtOH/PLGA/SRL (9.7/67.9/9.7/9.7/3) |
| C104 | SAIB/BA/PLGA/SRL (9.7/77.6/9.7/3) |
| C105 | SAIB/BA/BB/PLGA (9.7/38.8/38.8/9.7/3) |
| C106 | SAIB/BA/PLA/SRL (9.7/67.9/19.4/3) |
| C107 | SAIB/NMP/PLA/SRL (9.7/67.9/19.4/3) |
| C108 | SAIB/PEG 400/NMP/PLA/SRL (9.7/19.4/48.5/19.4/3) |
| C109 | SAIB/PEG 400/BA/PLA/SRL (9.7/19.4/48.5/19.4/3) |
| C110 | SAIB/PG/NMP/PLA/SRL (9.7/19.4/48.5/19.4/3) |
| C111 | SAIB/PG/BA/PLA/SRL (9.7/19.4/48.5/19.4/3) |
| C112 | SAIB/BA/BB/PLA/SRL (9.7/58.2/9.7/19.4/3) |
| C113 | SAIB/NMP/BA/PLA/SRL (9.7/38.8/29.1/19.4/3) |
| C114 | SAIB/BA/PCL/SRL (9.7/82.4/4.9/3) |
| C115 | SAIB/BB/PEG400/EtOH/PLA/SRL(9.7/38.8/41.7/1.9/4.9/3) |
| C116 | SAIB/BB/EtOH/SRL (48.5/43.6/4.9/3) |
| C117 | SAIB/BB/DMSO/PLGA/SRL (9.7/72.7/9.7/4.9/3) |
| C118 | SAIB/PEG400/DMSO/PLGA/SRL (9.7/48.5/33.9/4.9/3) |
| C119 | SAIB/BB/DMSO/SRL (58.2/33.9/4.9/3) |
| C120 | SAIB/PEG400/DMSO/SRL (45/22.3/29.7/3) |
| C121 | SAIB/BB/PEG400/DMSO/PLGA/SRL (9.3/37.2/40/5.8/4.7/3) |
| C122 | SAIB/BB/PEG400/DMSO/SRL (14.3/37.9/40.8/4.0/3) |
| C123 | SAIB/BB/EtOH/PCL/SRL (14.5/75.6/4.9/2/3) |
| C124 | SAIB/BB/PEG 400/EtOH/SRL (48.5/24.2/19.4/4.9) |
| C125 | SAIB/BB/PEG 400/EtOH/SRL (48.5/32/14.6/1.9/3) |
| C126 | SAIB/BB/PEG 400/EtOH/SRL (43.6/34/14.5/4.9/3) |

TABLE 7

Chemical Stability in Prototype Formulations

| Pharmaceutical Composition Formulations | Time, weeks | % SRL Remained at 5° C. | % SRL Remained at 25° C. |
|---|---|---|---|
| C101 | 9 | — | — |
| C102 |  | 95.2 | 90.4 |
| C103 |  | 95.8 | 93.7 |
| C104 |  | 95.2 | 86.8 |
| C105 |  | 95.9 | 90.1 |
| C106 | 7 | 94.9 | 92.5 |
| C107 |  | 78.6 | 15.1 |
| C108 |  | 85.9 | 15.0 |
| C109 |  | 95.5 | 93.9 |
| C110 |  | 95.8 | 63.7 |
| C111 |  | 96.4 | 93.9 |
| C112 |  | 97.7 | 90.9 |
| C113 | 4 | 97.1 | 96.8 |
| C114 |  | 95.3 | 92.0 |
| C115 | 18 | 98.3 | 90.9 |
| C116 | 2 | 97.7 | 97.7 |
| C117 | 2 | 98.0 | 96.0 |
| C118 | 2 | 98.0 | 94.7 |
| C119 | 2 | 97.7 | 98.4 |
| C120 | 2 | — | 99.7 |
| C121 | 1 | — | 99.6 |
| C122 | 1 | — | 99.9 |
| C123 | — | — | — |

Example 2

Preparation of Sirolimus Solution Formulations:

Poloxamer 188 was dissolved in mixture of benzyl benzoate and ethanol (weight ratios shown in Table 8) and mixed until uniform. SAIB (at weight ratios shown in Table 8) was added and mixed at 50° C. until a uniform solution was formed. After the solution cooled, triacetin or acetyl triethyl citrate (weight ratios shown in Table 8) was added and mixed thoroughly. Sirolimus at 3 wt % to 4.5 wt % weight was dissolved in each vehicle.

Chemical Stability Testing:

About 2 mL of sirolimus formulations were placed in respective 2 mL crimp sealed glass vials under ambient humidity and stored at 5° C. and 40° C., protected from light exposure.

Example 2 Results

In Vitro Testing:

Tested formulation compositions are listed in Table 9.

TABLE 8

Composition of Vehicles Containing Poloxamer 188

| Vehicle Formulations | Composition of Vehicles (Parts by Weight) |
|---|---|
| V201 | SAIB/BB/EtOH/Poloxamer 188 (30/64/5/1) |
| V202 | SAIB/BB/EtOH/PEG 400/Poloxamer 188 (40/40/5/15/0.2) |
| V203 | SAIB/BB/EtOH/Poloxamer 188 (15/79/5/0.2) |
| V204 | SAIB/BB/EtOH/Poloxamer 188 (45/49/5/1) |
| V205 | SAIB/BB/EtOH/PEG 400/Poloxamer 188 (30/49/5/15/1) |
| V206 | SAIB/BB/EtOH/Poloxamer 188 (49/45/5/1) |
| V207 | SAIB/BB/EtOH/Acetyl triethyl citrate ATEC/Poloxamer 188 (1/45/5/48/1) |
| V208 | SAIB/BB/EtOH/triacetin/Poloxamer 188 (10/40/5/44/1) |
| V209 | SAIB/BB/EtOH/ATEC/Poloxamer 188 (10/40/5/44/1) |
| V210 | SAIB/BB/EtOH/ATEC/Poloxamer 188 (40/40/5/14/1) |
| V211 | SAIB/BB/EtOH/ATEC/Poloxamer 188 (1/45/5/48/1) |

TABLE 9

Composition of Formulations Containing Poloxamer 188

| Pharmaceutical Composition Formulations | Composition of Formulations (Parts by Weight) |
|---|---|
| C201 | SAIB/BB/EtOH/Poloxamer 188/SRL (29.1/62/4.9/1/3) |
| C202 | SAIB/BB/EtOH/PEG 400/Poloxamer 188/SRL (38.7/38.7/4.9/14.5/0.2/3) |
| C203 | SAIB/BB/EtOH/Poloxamer 188/SRL (14.4/77.5/4.9/0.2/3) |
| C204 | SAIB/BB/EtOH/Poloxamer 188/SRL (43.6/47.5/4.9/1/3) |
| C205 | SAIB/BB/EtOH/PEG 400/Poloxamer 188/SRL (29.1/47.5/4.9/14.5/1/3) |
| C206 | SAIB/BB/EtOH/Poloxamer 188/SRL (47.5/43.6/4.9/1/3) |
| C207 | SAIB/BB/EtOH/Acetyl triethyl citrate ATEC/Poloxamer 188/SRL (1/43.6/4.9/46.5/1/3) |
| C208 | SAIB/BB/EtOH/triacetin/Poloxamer 188/SRL (9.7/38.8/4.9/42.7/1/3) |
| C209 | SAIB/BB/EtOH/ATEC/Poloxamer 188/SRL (9.7/38.8/4.9/42.7/1/3) |
| C210 | SAIB/BB/EtOH/ATEC/Poloxamer 188/SRL (38.8/38.8/4.9/13.6/1/3) |
| C211 | SAIB/BB/EtOH/ATEC/Poloxamer 188/SRL (1/43.6/4.9/46.5/1/3) |

Table 10 shows the comparison of chemical stability data of formulations with and without Poloxamer.

TABLE 10

Chemical Stability of Sirolimus in Solution Formulations after 2 weeks

| Pharmaceutical Composition Formulations | % SRL Remained at 5° C. | % SRL Remained at 40° C. |
|---|---|---|
| C116 (no Poloxamer 188) | 100.3 | 86.1 |
| C204 (1% Poloxamer 188) | 101.0 | 94.3 |

Example 3

Viscosity Testing:

Viscosity of the vehicles was measured using Brookfield DVIII+ Programmable Rheometer. Measurements were done using cone and plate with CPE-52 spindle. Viscosities were measured at 25±0.5° C. maintained by Brookfield TC-602D Refrigerated Bath/Programmable Controller.

Chemical Stability Testing

About 2 mL of Sirolimus formulations were placed in respective 2 mL crimp sealed glass vials under ambient humidity and stored at 5° C., 25° C. and 40° C. protected from light exposure.

Preparation of Formulations

1% Poloxamer 188 was dissolved in mixture of benzyl benzoate and ethanol (shown in Table 13) and mixed until uniform. SAIB (at ratios shown in Table 13) was added and mixed at 50° C. until a uniform solution was formed. After cooling of the solution to room temperature, PEG 400 or acetyl tributyl citrate (ratios shown in Table 13) were added and mixed thoroughly. Vitamin E was added and mixed thoroughly. Sirolimus was added at 3% concentration and stirred until all dissolved.

The compositions listed in Table 11 were evaluated for viscosity, chemical stability and sirolimus release (up to 24 hours) in aqueous release medium. These compositions had low viscosities as shown in Table 12.

TABLE 11

| Pharmaceutical Composition Formulation | Composition of Formulations (Parts by Weight) |
|---|---|
| C301 | SAIB/BB/EtOH/PLXM/VE/SRL (46.5/43.6/4.9/1/1/3) |
| C302 | SAIB/BB/EtOH/VE/SRL (47.5/43.6/4.9/1/3) |
| C303 | SAIB/BB/EtOH/PEG 400/VE/SRL (9.7/38.8/4.9/42.7/1/3) |
| C304 | SAIB/BB/EtOH/ATBC/VE/SRL (1/43.6/4.9/46.5/1/3) |
| Further evaluation around Acetyl Tributyl Citrate (ATBC) formulation C304 | |
| Effect of SAIB (0, 10%) | C305 BB/EtOH/ATBC/VE/SRL (43.6/4.9/47.7/1/3) |
| | C306 SAIB/BB/EtOH/ATBC/VE/SRL (9.7/38.8/4.9/44.7/1/3) |
| Effect of PLXM (1%) | C307 SAIB/BB/EtOH/ATBC/VE/PLXM/SRL (1/42.7/4.9/46.5/1/1/3) |
| Effect of Vitamin E (0, 10%) | C308 SAIB/BB/EtOH/ATBC/SRL (1/43.6/4.9/47.9/3) |
| | C309 SAIB/BB/EtOH/ATBC/VE/SRL (1/38.8/4.9/42.7/9.7/3) |

TABLE 12

| Pharmaceutical Composition Formulation | Vehicle Composition (Parts by Weight) | Shear Rate, 1/s | Viscosity, cP |
|---|---|---|---|
| C301 | SAIB/BB/EtOH/PLXM/VE (48/45/5/1/1) | 50 | 41 |
| | | 362 | 43 |
| C302 | SAIB/BB/EtOH/VE (49/45/5/1) | 46 | 45 |
| | | 340 | 46 |
| C303 | SAIB/BB/EtOH/PEG 400/VE (10/40/5/44/1) | 80 | 29 |
| | | 500 | 29 |
| C304 | SAIB/BB/EtOH/ATBC/VE (1/45/5/48/1) | 200 | 11 |
| | | 500 | 11 |
| C305 | BB/EtOH/ATBC/VE (45/5/49/1) | 200 | 11 |
| | | 500 | 12 |
| C306 | SAIB/BB/EtOH/ATBC/VE (10/40/5/44/1) | 150 | 14 |
| | | 500 | 14 |
| C307 | SAIB/BB/EtOH/ATBC/VE/PLXM (1/44/5/48/1/1) | 156 | 13 |
| | | 500 | 15 |
| C308 | SAIB/BB/EtOH/ATBC (1/45/5/49) | 200 | 11 |
| | | 500 | 11 |
| C309 | SAIB/BB/EtOH/ATBC/VE (1/40/5/44/10) | 160 | 14 |
| | | 500 | 14 |

Chemical stabilities of sirolimus formulations after 1 and 2 weeks storage at 5° C., 25° C. and 40° C. are listed in Table 13.

TABLE 13

| Formulation Composition Formulation | Vehicle Composition (Parts by Weight) | Temp. ° C. | Time, weeks | % SRL | % SRL Remained |
|---|---|---|---|---|---|
| C301 | SAIB/BB/EtOH/PLXM/VE/SRL (46.5/43.6/4.9/1/1/3) | NA | T0 | 3.08 | 100.0 |
| | | 5 | 2 | 3.08 | 100.0 |
| | | 25 | 2 | 3.04 | 98.7 |
| | | 40 | 1 | 2.92 | 94.8 |
| | | | 2 | 2.80 | 90.9 |
| C303 | SAIB/BB/EtOH/PEG 400/VE/SRL (9.7/38.8/4.9/42.7/1/3) | NA | T0 | 3.05 | 100.0 |
| | | 5 | 2 | 3.03 | 99.3 |
| | | 25 | 2 | 3.04 | 99.7 |
| | | 40 | 1 | 3.03 | 99.3 |
| | | | 2 | 3.05 | 100.0 |
| C302 | SAIB/BB/EtOH/VE/SRL (47.5/43.6/4.9/1/3) | NA | T0 | 3.08 | 100.0 |
| | | 5 | 2 | 3.08 | 100.0 |
| | | 25 | 2 | — | — |
| | | 40 | 1 | 3.09 | 100.3 |
| | | | 2 | 3.06 | 99.4 |
| C304 | SAIB/BB/EtOH/ATBC/VE/SRL (1/43.6/4.9/46.5/1/3) | NA | T0 | 3.1 | 100.0 |
| | | 5 | 2 | 3.08 | 99.4 |
| | | 25 | 2 | — | — |
| | | 40 | 1 | 3.10 | 100.0 |
| | | | 2 | 3.04 | 98.1 |
| C305 | BB/EtOH/ATBC/VE/SRL (43.6/4.9/47.7/1/3) | NA | T0 | 3.1 | 100.0 |
| | | 5 | 2 | 3.1 | 100.0 |
| | | 25 | 2 | 3.07 | 99.0 |
| | | 40 | 1 | 3.02 | 97.4 |
| | | | 2 | 3.01 | 97.1 |
| C306 | SAIB/BB/EtOH/VATBC/E/SRL (9.7/38.8/4.9/44.7/1/3) | NA | T0 | 3.08 | 100.0 |
| | | 5 | 2 | 3.07 | 99.7 |
| | | 25 | 2 | 3.05 | 99.0 |
| | | 40 | 1 | 3.03 | 98.4 |
| | | | 2 | 3.01 | 97.7 |
| C307 | SAIB/BB/EtOH/ATBC/VE/PLXM/SRL (1/42.7/4.9/46.5/1/1/3) | NA | T0 | 3.08 | 100.0 |
| | | 5 | 2 | 3.1 | 100.7 |
| | | 25 | 2 | 3.08 | 100.0 |
| | | 40 | 1 | 3.05 | 99.0 |
| | | | 2 | 3.03 | 98.4 |
| C308 | SAIB/BB/EtOH/ATBC/SRL (1/43.6/4.9/47.9/3) | NA | T0 | 3.08 | 100.0 |
| | | 5 | 2 | 3.07 | 99.7 |
| | | 25 | 2 | 2.85 | 92.5 |
| | | 40 | 1 | 2.81 | 91.2 |
| | | | 2 | 2.78 | 90.3 |
| C309 | SAIB/BB/EtOH/ATBC/VE/SRL (1/38.8/4.9/42.7/9.7/3) | NA | T0 | 3.06 | 100.0 |
| | | 5 | 2 | 3.1 | 101.3 |
| | | 25 | 2 | 3.05 | 99.7 |
| | | 40 | 1 | 3.03 | 99.0 |
| | | | 2 | 3.01 | 98.4 |

Figure 3:
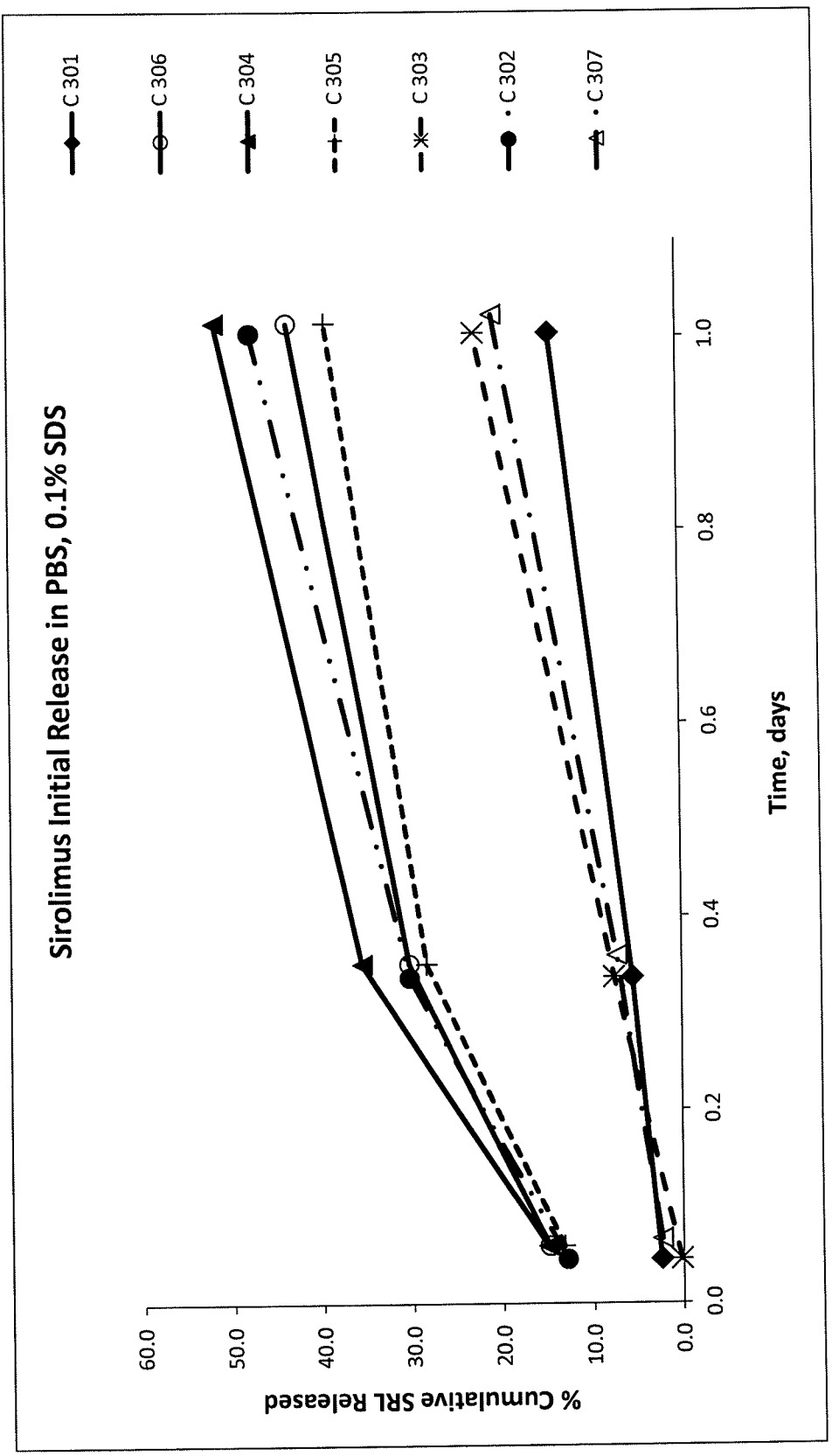
FIG. 3 shows cumulative release profile of sirolimus formulations in PBS medium containing 0.1% SDS.

A summary of chemical stabilities of sirolimus formulations after 2 weeks storage at 40° C., as well as the % cumulative sirolimus released after 24 hrs in PBS containing 0.1% SDS at 37° C., is listed in Tables 14 and FIG. 3.

TABLE 14a

| Pharmaceutical Composition Formulation | Composition of Formulations, (Parts by Weight) | % Recovery 2 weeks at 40° C. | % Cumulative Sirolimus Released after 24 hrs |
|---|---|---|---|
| C301 | SAIB/BB/EtOH/PLXM/VE/SRL (46.5/43.6/4.9/1/1/3) | 90.9 | 15.2 |
| C303 | SAIB/BB/EtOH/PEG 400/VE/SRL (9.7/38.8/4.9/42.7/1/3) | 100.0 | 22.5* |
| C302 | SAIB/BB/EtOH/VE/SRL (47.5/43.6/4.9/1/3) | 99.4 | 47.7 |
| C304 | SAIB/BB/EtOH/ATBC/VE/SRL (1/43.6/4.9/46.5/1/3) | 98.1 | 51.6 |

*Value may be underestimated due to possible precipitation in depot

TABLE 14b

| | Further Evaluation around ATBC Formulation C304 | | % Sirolimus Recovery 40° C., 2 wks | % Cumulative Sirolimus Released after 24 hrs |
|---|---|---|---|---|
| Effect of SAIB (0, 1%, 10%) | C305 (0% SAIB) | BB/EtOH/ATBC/VE/SRL (43.6/4.9/47.7/1/3) | 97.1 | 39.3 |
| | C304 (1% SAIB) | SAIB/BB/EtOH/ATBC/VE/SRL (1/43.6/4.9/46.5/1/3) | 98.1 | 51.6 |
| | C306 (10% SAIB) | SAIB/BB/EtOH/ATBC/VE/SRL (9.7/38.8/4.9/44.7/1/3) | 97.7 | 43.6 |
| Effect of PLXM (1%) | C304 (0% PLXM) | SAIB/BB/EtOH/ATBC/VE/SRL (1/43.6/4.9/46.5/1/3) | 98.1 | 51.6 |
| | C307 (1% PLXM) | SAIB/BB/EtOH/ATBC/VE/PLXM/SRL (1/42.7/4.9/46.5/1/1/3) | 98.4 | 20.4 |
| Effect of Vitamin E (0, 1%, 10%) | C308 (0% Vitamin E) | SAIB/BB/EtOH/ATBC/SRL (1/43.6/4.9/47.9/3) | 90.3 | NT |
| | V304 (1% Vitamin E) | SAIB/BB/EtOH/ATBC/VE/SRL (1/43.6/4.9/46.5/1/3) | 98.1 | 51.6 |
| | C309 (10% Vitamin E) | SAIB/BB/EtOH/ATBC/VE/SRL (1/38.8/4.9/42.7/9.7/3) | 98.4 | NT |

VE: Vitamin E

NT: Not Tested

As the amount of HVLCM increased, the viscosity of the composition generally increased. For example, as the amount of SAIB increased from 1% to 49%, the viscosity of the composition increased from 11 to 46 cP. The amount of HVLCM, e.g., SAIB, seemed to have no effect on chemical stability of sirolimus. The amount of HVLCM, e.g., SAIB, seemed to have only a slight effect on the initial rate of drug (e.g., sirolimus) release. In the presence of ATBC, SAIB (1-10 wt %) appeared to have little to no effect on chemical stability Polymer, e.g., poloxamer, appeared to lower the rate of initial in vitro release of drug, e.g., sirolimus. Polymer, e.g., poloxamer at 1 wt %, did not appear to affect viscosity of the composition. In formulations containing ATBC, 1% vitamin E in the presence of 1% poloxamer appeared to have little or no effect on enhancing chemical stability.

Among the chemical stability enhancers evaluated, tocopherol (e.g., vitamin E) appeared to be the most effective enhancer of chemical stability for sirolimus. Tocopherol appeared to enhance the stability of sirolimus in the presence of ATBC, with or without poloxamer. Increasing vitamin E from 1 wt % to 10 wt % did not appear to significantly further enhance chemical stability.

Example 4: In Vivo PK Study

Pharmaceutical compositions having the components and amounts shown in Table 15 were prepared.

Male Japanese White rabbits were systemically anesthetized and thereafter, both eyes were anesthetized on the surface by administering eye drops of oxybuprocaine hydrochloride (0.5%). The rabbits received a single bilateral intravitreal injection of 20 or 30 microliters of formulation. The rabbits were euthanized 1 month, 2 months, 3 months, and 6 months after administration. The enucleated eyes were dissected while frozen and the vitreous humor and retina-choroid were isolated. Amount of sirolimus was determined using liquid chromatography combined with tandem mass spectrometry.

TABLE 15

Test Articles for the First Rabbit PK Study

| Formulation (API wt %) | Vehicle Components | Composition of Formulations (Parts by Weight) | Dose | Evaluation Period (Sampling Timing) |
|---|---|---|---|---|
| C401 (3%) | SAIB/BB/EtOH (50/45/5) | 3 wt % sirolimus<br>48.5 wt % SAIB<br>43.7 wt % BB<br>4.8 wt % EtOH | 0.6 mg (20 μL/eye) | Blood:<br>2, 24 hrs<br>3, 7, 14 days<br>1, 2, 3, 4, 5, 6, |
| C402 (3%) | SAIB/BB/EtOH/PLXM (45/49/5/1) | 3 wt % sirolimus<br>43.7 wt % SAIB<br>47.5 wt % BB<br>4.8 wt % EtOH<br>1 wt % PLXM | 0.6 mg (20 μL/eye) | Months (M)<br>Vitreous/RC<br>(retina choroid)<br>1, 3, 6 M |
| C403 (3%) | SAIB/BB/PEG400/EtOH/PLXM (30/49/15/5/1) | 3 wt % sirolimus<br>29.1 wt % SAIB<br>47.5 wt % BB<br>14.6 wt % PEG400<br>4.8 wt % EtOH<br>1 wt % PLXM | 0.6 mg (20 μL/eye) | |
| C404 (3%) | SAIB/BB/PEG400/EtOH (30/50/15/5) | 3 wt % sirolimus<br>29.1 wt % SAIB<br>48.5 wt % BB<br>14.6 wt % PEG400<br>4.8 wt % EtOH | 0.6 mg (20 μL/eye) | |
| C405 (3%) | SAIB/BB/EtOH (15/80/5) | 3 wt % sirolimus<br>14.6 wt % SAIB<br>77.6 wt % BB<br>4.8 wt % EtOH | 0.6 mg (20 μL/eye) | Blood:<br>same timing as<br>above<br>Vitreous/RC:<br>only 3 M |
| C406 (3%) | SAIB/BB/EtOH (1/94/5) | 3 wt % sirolimus<br>1 wt % SAIB<br>91.2 wt % BB<br>4.8 wt % EtOH | 0.6 mg (20 μL/eye) | |
| C407 (3%) | SAIB/BB/EtOH (50/45/5) | 3 wt % sirolimus<br>48.5 wt % SAIB<br>43.7 wt % BB<br>4.8 wt % EtOH | 0.9 mg (30 μL/eye) | Vitreous/RC:<br>only 3 M |
| C407 (3%) | SAIB/BB/EtOH (50/45/5) | 3 wt % sirolimus<br>48.5 wt % SAIB<br>43.7 wt % BB<br>4.8 wt % EtOH | 0.9 mg (30 μL/eye) | Vitreous/RC<br>(retina choroid)<br>1, 3, 6 M |

The remaining ratios of sirolimus in the vitreous humors are shown in Table 16 (based on 4-6 eyes). The concentrations of sirolimus in the retina-choroid are shown in Table 17 (based on 3-6 eyes). Remaining amounts are provided as mean±SD.

TABLE 16

| Pharmaceutical Composition Formulation | Concentration of Sirolimus (% W/W) | Dose | Remaining ratio of Sirolimus (%) | | |
|---|---|---|---|---|---|
| | | | 1 Month | 3 Months | 6 Months |
| C401 | 3 | 0.6 mg/20 μL/eye | 70.3 ± 6.8 | 13.2 ± 2.9 | 2.8 ± 1.3 |
| C404 | 3 | 0.6 mg/20 μL/eye | 47.1 ± 11.1 | 7.7 ± 3.0 | 0.8 ± 0.3 |
| C403 | 3 | 0.6 mg/20 μL/eye | 94.4 ± 1.2 | 59.2 ± 3.9 | 25.3 ± 13.3 |
| C402 | 3 | 0.6 mg/20 μL/eye | 105.5 ± 5.0 | 60.7 ± 6.3 | 23.2 ± 1.0 |
| C406 | 3 | 0.6 mg/20 μL/eye | — | 14.4 ± 8.1 | — |
| C405 | 3 | 0.6 mg/20 μL/eye | — | 2.2 ± 1.8 | — |
| C407 | 3 | 0.9 mg/30 μL/eye | — | 10.3 ± 5.4 | — |
| C407 | 3 | 0.9 mg/30 μL/eye | 91.8 ± 3.6 | 73.3 ± 9.9 | 30.0 ± 11.1 |

TABLE 17

| Pharmaceutical Composition Formulation | Concentration of Sirolimus (% W/W) | Dose | Concentration of Sirolimus in Retina-Choroid (ng/g) | | |
|---|---|---|---|---|---|
| | | | 1 Month | 3 Months | 6 Months |
| C401 | 3 | 0.6 mg/20 μL/eye | 248 ± 92.3 | 156 ± 50.1 | 551 ± 218 |
| C404 | 3 | 0.6 mg/20 μL/eye | 414 ± 243 | 126 ± 93.9 | 164 ± 69.9 |
| C403 | 3 | 0.6 mg/20 μL/eye | 281 ± 147 | 320 ± 255 | 3421 ± 1980 |
| C402 | 3 | 0.6 mg/20 μL/eye | 385 ± 157 | 269 ± 41.4 | 4846 ± 1957 |
| C406 | 3 | 0.6 mg/20 μL/eye | — | 262 ± 269 | — |
| C405 | 3 | 0.6 mg/20 μL/eye | — | 65.5 ± 103 | — |
| C407 | 3 | 0.9 mg/30 μL/eye | — | 107 ± 118 | — |
| C407 | 3 | 0.9 mg/30 μL/eye | 896 ± 484 | 445 ± 113 | 413 ± 92.4 |

Figure 4:
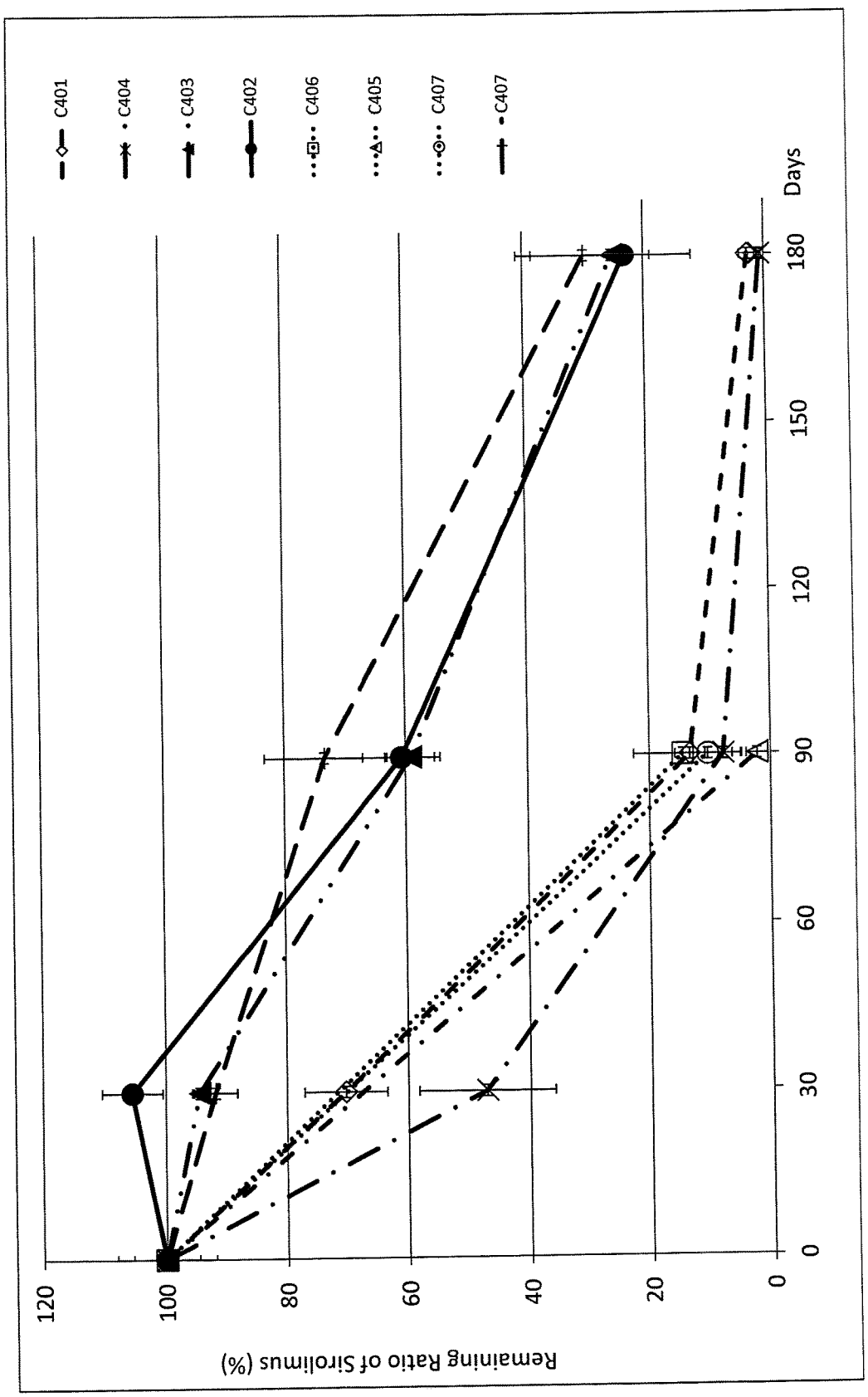
FIG. 4 shows sirolimus remaining in vitreous humor over 6 months obtained from intravitreal depots from compositions of the present disclosure.
Figure 5:
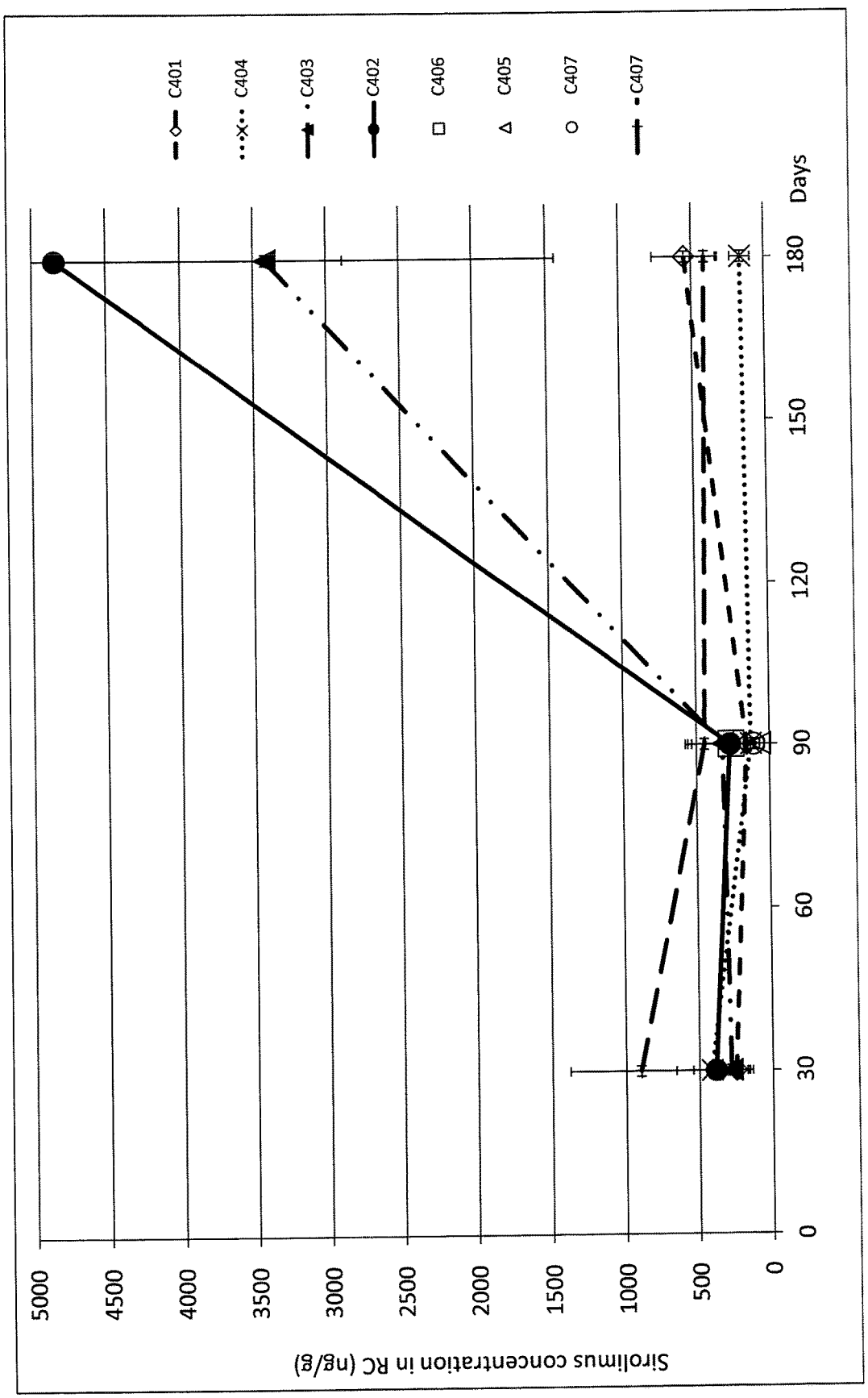
FIG. 5 shows sirolimus in rabbit retinoid choroid (RC) (6-month data).

FIGS. 4 and 5 show data over a 6-month period for the amount of sirolimus remaining in the depots, and the sirolimus concentration in the vitreous humors.

The formulations referred to as C401 and C407 were made with the same components and ratios thereof, on separate occasions. As shown in Tables 16 and 17, and FIGS. 4 and 5, there was variability in the sirolimus release profiles of formulations C401 and C407 having a vehicle consisting of SAIB, BB and EtOH.

Example 5: In Vivo PK Study

Pharmaceutical compositions having the components and amounts shown in Table 18 were prepared.

Male Japanese White rabbits were systemically anesthetized and thereafter, both eyes were anesthetized on the surface by administering eye drops of oxybuprocaine hydrochloride (0.5%). The rabbits received a single bilateral intravitreal injection of 20 or 30 microliters of formulation. The rabbits were euthanized 1 month, 2 months, 3 months and 6 months after administration. The enucleated eyes were dissected while frozen and the vitreous humor and retina-choroid were isolated. Amount of sirolimus was determined using liquid chromatography combined with tandem mass spectrometry.

TABLE 18

| Formulation (API wt %) | Vehicle Component | Composition of Formulations (Parts by Weight) | Dose | Objective | Evaluation Period (sampling timing) |
|---|---|---|---|---|---|
| C501 (3 wt %) | SAIB/BB/EtOH/ATEC/PLXM/VE (1/45/5/47/1/1) | 3 wt % sirolimus<br>1 wt % SAIB<br>43.6 wt % BB<br>4.8 wt % EtOH<br>45.6 wt % ATEC<br>1 wt % PLXM<br>1 wt % VE | 0.9 mg/eye<br>30 μL | evaluate the effect of poloxamer (PLXM) and vitamin E (VE) | Blood:<br>2, 24 hrs<br>3, 7, 14 days<br>1, 2, 3, 6 M<br>Vitreous/RC:<br>1, 3, 6 M |
| C502 (3 wt %) | SAIB/BB/EtOH/ATEC/PLXM (40/40/5/14/1) | 3 wt % sirolimus<br>38.8 wt % SAIB<br>38.8 wt % BB<br>4.8 wt % EtOH<br>13.6 wt % ATEC<br>1 wt % PLXM | 0.9 mg/eye<br>30 μL | evaluate the effect of PLXM | |
| C503 (4.5 wt %) | SAIB/BB/EtOH/ATEC/PLXM (1/45/5/48/1) | 4.5 wt % sirolimus<br>1 wt % SAIB<br>43 wt % BB<br>4.7 wt % EtOH<br>45.8 wt % ATEC<br>1 wt % PLXM | 1.35 mg/eye<br>30 μL | evaluate the effect of PLXM and low SAIB | |
| C504 (4.5 wt %) | SAIB/BB/EtOH/ATEC/VE (1/45/5/48/1) | 4.5 wt % sirolimus<br>1 wt % SAIB<br>43 wt % BB<br>4.7 wt % EtOH<br>45.8 wt % ATEC<br>1 wt % VE | 1.35 mg/eye<br>30 μL | evaluate the effect of VE and low SAIB | |
| C505 (3 wt %) | SAIB/BB/EtOH/PLXM (45/49/5/1) | 3 wt % sirolimus<br>43.7 wt % SAIB<br>47.5 wt % BB<br>4.8 wt % EtOH<br>1 wt % PLXM | 0.9 mg/eye<br>30 μL | control | |
| C506 (2 wt %) | PEG400/EtOH (95/5) | 2 wt % sirolimus<br>93.1 wt % PEG<br>4.9 wt % EtOH | 0.44 mg/eye<br>20 μL | control | Blood:<br>2, 24 hrs<br>3, 7, 14 days<br>1, 2 M<br>Vitreous/RC:<br>1, 2 M |

Table 19 shows the remaining ratio of sirolimus in the intra-vitreous depots. Table 20 shows the concentration of sirolimus in retina/choroid. Amounts are expressed as mean±SD (based on 2-4 eyes).

TABLE 19

| Pharmaceutical Composition Formulation | Concentration of Sirolimus (% W/W) | Dose | Remaining Ratio of Sirolimus (%) | | | |
|---|---|---|---|---|---|---|
| | | | 1 Month | 2 Months | 3 Months | 6 Months |
| C505 | 3 | 0.9 mg/30 μL/eye | 82.4 ± 1.4 | — | 72.7 ± 4.3 | 33.8 |
| C501 | 3 | 0.9 mg/30 μL/eye | 83.3 ± 2.8 | — | 61.4 ± 4.1 | 55.3 |
| C502 | 3 | 0.9 mg/30 μL/eye | 65.3 ± 34.9 | — | 58.1 ± 2.7 | 31.3 ± 3.6 |
| C503 | 4.5 | 1.35 mg/30 μL/eye | 64.6 ± 6.0 | — | 58.8 ± 18.3 | 23.0 ± 11.3 |
| C504 | 4.5 | 1.35 mg/30 μL/eye | 61.9 ± 6.8 | — | 63.8 ± 2.6 | 56.2 ± 15.2 |
| C506 | 2 | 0.44 mg/20 μL/eye | 18.5 ± 13.2 | 9.3 ± 6.0 | — | — |

TABLE 20

| Pharmaceutical Composition Formulation | Concentration of Sirolimus (% W/W) | Dose | Concentration of Sirolimus (ng/g) | | | |
|---|---|---|---|---|---|---|
| | | | 1 Month | 2 Months | 3 Months | 6 Months |
| C505 | 3 | 0.9 mg/30 μL/eye | 406 ± 338 | — | 549 ± 381 | 201 |
| C501 | 3 | 0.9 mg/30 μL/eye | 406 ± 386 | — | 536 ± 460 | 284 |
| C502 | 3 | 0.9 mg/30 μL/eye | 302 ± 183 | — | 507 ± 238 | 609 ± 733 |
| C503 | 4.5 | 1.35 mg/30 μL/eye | 1839 ± 531 | — | 617 ± 415 | 126 ± 102 |
| C504 | 4.5 | 1.35 mg/30 μL/eye | 754 ± 662 | — | 341 ± 109 | 1060 ± 928 |
| C506 | 2 | 0.44 mg/20 μL/eye | 719 ± 359 | 644 ± 505 | — | — |

Figure 6:
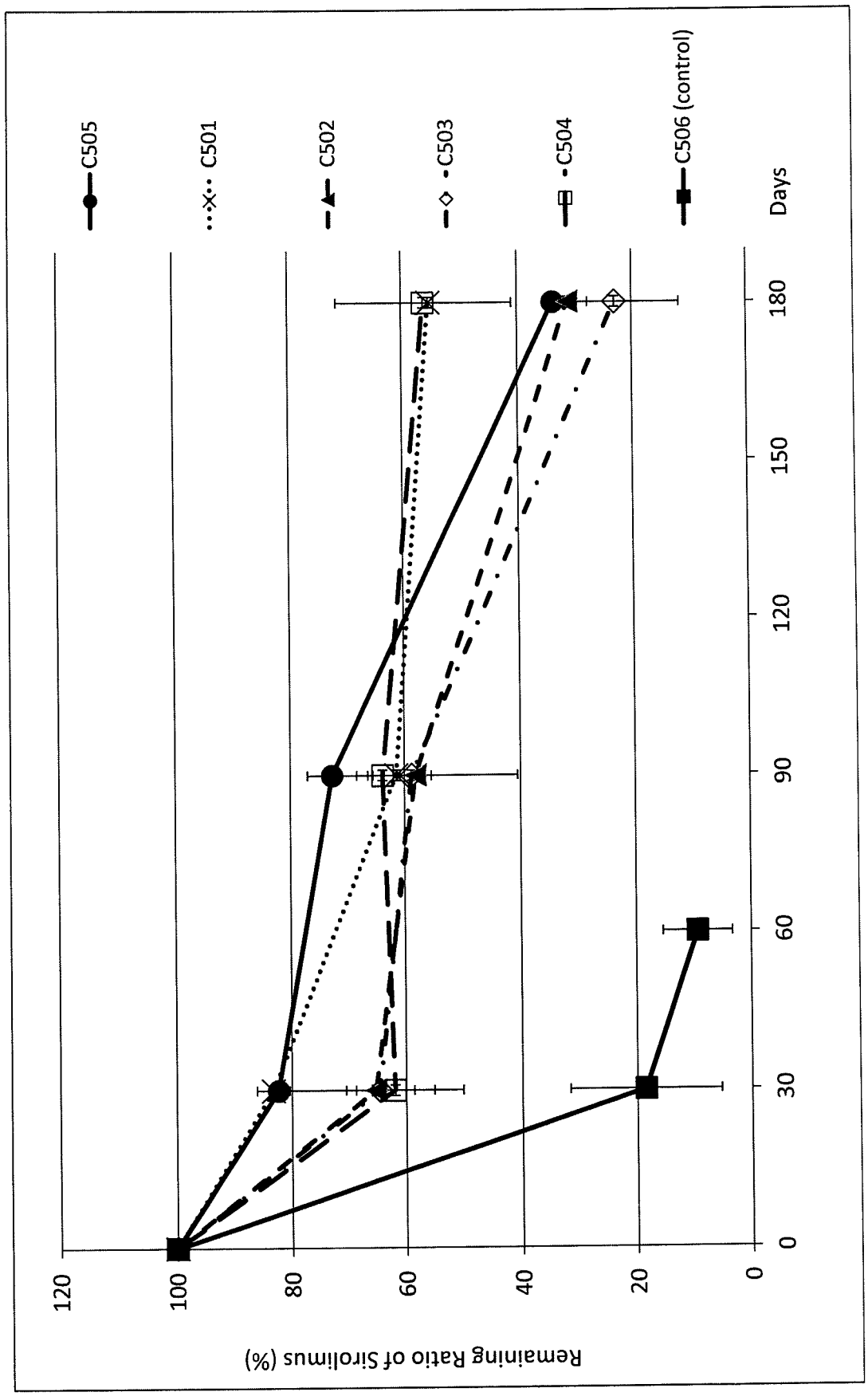
FIG. 6 shows sirolimus remaining in vitreous humor as described in more detail below in Example 5.
Figure 7:
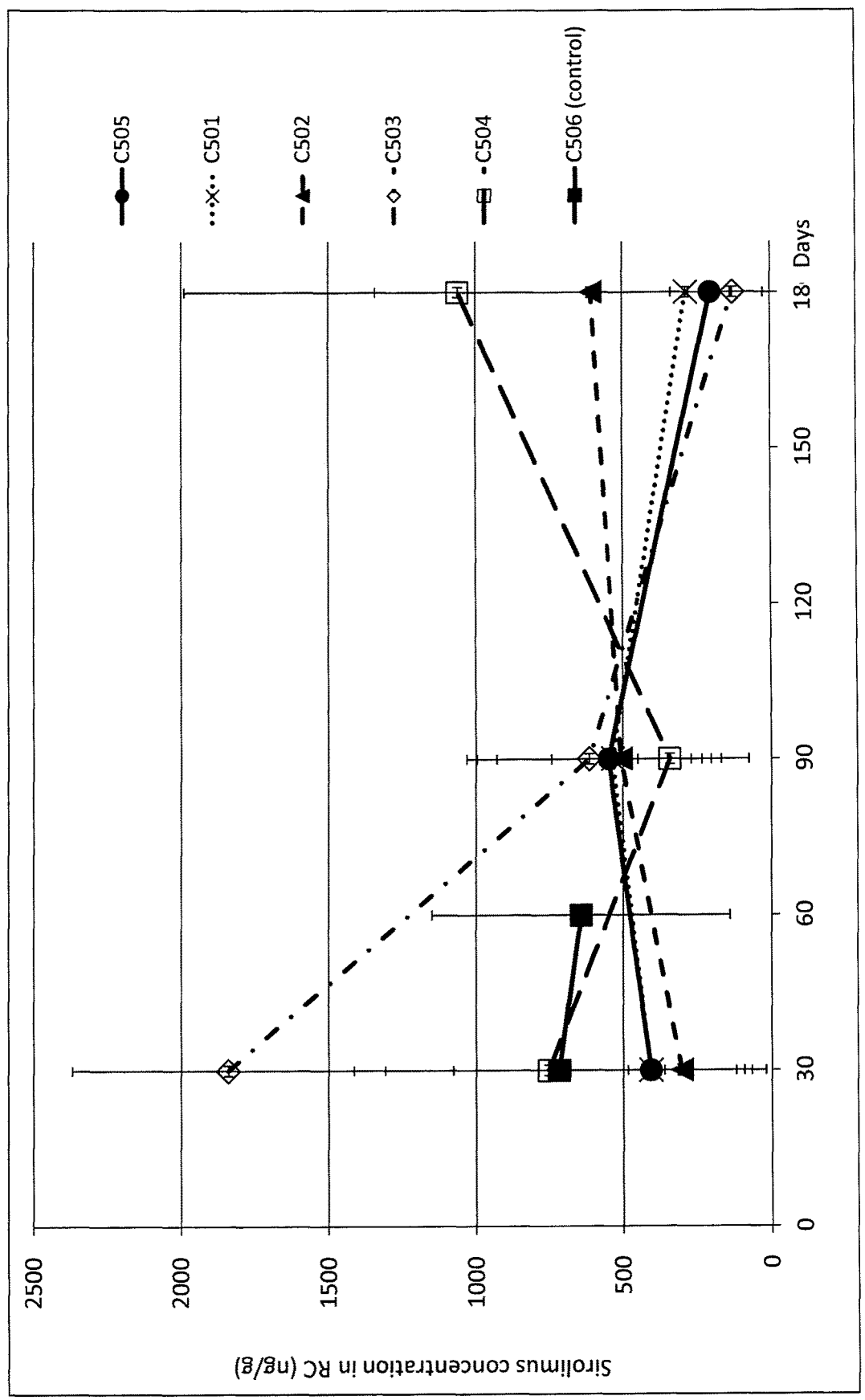
FIG. 7 shows sirolimus concentration in RC over time as described in more detail below in Example 5.

FIGS. 6 and 7 show data over a 6-month period for the amount of sirolimus remaining in the depots, and the sirolimus concentration in the vitreous humors.

Figure 8:
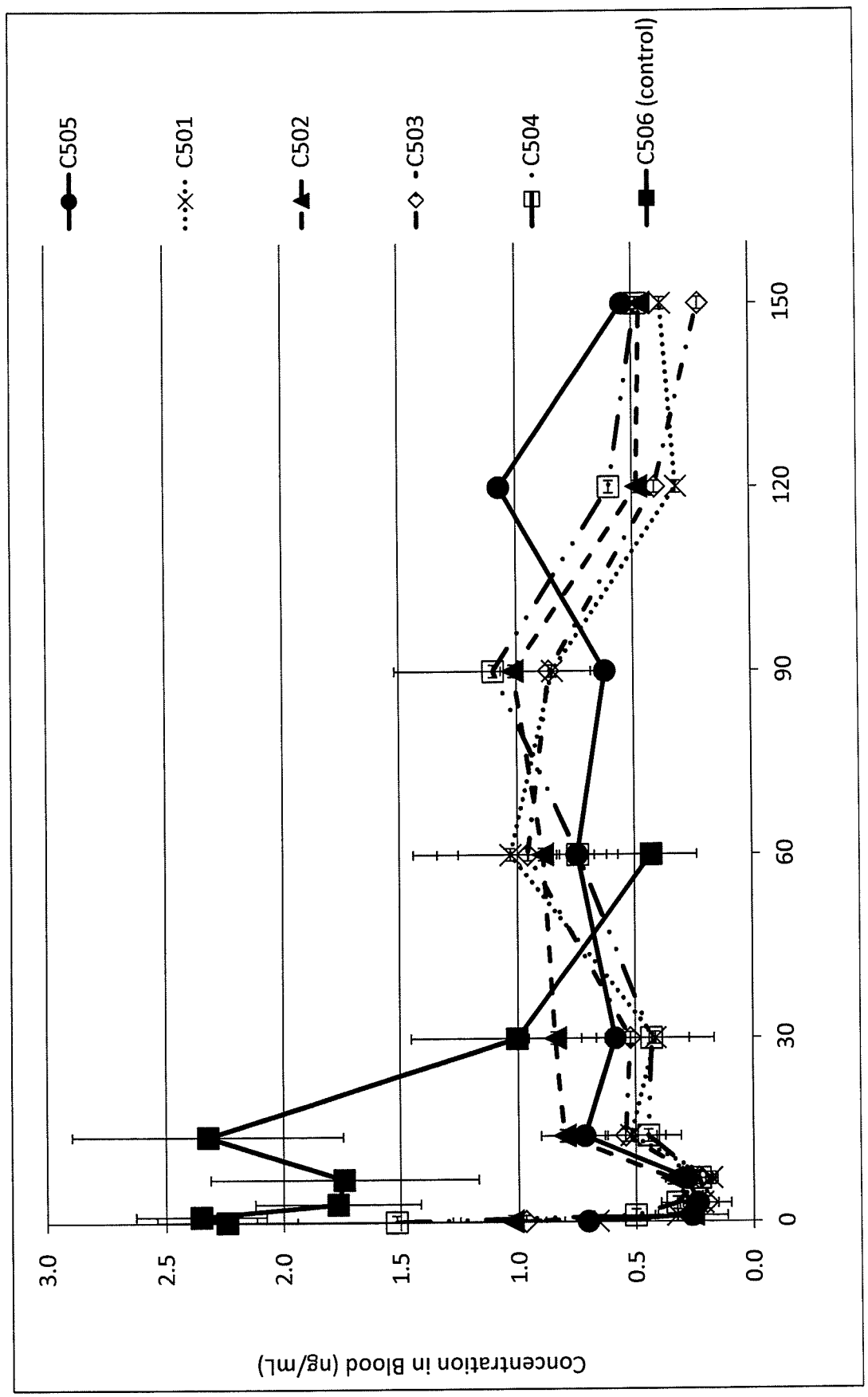
FIG. 8 shows sirolimus blood concentration after placement of intra vitreal depots as described in more detail below in Example 5.

Blood levels of sirolimus were measured at 30-day intervals. The results are shown in FIG. 8.

Example 6: In Vivo PK Study

Solvents used are as follows: SAIB and acetyl tributyl citrate (such as commercially available from Sigma-Aldrich), benzyl benzoate and ethanol (99.5) (such as commercially available from Nacalai Tesque, Inc.), vitamin E (such as commercially available from Riken Vitamin).

Sirolimus is commercially available from a number of sources, including Santen Pharmaceutical Company.

Preparation of Sirolimus Solution Formulations:

In a standard bottle, 240 mg of sirolimus were measured, and dissolved by adding 4.4 mL of pre-mixed SD/BB/EtOH (10/40/5, v/v/v), 3.6 mL of premixed BB/EtOH (40/5, v/v), or 3.68 mL of pre-mixed VitE/BB/EtOH (1/40/5, v/v/v). Then 3.6 mL, 4.4 mL, or 4.32 mL of acetyl tributyl citrate was added and mixed, respectively, thereby preparing the formulation of SD/BB/EtOH/ATBC (10/40/5/45, v/v/v/v), BB/EtOH/ATBC (40/5/55, v/v/v), or VitE/BB/EtOH/ATBC (1/40/5/54, v/v/v/v). A control composition comprising EtOH/PEG400/SRL (4/92/4, w/w/w) was also prepared. Compositions and doses are shown in Table 21.

TABLE 21

| Pharmaceutical Composition Formulation | Composition of Vehicles (Parts by Weight) | Concentration of each component based on weight of the composition (wt %) | Dose |
|---|---|---|---|
| C601 | EtOH/PEG400 (4/92) | 4 wt % sirolimus<br>4 wt % EtOH<br>92 wt % PEG400 | 0.88 mg/20 μL/eye |
| C602 | SD*/BB/EtOH/ATBC (10/40/5/45) | 2.7 wt % sirolimus<br>10.4 wt % SAIB*<br>40.6 wt % BB<br>3.6 wt % EtOH<br>42.8 wt % ATBC | 0.9 mg/30 μL/eye |
| C603 | BB/EtOH/ATBC (40/5/55) | 2.7 wt % sirolimus<br>40.9 wt % BB<br>3.6 wt % EtOH<br>52.8 wt % ATBC | 0.9 mg/30 μL/eye |
| C604 | VitE/BB/EtOH/ATBC (1/40/5/54) | 2.7 wt % sirolimus<br>40.9 wt % BB<br>3.6 wt % EtOH<br>51.9 wt % ATBC<br>0.9 wt % Vitamin E | 0.9 mg/30 μL/eye |

*SD: SAIB reagent grade

Rabbit PK Study Following Intravitreal Injection of Sirolimus Solution Formulations:

Male Japanese white rabbits were systemically anesthetized and thereafter, both eyes were anesthetized on the surface by administering eye drops of oxybuprocaine hydrochloride (0.5%). The rabbits received a single bilateral intravitreal injection of 30 microliters of test formulation or 20 microliters of 4% sirolimus in PEG400/EtOH (94/2). The rabbits were euthanized 4 weeks and 12 weeks after administration. The enucleated eyes were dissected while frozen and the vitreous humor was isolated. Amount of sirolimus in vitreous body was determined using liquid chromatography combined with tandem mass spectrometry.

Table 22 shows the remaining amounts of dose in the intra-vitreous depots.

TABLE 22

| Pharmaceutical Composition Formulation | Dose | Remaining (% of dose amount) | |
|---|---|---|---|
| | | 4 weeks | 12 weeks |
| C601 | 0.88 mg/20 μL/eye | 40.3 ± 19.9 | BLQ |
| C602 | 0.9 mg/30 μL/eye | 59.4 ± 8.4 | 25.5 ± 12.3 |
| C603 | 0.9 mg/30 μL/eye | 71.1 ± 14.4 | 29.4 ± 3.8 |
| C604 | 0.9 mg/30 μL/eye | 83.7 ± 7.7 | 73.8 ± 4.3 |

Mean ± SD (3-4 eyes)
BLQ: Below the lower limit of quantification

FIG. 9 shows data over a 12-week period for the amount of sirolimus remaining in the depots. Because the depot cannot be separately removed from the vitreous humor, the amount of sirolimus remaining in the depots is assumed in the present disclosure to be equivalent to the amount of sirolimus in the combined vitreous humor and depot.

Example 7: Pharmaceutical Compositions

Compositions are prepared as in Tables 23a and 23b. Amounts of excipients are expressed as parts by weight. The pharmaceutical compositions contain sirolimus in a concentration of 3 mg/ml.

TABLE 23a

| | C701 | C702 | C703 | C704 | C705 | C706 | C707 | C708 | C709 |
|---|---|---|---|---|---|---|---|---|---|
| SRL | 3 | 3 | 3 | 3 | 3 | 3 | 3 | 3 | 3 |
| SAIB | 1 | 0 | 1 | 48 | 45 | 1 | 10 | 1 | 48 |
| BB | 45 | 45 | 45 | 45 | 49 | 45 | 40 | 45 | 45 |
| EtOH | 5 | 5 | 5 | 5 | 5 | 5 | 5 | 5 | 5 |
| PLXM | 1 | 1 | — | 1 | 1 | 1 | — | — | 1 |
| PEG400 | — | — | — | — | — | — | 44 | 48 | — |
| VE | 1 | 1 | 1 | 1 | 1 | 1 | 1 | 1 | 1 |
| ATEC | 47 | 48 | 48 | — | — | — | — | — | — |
| TEC | — | — | — | — | — | 47 | — | — | — |

TABLE 23b

| | C710 | C711 | C712 | C713 | C714 | C715 |
|---|---|---|---|---|---|---|
| SRL | 3 | 3 | 3 | 3 | 3 | 3 |
| SAIB | 1 | 10 | 10 | 1 | 49 | 1 |
| BB | 45 | 40 | 40 | 44.5 | 45 | 45 |
| EtOH | 5 | 5 | 5 | 5 | 5 | 5 |
| PLXM | 1 | 1 | 1 | 0.5 | | |
| VE | 1 | 1 | 1 | 1 | 1 | 1 |
| ATBC | | | | | | 48 |
| TEC | 47 | | | | | |
| Lauroglycol 90 | — | 43 | | | | |
| Ceraphyl 30 | — | | 43 | | | |
| Labrafac PG | | | | 48 | | |

Example 8

Sustained Releasability Evaluation Test:

The drug sustained releasability in an animal of the depot formulation of the present disclosure was evaluated.

Preparation of Test Articles:

In standard bottles, 240 mg of sirolimus was weighed, and after being dissolved by adding 0.8 mL of dimethyl sulfoxide, 7.2 mL of acetyl triethyl citrate and mixing, followed by performing filtration sterilization with a filter of 0.20 μm pore size, thereby preparing the formulations of comparative composition C801.

In standard bottles, 240 mg of sirolimus was weighed, and after being dissolved by adding 3.6 mL of benzyl benzoate/ethanol (40:5 by volume ratio) or 3.68 mL of vitamin E/benzyl benzoate/ethanol (1:40:5 by volume ratio) that were mixed in advance, 4.4 mL or 4.32 mL of acetyl tri-n-butyl citrate was added and mixed, followed by performing filtration sterilization with a filter of 0.20 μm pore size, thereby preparing the formulations C802 and C803.

Rabbit Pharmacokinetics Evaluation:

Using a Hamilton syringe equipped with a 30 G needle, 0.03 mL of the depot formulations of C801 (comparative), C802, and C803 per eye of albino rabbit was intravitreally administered. After four weeks and after twelve weeks from administration, euthanization was conducted with anesthetic by intravenous administration of pentobarbital sodium, and the eyeballs were enucleated. The enucleated eyeballs were immediately frozen, and the vitreous bodies collected in a state containing the depot formulation. The sirolimus concentration in the vitreous body at each time point of collection was measured using a LC-MS/MS, and the drug residual amount after administration was evaluated.

Test Results and Considerations:

The test results are shown in Table 24.

TABLE 24

| Formula | | C801 | C802 | C803 |
|---|---|---|---|---|
| sirolimus | | 240 mg | 240 mg | 240 mg |
| Acetyl tri-n-butyl citrate | | — | 4.4 mL | 4.32 mL |
| Acetyl triethyl citrate | | 7.2 mL | — | — |
| Benzyl benzoate | | — | 3.2 mL | 3.2 mL |
| Dimethylsulfoxide | | 0.8 mL | — | — |
| Ethanol | | — | 0.4 mL | 0.4 mL |
| Vitamin E | | — | — | 0.08 mL |
| Residual rate of sirolimus (%) | After 4 weeks | 10.0 | 71.1 | 83.7 |
| | After 12 weeks | 0.2 | 29.4 | 73.8 |

As shown in Table 24, only 10.0% of the administered amount of sirolimus remained at four weeks after administration for comparative formulation C801; whereas, 71.1% of the administered amount for formulation C802 remained, and 83.7% of the administered amount for formulation C803 remained.

According to the above results, it was confirmed that the sustained-releasability is improved by the present depot formulation.

Example 9: Pharmaceutical Compositions and In Vivo PK Study

Compositions were prepared as in Table 25. Amounts of excipients are expressed as parts by weight. The pharmaceutical compositions contained sirolimus in a concentration of 30 mg/g.

TABLE 25

| | C901 | C902 | C903 | C904 | C905 |
|---|---|---|---|---|---|
| SRL | 3 | 3 | 3 | 3 | 3 |
| SAIB | 1 | 0 | 1 | 46.5 | 43.7 |
| BB | 43.6 | 43.7 | 43.7 | 43.7 | 47.5 |
| EtOH | 4.8 | 4.8 | 4.8 | 4.8 | 4.8 |
| PLXM | 1 | 1 | — | 1 | 1 |
| VE | 1 | 1 | 1 | 1 | — |
| ATEC | 45.6 | 46.5 | 46.5 | — | — |

Rabbit PK Study Following Intravitreal Injection of Sirolimus Solution Formulations:

Male Japanese white rabbits were systemically anesthetized and thereafter, both eyes were anesthetized on the surface by administering eye drops of oxybuprocaine hydrochloride (0.5%). The rabbits received a single bilateral intravitreal injection of 30 microliters of test formulation. The rabbits were euthanized 4 weeks and 12 weeks after administration. The enucleated eyes were dissected while frozen and the vitreous humor was isolated. Amount of sirolimus in vitreous body was determined using liquid chromatography combined with tandem mass spectrometry.

Table 26 shows the remaining amounts of dose in the intra-vitreous depots. FIG. 10 shows data over a 6-month period involving formulations C901 to C905 for the amount of sirolimus remaining in the depots. As noted above, the amount of sirolimus remaining in the depots is assumed in the present disclosure to be equivalent to the amount of sirolimus in the combined vitreous humor and depot.

TABLE 26

(remaining ratios of sirolimus in the vitreous humors)

| Pharmaceutical Composition Formulation | Concentration of sirolimus (% W/W) | Setting Dose (Setting value: administered amount of sirolimus) | Remaining ratio of sirolimus to initial administered sirolimus (%) | | |
|---|---|---|---|---|---|
| | | | 1 Month | 3 Months | 6 Months |
| C901 | 3 | 0.9 mg/30 µL/eye | 88.8 ± 6.4 | 65.8 ± 8.9 | 26.9 ± 5.9 |
| C902 | 3 | 0.9 mg/30 µL/eye | 88.2 ± 10.6 | 73.1 ± 7.5 | 21.2 ± 9.6 |
| C903 | 3 | 0.9 mg/30 µL/eye | 93.3 ± 5.6 | 79.3 | 54.8 ± 19.8 |
| C904 | 3 | 0.9 mg/30 µL/eye | 107.2 ± 3.9 | 92.0 ± 15.7 | 38.6 ± 2.1 |
| C905 | 3 | 0.9 mg/30 µL/eye | 114.4 ± 6.4 | 94.8 ± 9.1 | 34.2 ± 1.3 |

Table 27 and FIG. 11 show data over a 6-month period involving formulations C901 to C905 for the sirolimus concentration in the retina-choroid.

TABLE 27

(concentrations of sirolimus in the retina-choroid)

| Pharmaceutical Composition Formulation | Concentration of Sirolimus (% W/W) | Dose | Concentration of sirolimus (ng/g) | | |
|---|---|---|---|---|---|
| | | | 1 Month | 3 Months | 6 Months |
| C901 | 3 | 0.9 mg/30 µL/eye | 1033 ± 421 | 1721 ± 1360 | 273 ± 52.0 |
| C902 | 3 | 0.9 mg/30 µL/eye | 1418 ± 975 | 1424 ± 1612 | 486 ± 424 |
| C903 | 3 | 0.9 mg/30 µL/eye | 3339 ± 3016 | 804 | 772 ± 851 |
| C904 | 3 | 0.9 mg/30 µL/eye | 510 ± 185 | 1130 ± 414 | 456 ± 154 |
| C905 | 3 | 0.9 mg/30 µL/eye | 584 ± 381 | 1280 ± 930 | 513 ± 421 |

Blood levels of sirolimus were measured at 30-day intervals for formulations C901 to C905. The results are shown in FIG. 12.

Example 10: Pharmaceutical Compositions and In Vivo PK Study

Compositions were prepared as in Table 28. Amounts of excipients are expressed as parts by weight. The pharmaceutical compositions contained sirolimus in a concentration of 30 mg/g.

TABLE 28

| | C906 | C907 | C908 | C909 |
|---|---|---|---|---|
| SRL | 3 | 3 | 3 | 3 |
| SAIB | 1 | 9.7 | 1 | 46.5 |
| BB | 43.7 | 38.8 | 43.7 | 43.7 |

TABLE 28-continued

| | C906 | C907 | C908 | C909 |
|---|---|---|---|---|
| EtOH | 4.8 | 4.8 | 4.8 | 4.8 |
| PLXM | 1 | — | — | 1 |
| PEG400 | — | 42.7 | 46.5 | — |
| VE | 1 | 1 | 1 | 1 |
| TEC | 45.6 | — | — | — |

Rabbit PK Study Following Intravitreal Injection of Sirolimus Solution Formulations:

Male Japanese white rabbits were systemically anesthetized and thereafter, both eyes were anesthetized on the surface by administering eye drops of oxybuprocaine hydrochloride (0.5%). The rabbits received a single bilateral intravitreal injection of 30 microliters of test formulation. The rabbits were euthanized 4 weeks and 12 weeks after administration. The enucleated eyes were dissected while frozen and the vitreous humor was isolated. Amount of sirolimus in vitreous body was determined using liquid chromatography combined with tandem mass spectrometry.

Table 29 shows the remaining amounts of dose in the intra-vitreous depots. FIG. 13 shows data over a 6-month period involving formulations C906 to C909 for the amount of sirolimus remaining in the depots. As noted above, the amount of sirolimus remaining in the depots is assumed in the present disclosure to be equivalent to the amount of sirolimus in the combined vitreous humor and depot.

TABLE 29

(remaining ratios of sirolimus in the vitreous humors)

| Pharmaceutical Composition Formulation | Concentration of Sirolimus (% W/W) | Setting Dose (Setting value: administered amount of sirolimus) | Remaining Ratio of Sirolimus to Initial Administered Sirolimus (%) | | |
|---|---|---|---|---|---|
| | | | 1 Month | 3 Months | 6 Months |
| C906 | 3 | 0.9 mg/30 μL/eye | 82.8 ± 9.9 | 67.7 ± 12.0 | 30.0 ± 30.7 |
| C907 | 3 | 0.9 mg/30 μL/eye | 92.8 ± 5.5 | 74.1 ± 9.8 | 26.0 ± 7.0 |
| C908 | 3 | 0.9 mg/30 μL/eye | 94.4 ± 8.4 | 75.8 ± 21.9 | 25.9 ± 14.0 |
| C909 | 3 | 0.9 mg/30 μL/eye | 95.7 ± 1.6 | 82.2 ± 18.3 | 37.9 ± 2.8 |

Table 30 and FIG. 14 show data over a 6-month period involving formulations C906 to C909 for the sirolimus concentration in the retina-choroid.

TABLE 30

(concentrations of sirolimus in the retina-choroid)

| Pharmaceutical Composition Formulation | Concentration of Sirolimus (% W/W) | Dose | Concentration of Sirolimus (ng/g) | | |
|---|---|---|---|---|---|
| | | | 1 M | 3 M | 6 M |
| C906 | 3 | 0.9 mg/30 μL/eye | 1614 ± 1406 | 708 ± 1008 | 905 ± 616 |
| C907 | 3 | 0.9 mg/30 μL/eye | 905 ± 679 | 417 ± 237 | 442 ± 244 |
| C908 | 3 | 0.9 mg/30 μL/eye | 1080 ± 334 | 466 ± 227 | 261 ± 229 |
| C909 | 3 | 0.9 mg/30 μL/eye | 1381 ± 639 | 467 ± 331 | 444 ± 281 |

Blood levels of sirolimus were measured at 30-day intervals for formulations C906 to C909. The results are shown in FIG. 15.

Example 11: Pharmaceutical Compositions and In Vivo PK Study

Compositions were prepared as in Table 31. Amounts of excipients are expressed as parts by weight. The pharmaceutical compositions contained sirolimus in a concentration of 30 mg/g.

TABLE 31

| | C907 | C908 | C914 | C915 | C909 |
|---|---|---|---|---|---|
| SRL | 3 | 3 | 3 | 3 | 3 |
| SAIB | 9.7 | 1 | 47.5 | 1 | 46.5 |
| BB | 38.8 | 43.7 | 43.7 | 43.7 | 43.7 |
| EtOH | 4.8 | 4.8 | 4.8 | 4.8 | 4.8 |
| PLXM | — | — | — | — | 1 |
| PEG400 | 42.7 | 46.5 | — | — | — |
| VE | 1 | 1 | 1 | 1 | 1 |
| ATBC | — | — | — | 46.5 | — |

Rabbit PK Study following Intravitreal Injection of Sirolimus Solution Formulations:

Male Japanese white rabbits were systemically anesthetized and thereafter, both eyes were anesthetized on the surface by administering eye drops of oxybuprocaine hydrochloride (0.5%). The rabbits received a single bilateral intravitreal injection of 30 microliters of test formulation. The rabbits were euthanized 4 weeks and 12 weeks after administration. The enucleated eyes were dissected while frozen and the vitreous humor was isolated. Amount of sirolimus in vitreous body was determined using liquid chromatography combined with tandem mass spectrometry.

Table 32 and FIG. 16 show data over a 6-month period involving formulations C907 to C909, C914, and C915 for the amount of sirolimus remaining in the vitreous humor.

TABLE 32

(remaining ratios of sirolimus in the vitreous humors)

| Pharmaceutical Composition Formulation | Concentration of Sirolimus (% W/W) | Setting Dose (Setting value: administered amount of sirolimus) | Remaining Ratio of Sirolimus to Initial Administered Sirolimus (%) | | |
|---|---|---|---|---|---|
| | | | 1 Month | 3 Months | 6 Months |
| C907 | 3 | 0.9 mg/30 μL/eye | 82.8 ± 3.0 | 56.3 | 24.5 ± 7.6 |

TABLE 32-continued (remaining ratios of sirolimus in the vitreous humors)

| Pharmaceutical Composition | Concentration of Sirolimus | Setting Dose (Setting value: administered amount of | Remaining Ratio of Sirolimus to Initial Administered Sirolimus (%) | | |
|---|---|---|---|---|---|
| Formulation | (% W/W) | sirolimus) | 1 Month | 3 Months | 6 Months |
| C908 | 3 | 0.9 mg/30 μL/eye | 86.9 ± 1.8 | 63.4 ± 18.0 | 34.4 ± 5.3 |
| C914 | 3 | 0.9 mg/30 μL/eye | 91.4 ± 2.8 | 72.1 ± 4.9 | 31.6 ± 5.2 |
| C915 | 3 | 0.9 mg/30 μL/eye | 82.7 ± 14.3 | 73.7 ± 6.0 | 36.3 ± 24.6 |
| C909 | 3 | 0.9 mg/30 μL/eye | 94.2 ± 2.3 | 76.8 ± 2.5 | 32.8 ± 4.0 |

Table 33 and FIG. 17 show data over a 6-month period involving formulations C907 to C909, C914, and C915 for the sirolimus concentration in the retina-choroid.

TABLE 33

(concentrations of sirolimus in the retina-choroid)

| Pharmaceutical Composition | Concentration of Sirolimus | | Concentration of Sirolimus (ng/g) | | |
|---|---|---|---|---|---|
| Formulation | (% W/W) | Dose | 1 Month | 3 Months | 6 Months |
| C907 | 3 | 0.9 mg/30 μL/eye | 780 ± 889 | 709 | 196 ± 97.5 |
| C908 | 3 | 0.9 mg/30 μL/eye | 263 ± 198 | 441 ± 73.7 | 276 ± 55.1 |
| C914 | 3 | 0.9 mg/30 μL/eye | 1693 ± 1653 | 1015 ± 411 | 420 ± 590 |
| C915 | 3 | 0.9 mg/30 μL/eye | 2877 ± 2668 | 769 ± 160 | 393 |
| C909 | 3 | 0.9 mg/30 μL/eye | 974 ± 343 | 744 ± 270 | 164 ± 40.0 |

Blood levels of sirolimus were measured at 30-day intervals for formulations C907 to C909, C914, and C915. The results are shown in FIG. 18.

Example 12: Pharmaceutical Compositions and In Vivo PK Study

The composition was prepared as in Table 34. Amounts of excipients are expressed as parts by weight. The pharmaceutical compositions contained sirolimus in a concentration of 30 mg/g.

TABLE 34

| | C914 |
|---|---|
| SRL | 3 |
| SAIB | 47.5 |
| BB | 43.7 |
| EtOH | 4.8 |
| VE | 1 |

Rabbit PK Study Following Intravitreal Injection of Sirolimus Solution Formulations:

Male Japanese white rabbits were systemically anesthetized and thereafter, both eyes were anesthetized on the surface by administering eye drops of oxybuprocaine hydrochloride (0.5%). The rabbits received a single bilateral intravitreal injection of 30 microliters of test formulation. The rabbits were euthanized 4 weeks and 12 weeks after administration. The enucleated eyes were dissected while frozen and the vitreous humor was isolated. Amount of sirolimus in vitreous body was determined using liquid chromatography combined with tandem mass spectrometry.

Table 35 and FIG. 19 show data over a 3-month period involving formulation C914 for the amount of sirolimus remaining in the vitreous humor.

TABLE 35

(remaining ratios of sirolimus in the vitreous humors)

| Pharmaceutical Composition | Concentration of Sirolimus | Setting Dose (Setting value: administered amount of | Remaining Ratio of Sirolimus to Initial Administered Sirolimus (%) | | |
|---|---|---|---|---|---|
| Formulation | (% W/W) | sirolimus) | 1 M | 3 M | 6 M |
| C914 | 3 | 0.9 mg/30 μL/eye | 124.2 | 74.8 ± 1.1 | Not yet obtained |

Table 36 and FIG. 20 show data over a 3-month period involving formulation C914 for the sirolimus concentration in the retina-choroid.

TABLE 36

(concentrations of sirolimus in the retina-choroid)

| Pharmaceutical Composition | Concentration of Sirolimus | | Concentration of Sirolimus (ng/g) | | |
|---|---|---|---|---|---|
| Formulation | (% W/W) | Dose | 1 Month | 3 Months | 6 Months |
| C914 | 3 | 0.9 mg/30 μL/eye | 705 | 1135 ± 573 | Not yet obtained |

Blood levels of sirolimus were measured at 30-day intervals for formulation C914. The results are shown in FIG. 21.

Example 13

Compositions are listed in Table 37. Amounts of excipients are expressed as parts by weight. The pharmaceutical compositions contained sirolimus in concentration between 10 to 35 mg/g.

Preparation of Test Articles:

Benzyl benzoate, ethanol and acetyl tri-n-butyl citrate were weighed in a bottle and mixed well. Vitamin E was added and mixed. Sirolimus at concentrations listed in Table 37 was added, solution was stirred until all dissolved. The resulting solutions were sterile filtered using 0.2 μm pore size sterile filters.

TABLE 37

| Formulation | C1001 | C1002 | C1003 | C1004 | C1005 | C1006 |
|---|---|---|---|---|---|---|
| SRL | 3 | 3 | 3 | 3 | 3.5 | 1 |
| BB | 38.8 | 39.7 | 35 | 81.5 | 38.6 | 39.6 |
| EtOH | 4.8 | 4.8 | 4.8 | 4.8 | 4.8 | 4.9 |
| Acetyl tri-n-butyl citrate | 52.4 | 52.4 | 52.4 | 9.7 | 52.1 | 53.5 |
| VE | 1 | 0.1 | 4.8 | 1 | 1 | 1 |

Rabbit PK Study Following Intravitreal Injection of Sirolimus Solution Formulations:

Male Japanese white rabbits were systemically anesthetized and thereafter, both eyes were anesthetized on the surface by administering eye drops of oxybuprocaine hydrochloride (0.4%). The rabbits received a single bilateral intravitreal injection of 30 or 50 microliters of test formulation. The blood was collected via the auricular artery. The rabbits were euthanized 4 weeks after administration. The enucleated eyes were dissected while frozen and the vitreous humor and retina-choroid were isolated. Amounts of sirolimus in vitreous humor, retina-choroid and whole blood were determined using liquid chromatography combined with tandem mass spectrometry.

Table 38 shows data over a 1-month period involving formulations C1001 to C1006 for the amount of sirolimus remaining in the vitreous humor.

TABLE 38

(remaining ratios of sirolimus in the vitreous humors)

| Pharmaceutical Composition | Concentration of Sirolimus | | Remaining Ratio of Sirolimus to Initial Administered Sirolimus (%) | | |
|---|---|---|---|---|---|
| Formulation | (% W/W) | Dose | 1 M | 3 M | 6 M |
| C1001 | 3 | 0.9 mg/30 μL/eye | 79.1 ± 9.6 | Not yet obtained | |
| C1002 | 3 | 0.9 mg/30 μL/eye | 78.9 ± 10.8 | Not yet obtained | |
| C1003 | 3 | 0.9 mg/30 μL/eye | 73.6 ± 7.9 | Not yet obtained | |
| C1005 | 3.5 | 1.05 mg/30 μL/eye | 82.4 ± 9.4 | Not yet obtained | |
| C1006 | 1 | 0.3 mg/30 μL/eye | 78.4 ± 8.5 | Not yet obtained | |
| C1001 | 3 | 0.9 mg/30 μL/eye | 83.4 ± 3.2 | Not yet obtained | |
| C1001 | 3 | 1.5 mg/50 μL/eye | 90.5 ± 10.0 | Not yet obtained | |
| C1004 | 3 | 0.9 mg/30 μL/eye | 88.3 ± 30.3 | Not yet obtained | |

Table 39 shows data over a 1-month period involving formulations C1001 to C1006 for the sirolimus concentration in the retina-choroid.

TABLE 39

(concentrations of sirolimus in the retina-choroid)

| Pharmaceutical Composition | Concentration of Sirolimus | | Concentration of Sirolimus (μg/g) | | |
|---|---|---|---|---|---|
| Formulation | (% W/W) | Dose | 1 M | 3 M | 6 M |
| C1001 | 3 | 0.9 mg/30 μL/eye | 0.792 ± 0.979 | Not yet obtained | |
| C1002 | 3 | 0.9 mg/30 μL/eye | 1.42 | Not yet obtained | |

TABLE 39-continued (concentrations of sirolimus in the retina-choroid)

| Pharmaceutical Composition Formulation | Concentration of Sirolimus (% W/W) | Dose | Concentration of Sirolimus (μg/g) | | |
|---|---|---|---|---|---|
| | | | 1 M | 3 M | 6 M |
| C1003 | 3 | 0.9 mg/30 μL/eye | 3.77 ± 2.89 | Not yet obtained | |
| C1005 | 3.5 | 1.05 mg/30 μL/eye | 1.54 ± 1.74 | Not yet obtained | |
| C1006 | 1 | 0.3 mg/30 μL/eye | 1.88 ± 1.55 | Not yet obtained | |
| C1001 | 3 | 0.9 mg/30 μL/eye | 2.33 ± 1.47 | Not yet obtained | |
| C1001 | 3 | 1.5 mg/50 μL/eye | 2.51 ± 1.70 | Not yet obtained | |
| C1004 | 3 | 0.9 mg/30 μL/eye | 6.16 | Not yet obtained | |

Blood levels of sirolimus were measured for formulations C1001 to C1006. The results are shown in Table 40.

TABLE 40

(sirolimus concentration in whole blood (ng/mL))

| Formulation | Concentration of sirolimus (% W/W) | Dose | Concentration of sirolimus (ng/mL) | | | | | | |
|---|---|---|---|---|---|---|---|---|---|
| | | | 0.083 day | 1 day | 3 day | 7 day | 14 day | 28 day | 57 day |
| C1001 | 3 | 0.9 mg/30 μL/eye | 0.487 ± 0.083 | 0.905 ± 0.597 | 0.437 ± 0.488 | 0.366 ± 0.185 | 0.228 ± 0.052 | 0.389 ± 0.191 | 0.752 ± 0.129 |
| C1002 | 3 | 0.9 mg/30 μL/eye | 0.713 ± 0.292 | 1.18 ± 0.70 | 0.491 ± 0.077 | 0.423 ± 0.150 | 0.231 ± 0.237 | 0.456 ± 0.157 | 0.680 ± 0.440 |
| C1003 | 3 | 0.9 mg/30 μL/eye | 0.731 ± 0.430 | 0.910 ± 0.432 | 0.691 ± 0.281 | 0.391 ± 0.201 | 0.383 ± 0.210 | 0.548 ± 0.151 | 0.728 ± 0.224 |
| C1005 | 3.5 | 1.05 mg/30 μL/eye | 0.873 ± 0.248 | 0.994 ± 0.856 | 0.526 ± 0.273 | 0.402 ± 0.161 | 0.461 ± 0.137 | 0.530 ± 0.136 | 0.776 ± 0.332 |
| C1006 | 1 | 0.3 mg/30 μL/eye | 0.367 ± 0.314 | 0.491 ± 0.186 | 0.239 ± 0.067 | 0.271 ± 0.057 | 0.168 ± 0.031 | 0.142 ± 0.096 | 0.255 ± 0.084 |
| C1001 | 3 | 0.9 mg/30 μL/eye | 0.991 ± 0.107 | 1.10 ± 0.02 | 0.541 ± 0.116 | 0.539 ± 0.046 | 0.403 ± 0.047$^a$ | 0.563 ± 0.098 | 0.799 ± 0.101$^b$ |
| C1001 | 3 | 1.5 mg/50 μL/eye | 0.933 ± 0.652 | 2.60 ± 0.46 | 1.19 ± 0.14 | 0.964 ± 0.483 | 0.658 ± 0.404$^a$ | 0.760 ± 0.339 | 1.02 ± 0.58$^b$ |
| C1004 | 3 | 0.9 mg/30 μL/eye | 1.02 ± 0.25 | 2.02 ± 0.37 | 0.689 ± 0.308 | 0.520 ± 0.145 | 0.321 ± 0.067$^a$ | 0.389 ± 0.102 | 0.559 ± 0.024$^b$ |

$^a$15 day
$^b$56 day

Example 14: Pharmaceutical Compositions

Compositions are prepared as in Table 41. Amounts of excipients are expressed as parts by weight. The pharmaceutical compositions contain sirolimus in a concentration of 30 mg/g.

TABLE 41

| | C1101 | C1102 | C1103 |
|---|---|---|---|
| SRL | 3 | 3 | 3 |
| SAIB | 9.7 | 9.7 | 1 |
| BB | 38.8 | 38.8 | 43.2 |
| EtOH | 4.8 | 4.8 | 4.8 |
| PLXM | 1 | 1 | 0.5 |
| VE | 1 | 1 | 1 |
| Lauroglycol 90 | 41.7 | — | — |
| Ceraphyl 30 | — | 41.7 | — |
| Labrafac PG | — | — | 46.5 |

Example 15: SAIB/VE Mixtures

Preparation of SAIB/VE Mixtures:
SAIB was dissolved in VE (at weight ratios shown in Table 42) and the mixture was mixed until uniform.
Density Testing:
About 2 mL of the mixture was injected into a density meter to measure the density of the mixture at 25° C.

As shown in Table 42, the density increased depending on the weight ratio of SAIB:VE. In addition, there was linear correlation of weight ratio of SAIB:VE and density at 25° C. as shown in FIG. 22. According to the linear approximation equation; Density (at 25° C.)=0.0016×(Weight ratio of SAIB:VE)+0.9445, the weight ratio of SAIB:VE is about 34.7% when the density is 1. Therefore, the mixture can float in water when the weight ratio of SAIB:VE is below about 34.7%.

Vitreous humor has a density slightly higher than water (about 1.0053 g/ml), and is generally at body temperature (37° C.) rather than 25° C. The present depot formulations including SAIB and VE are injected into vitreous humor and release API and the other excipients. At the end of release time, the depot consists mainly of SAIB, VE and API, because almost all of the other excipients have released. If the weight ratio of SAIB:VE is below about 38% in the depot formulation, the depot may float in the vitreous humor, causing discomfort to patients.

TABLE 42

| Mixture Sample No. | Weight ratio of SAIB:VE (%) | Weight ratio of VE:SAIB (%) | Total (%) | Density at 25° C. (g/cm$^2$) |
|---|---|---|---|---|
| 1 | 0 | 100 | 100 | 0.9462 |
| 2 | 10 | 90 | 100 | 0.9588 |
| 3 | 25 | 75 | 100 | 0.9859 |
| 4 | 40 | 60 | 100 | 1.0049 |
| 5 | 50 | 50 | 100 | 1.0283 |

Example 16: Pharmaceutical Compositions

Compositions are prepared as in Tables 43 and 44. Amounts of components of the vehicles are expressed as parts by weight per 100 parts of the compositions. All compositions in Tables 42 and 43 have sirolimus concentrations of 30 mg/g.

TABLE 43

|       | C1701 | C1702 | C1703 | C1704 | C1705 | C1706 | C1707 | C1708 | C1709 | C1710 |
|-------|-------|-------|-------|-------|-------|-------|-------|-------|-------|-------|
| SRL   | 3     | 3     | 3     | 3     | 3     | 3     | 3     | 3     | 3     | 3     |
| SAIB  | 1     | 2     | 3     | 4     | 4.9   | 5.9   | 6.8   | 7.8   | 8.8   | 9.7   |
| BB    | 43.7  | 42.7  | 41.7  | 40.7  | 39.8  | 38.8  | 37.9  | 36.9  | 35.9  | 35    |
| PEG400| 46.5  | 46.5  | 46.5  | 46.5  | 46.5  | 46.5  | 46.5  | 46.5  | 46.5  | 46.5  |
| EtOH  | 4.8   | 4.8   | 4.8   | 4.8   | 4.8   | 4.8   | 4.8   | 4.8   | 4.8   | 4.8   |
| VE    | 1     | 1     | 1     | 1     | 1     | 1     | 1     | 1     | 1     | 1     |

TABLE 44

|       | C1711 | C1712 | C1713 | C1714 | C1715 | C1716 | C1717 | C1718 | C1719 | C1720 |
|-------|-------|-------|-------|-------|-------|-------|-------|-------|-------|-------|
| SRL   | 3     | 3     | 3     | 3     | 3     | 3     | 3     | 3     | 3     | 3     |
| SAIB  | 1     | 2     | 2.9   | 3.9   | 4.9   | 5.8   | 6.8   | 7.8   | 8.7   | 9.7   |
| BB    | 90.2  | 89.2  | 88.3  | 87.3  | 86.3  | 85.4  | 84.4  | 83.4  | 82.5  | 81.5  |
| EtOH  | 4.8   | 4.8   | 4.8   | 4.8   | 4.8   | 4.8   | 4.8   | 4.8   | 4.8   | 4.8   |
| VE    | 1     | 1     | 1     | 1     | 1     | 1     | 1     | 1     | 1     | 1     |

Example 17: Fluocinolone Acetonide Formulations

Compositions listed in Table 45 were prepared by adding 3% w/w fluocinolone to the vehicles. Resulting formulations were solutions with some excess solid. Amounts of excipients in Table 45 are expressed as parts by weight.

TABLE 45

Formulations of Fluocinolone Acetonide in Vehicles

|              | C1721 | C1722 | C1723 |
|--------------|-------|-------|-------|
| Fluocinolone | 3     | 3     | 3     |
| SAIB         | 48    | 1     | 10    |
| BB           | 45    | 45    | 40    |
| EtOH         | 5     | 5     | 5     |
| PLXM         | 1     | 1     | —     |
| PEG400       | —     | —     | 44    |
| VE           | 1     | 1     | 1     |
| TEC          | —     | 47    | —     |

In Vitro Release Testing of Fluocinolone Formulations:

50 µL formulations were injected into 5 mL release medium (PBS containing 0.2% SDS, equilibrated at 37° C.) using 1 mL EXEL syringe with 23 G needle. Samples were placed on an orbital shaker rotating at 50 rpm at 37° C. At each time point 4.5 mL media was pulled and replaced by fresh 4.5 mL. Care was taken not to touch the drug depot during sampling. Samples were analyzed by HPLC to determine concentration of fluocinolone. Samples were prepared in triplicates. Release profiles of fluocinolone formulations are shown in FIG. 23.

Example 18: Triamcinolone Formulations

Compositions listed in Table 46 were prepared by adding 3% w/w triamcinolone to the vehicles. Resulting formulations were solutions with some excess solid. Amounts of excipients in Table 46 are expressed as parts by weight.

TABLE 46

Formulations of Triamcinolone in Vehicles

|               | C1724 | C1725 | C1726 |
|---------------|-------|-------|-------|
| Triamcinolone | 3     | 3     | 3     |
| SAIB          | 48    | 1     | 10    |
| BB            | 45    | 45    | 40    |
| EtOH          | 5     | 5     | 5     |
| PLXM          | 1     | 1     | —     |
| PEG400        | —     | —     | 44    |
| VE            | 1     | 1     | 1     |
| TEC           | —     | 47    | —     |

In Vitro Release Testing of Triamcinolone Formulations:

50 µL formulations were injected into 5 mL release medium (PBS containing 0.2% SDS, equilibrated at 37° C.) using 1 mL EXEL syringe with 23 G needle. Samples were placed on an orbital shaker rotating at 50 rpm at 37° C. At each time point 4.5 mL media was pulled and replaced by fresh 4.5 mL. Care was taken not to touch the drug depot during sampling. Samples were analyzed by HPLC to determine concentration of triamcinolone. Samples were prepared in triplicates. Release profiles of triamcinolone formulations are shown in FIG. 24.

Example 19: Ibuprofen Formulations

Compositions listed in Table 47 were prepared by adding 3% w/w ibuprofen to the vehicles. Resulting formulations were clear solutions. Amounts of excipients in Table 47 are expressed as parts by weight.

TABLE 47

Formulations of Ibuprofen in Vehicles

|           | C1727 | C1728 | C1729 |
|-----------|-------|-------|-------|
| Ibuprofen | 3     | 3     | 3     |
| SAIB      | 48    | 1     | 10    |
| BB        | 45    | 45    | 40    |
| EtOH      | 5     | 5     | 5     |
| PLXM      | 1     | 1     | —     |
| PEG400    | —     | —     | 44    |
| VE        | 1     | 1     | 1     |
| TEC       | —     | 47    | —     |

In Vitro Release Testing of Ibuprofen Formulations:

50 µL formulations were injected into 5 mL release medium (PBS containing 0.2% SDS, equilibrated at 37° C.)

using 1 mL EXEL syringe with 23 G needle. Samples were placed on an orbital shaker rotating at 50 rpm at 37° C. At each time point 4.5 mL media was pulled and replaced by fresh 4.5 mL. Care was taken not to touch the drug depot during sampling. Samples were analyzed by HPLC to determine concentration of ibuprofen. Samples were prepared in triplicates. Release profile of ibuprofen formulations is shown in FIG. 25.

All of the compositions (pharmaceutical and vehicle) disclosed in the preceding Examples and taught throughout this disclosure may be used in pre-clinical and/or clinical studies, including in vitro studies, animal studies, and/or clinical studies, any of which may be directed to, e.g. properties (e.g., drug release rate), pharmacokinetics, pharmacodynamics, toxicology, safety, and/or efficacy. The compositions may be therapeutically used in humans (clinical use) or in animals (veterinary use), in humans or animals in need of such therapy.

The invention claimed is:

1. A composition comprising:
   sirolimus present in an amount ranging from about 1 wt % to about 10 wt %, based on weight of the composition;
   sucrose acetate isobutyrate (SAIB) present in an amount ranging from about 0.1 wt % to about 10 wt %, based on weight of the composition;
   benzyl benzoate present in an amount ranging from about 30 wt % to about 60 wt %, based on weight of the composition;
   ethanol present in an amount ranging from about 1 wt % to about 10 wt %, based on weight of the composition;
   polyethylene glycol (PEG) present in an amount ranging from about 30 wt % to about 60 wt %, based on weight of the composition; and
   vitamin E present in an amount ranging from about 0.1 wt % to about 5 wt %, based on weight of the composition wherein when the composition is administered intraocularly as a single dose to a rabbit, a median amount of sirolimus released from the composition at 6 months after administration ranges from 30% to 100% of a total amount of the sirolimus in the composition at the time of administration.

2. The composition of claim 1, wherein the composition comprises from about 1 wt % to about 5 wt % of the sirolimus, based on weight of the composition.

3. The composition of claim 1, wherein the benzyl benzoate is present in an amount ranging from about 35 wt % to about 45 wt %, based on weight of the composition.

4. The composition of claim 1, wherein the PEG is present in an amount ranging from about 35 wt % to about 50 wt %, based on weight of the composition.

5. The composition of claim 4, wherein the PEG is present in an amount ranging from about 40 wt % to about 50 wt %, based on weight of the composition.

6. The composition of claim 1, wherein the vitamin E is present in an amount ranging from about 0.5 wt % to about 2 wt %, based on weight of the composition.

7. The composition of claim 1, wherein the composition has a weight ratio of SAIB: vitamin E ranging from about 0.5 to about 10.

8. The composition of claim 1, wherein:
   the sirolimus is present in an amount ranging from about 1 wt % to about 5 wt %, based on weight of the composition;
   the benzyl benzoate is present in an amount ranging from about 30 wt % to about 45 wt %, based on weight of the composition;
   the PEG is present in an amount ranging from about 40 wt % to about 50 wt %, based on weight of the composition; and
   the vitamin E is present in an amount ranging from about 0.5 wt % to about 2 wt %, based on weight of the composition.

9. The composition of claim 1, the composition consisting essentially of:
   sirolimus in an amount ranging from about 1 wt % to about 5 wt %, based on weight of the composition;
   SAIB in an amount ranging from about 0.1 wt % to about 10 wt %, based on weight of the composition;
   benzyl benzoate in an amount ranging from about 30 wt % to about 45 wt %, based on weight of the composition;
   ethanol in an amount ranging from about 1 wt % to about 10 wt %, based on weight of the composition;
   PEG400 in an amount ranging from about 40 wt % to about 50 wt %, based on weight of the composition; and
   vitamin E in an amount ranging from about 0.5 wt % to about 2 wt %, based on weight of the composition.

10. The composition of claim 1, wherein the composition is pharmaceutically acceptable.

* * * * *